(12) United States Patent
Li et al.

(10) Patent No.: US 11,149,008 B2
(45) Date of Patent: Oct. 19, 2021

(54) SULFAMIDE DERIVATIVES AND PREPARATION METHOD AND USE THEREOF

(71) Applicant: HitGen Ltd., Sichuan (CN)

(72) Inventors: Jin Li, Sichuan (CN); Xueming Li, Sichuan (CN); Dengfeng Dou, Sichuan (CN); Jinqiao Wan, Sichuan (CN); Wei Zhang, Sichuan (CN); Jingming Li, Sichuan (CN); Yan Lan, Sichuan (CN); Linli Li, Sichuan (CN)

(73) Assignee: HitGen, Inc.

( * ) Notice: Subject to any disclaimer, the term of this patent is extended or adjusted under 35 U.S.C. 154(b) by 0 days.

(21) Appl. No.: 16/067,097

(22) PCT Filed: Dec. 29, 2016

(86) PCT No.: PCT/CN2016/112896
§ 371 (c)(1),
(2) Date: Jun. 28, 2018

(87) PCT Pub. No.: WO2017/114448
PCT Pub. Date: Jul. 6, 2017

(65) Prior Publication Data
US 2019/0031612 A1     Jan. 31, 2019

(30) Foreign Application Priority Data
Dec. 31, 2015   (CN) .......................... 201511029249.6

(51) Int. Cl.
| C07D 211/96 | (2006.01) |
|---|---|
| C07D 401/12 | (2006.01) |
| C07D 401/14 | (2006.01) |
| C07D 411/12 | (2006.01) |
| A61P 35/00 | (2006.01) |
| A61K 31/44 | (2006.01) |
| C07D 211/78 | (2006.01) |

(52) U.S. Cl.
CPC ............ *C07D 211/96* (2013.01); *A61K 31/44* (2013.01); *A61P 35/00* (2018.01); *C07D 211/78* (2013.01); *C07D 401/12* (2013.01); *C07D 401/14* (2013.01); *C07D 411/12* (2013.01)

(58) Field of Classification Search
CPC .. C07D 211/96; C07D 401/12; C07D 401/14; C07D 411/12
See application file for complete search history.

(56) References Cited

FOREIGN PATENT DOCUMENTS

| WO | 2004013324 A1 | 2/2004 |
|---|---|---|
| WO | 2010007027 A | 1/2010 |

OTHER PUBLICATIONS

PCT International Search Report in PCT International Application No. PCT/CN2016/112896 dated Apr. 1, 2017.
"STN Search System Registry Database", the search result, Mar. 9, 2009 (Mar. 9, 2009), the registration numbers of compound CA: 1116077-46-3, 1115941-67-7, 1115941-68-8, 1115988-47-0, 1115988-50-5 and 1115988-51-6.
"STN Search System Registry Database", the search result, Feb. 26, 2009 (Feb. 26, 2009), the registration numbers of compound CA: 1111957-50-6, 1111957-58-4, 1111957-80-2, 1111957-88-0, 1111958-12-3, 1111958-28-1, 1111958-44-1, 1111994-28-5 etc.
"STN Search System Registry Database", the search result, Feb. 2, 2009 (Feb. 2, 2009), the registration numbers of compound CA: 1100351-77-6 and 1100351-78-7.
"STN Search System Registry Database", the search result, Feb. 15, 2007 (Feb. 15. 2007), the registration number of compound CA: 921055-47-2, 921055-92-7, 921056-34-0, 921115-27-7, 921142-39-4, 921142-43-0, 921142-65-6, 921159-05-9, 921159-39-9 and 921159-78-6.
"STN Search System Registry Database", the search result, Feb. 11, 2007 (Feb. 11, 2007), the registration numbers of compound CA: 920433-00-7, 920452-07-9 and 920478-29-1.
"STN Search System Registry Database", the search result, Aug. 23, 2006 (Aug. 23, 2006), the registration numbers of compound CA: 903868-42-8, 903849-88-7, 903850-03-3, 903852-55-1, 903864-88-0 and 903868-29-1.
"STN Search System Registry Database", the search result, Aug. 22, 2006 (Aug. 22, 2006), the registration numbers of compound CA: 903191-11-7 and 903205-74-3.
"STN Search System Registry Database", the search result, Mar. 3, 2005 (Mar. 3, 2005), the registration numbers of compound CA: 841287-97-6 and 841287-98-7.

(Continued)

*Primary Examiner* — Brian E McDowell
(74) *Attorney, Agent, or Firm* — Greenberg Traurig, LLP; Fang Xie

(57) ABSTRACT

The present invention discloses a compound shown in formula I or a stereoisomer, pharmaceutically acceptable salt, crystal form, solvate or isotopologue thereof. The compound of the present invention shows excellent inhibition activity against histone deacetylases, has remarkable inhibition effects on cancer cells, and provides a new choice of drugs used for the clinic treatment and diseases related to the abnormal activity of histone deacetylases.

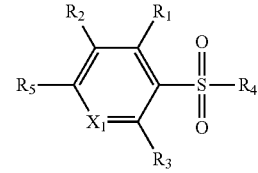

Formula I

26 Claims, No Drawings

(56) References Cited

OTHER PUBLICATIONS

"STN Search System Registry Database", the search result, Feb. 28, 2005 (Feb. 28, 2005), the registration numbers of compound CA: 838863-75-5, 838863-76-6 and 838863-74-4.
"STN Search System Registry Database", the search result, Mar. 3, 2004 (Mar. 3, 2004), the registration numbers of compound CA: 657404-23-4, 657404-24-5 and 657404-42-7.
"STN Search System Registry Database", the search result, Oct. 17, 2003 (Oct. 17, 2003), the registration numbers of compound CA: 606096-17-7, 606097-30-7, 606097-32-9, 606097-33-0, 606097-36-3, 606097-39-6, 606097-42-1, 606097-46-5, 606097-49-8, 606097-50-1, 606097-51-2, 606097-52-3, 606097-53-4, 606097-55-6, 606097-56-7 and 606097-57-8.
"STN Search System Registry Database", the search result, Oct. 14, 2003 (Oct. 14, 2003), the registration numbers of compound CA: 603974-60-3, 603974-65-8, 603974-66-9, 603974-67-0, 603974-68-1, 603974-69-2, 603974-70-5, 603974-71-6, 603974-72-7, 603974-73-8, 603974-74-9, 603974-75-0, 603974-76-1, 603974-77-2, 603974-78-3, 603974-85-2 and 603974-88-5.
"STN Search System Registry Database", the search result, Oct. 13, 2003 (Oct. 13, 2003), the registration numbers of compound CA: 603080-45-1, 603080-51-9 and 603117-97-1.

SULFAMIDE DERIVATIVES AND PREPARATION METHOD AND USE THEREOF

CROSS REFERENCE TO RELATED APPLICATIONS

This application is a U.S. National Phase application under 35 U.S.C. 371 of International Application No. PCT/CN2016/112896, filed Dec. 29, 2016, which claims priority to and the benefit of Chinese Application No. 201511029249.6 filed Dec. 31, 2015, the disclosure of each of which is incorporated herein by reference.

TECHNICAL FIELD

The present invention relates to sulfamide derivatives and preparation methods and applications thereof, and in particular to sulfamide derivatives having histone deacetylase inhibition activity and preparation methods and applications thereof.

BACKGROUND OF THE PRESENT INVENTION

The inactivation of genes controlling the cell growth in the body is a sign of tumorigenesis. Epigenetic mechanisms that cause the inactivation of genes mainly include DNA methylation, histone acetylation and modifications of other components in the high-level chromatin structure. These modifications change the chromatin configuration and thus change the regulation of gene transcription. The disorder of the gene transcription leads to the abnormal cell proliferation and thus results in tumorigenesis.

Over 40 years ago, Allfrey et. al. recognized that the acetylation of histones is closely related to the transcription regulation of eukaryotic genes (Allfrey V G, Faulkner R, Mirsky A E. Acetylation and methylation of histones and their possible role in the regulation of RNA synthesis. Proc Natl Acad Sci USA, 1964, 51:786-794). The histone acetylation plays a core role in the transcription regulation of eukaryotic genes. The acetylation of histones occurs at ε-amino of an evolutionarily conserved lysine residue at the N-terminal. Modifications on H3 and H4 are more prevalent than that on H2A and H2B. Relatively important acetylation sits are $Lys^9$ and $Lys^{14}$ on H3, and $Lys^5$, $Lys^8$, $Lys^{12}$ and $Lys^{16}$ on H4. The acetylation of HAT results in the acetylation of amino of lysine at the N-terminal of the histone, and the positive charge on the amino is eliminated, so that the negative charge carried by the DNA molecules themselves facilitates the unfolding of the DNA conformation and the structure of nucleosomes becomes looser. Accordingly, it is advantageous for the contact of transcription factors and synergistic transcription activators with DNA molecules, and the acetylation of histones can activate the transcription and expression of specific genes. On the contrary, the deacetylation of histones is disadvantageous for the expression of specific genes (e.g., Rb, p21 and p27). The acetylation and deacetylation of histones becomes a switch for the expression of specific genes (Thiagalingam S, Cheng K H, Lee H J, et al. Histonedeacetylases: unique players in shaping the epigenetic histone code. Ann N Y Acad Sci, 2003, 983:84-100).

The acetylation of histones is regulated by a pair of functionally antagonistic protease histone acetyltransferases (HATs) and histone deacetylases (HDACs). In normal cells, this pair of enzymes is in a dynamically balanced state. Generally, an increased acetylation level of histones is related to the increased gene transcription activity, and a low acetylation level is related to the inhibition of gene expression (Forsberg E C, Bresnick E H. Histone acetylation beyond promoters: long-range acetylation patterns in the chromatin world. Bioessays, 2001, 23(9):820-830). Studies showed that the overexpression of HDACs and the recruitment of HDACs by transcription factors would lead to the abnormal inhibition of specific genes, thereby resulting in tumors and other diseases; and, the inhibition of the activity of HDACs would lead to the growth inhibition and apoptosis of many cancer cells (Somech R, lzraeli S, J Simon A. Histone deacetylase inhibitors—a new tool to treat cancer. Cancer Treat Rev, 2004, 30(5):461-472). Therefore, the HDAC has become the latest and hottest target in the field of the research and development of anti-tumor drugs currently.

HDAC inhibitors can inhibit the activity of HDACs, and their mechanism of action is to block the inhibition of gene expression resulted from the HDAC recruitment dysfunction by inhibiting HDACs and change the chromatin structure by changing the acetylation level of histones, so as to regulate the gene expression for cancer treatment. The HDAC inhibitors are effective in treating hematological tumors and solid tumors by inducing the growth arrest, differentiation or apoptosis of tumor cells. The HDAC inhibitors are tumor-specific and have cytotoxic effects on both proliferated and quiescent mutant cells; however, normal cells are more than 10 times tolerant to the HDAC inhibitors, and the growth arrest and apoptosis of the normal cells will not be caused. Moreover, since the clinical dosage of HDAC inhibitors is far less than the maximum clinical dosage of the human body, the HDAC inhibitors are less toxic to the body. The development and utilization of the HDAC inhibitors have become a new hotspot for the cancer treatment.

At present, the HDAC inhibitors that have been researched and developed can be classified into five categories: (1) hydroxamic acid compounds, which use hydroxamic acid as a functional group and are represented by TSA, SAHA (Curtin M L, Garland R B, Heyman H R, et al. Succinimide hydroxamic acids as potent inhibitors of histone deacetylase. Bioorg Med Chem Lett, 2002, 12(20): 2919-2923) and LAQ824 (Atadja P, Hsu M, Kwon P, et al. Moleculer and cellular basis for the anti-proliferative effects of the HDAC inhibitor LAQ824. Novartis Found Symp, 2004, 259:249-266); (2) cyclic tetrapeptide containing a 2-amino-8-oxo-9,10-epoxycapryl group or not containing this group, for example, FK-228; (3) benzamide compounds, represented by MS-275 that has been already researched clinically; (4) short-chain fatty acids, for example, butyric acid and phenylbutyric acid; and (5) other category, wherein the HDAC inhibitors of this category do not have structural features of common HDACs, but contain some or all structural subunits required to inhibit the HDAC activity.

SAHA, developed by Merck, is a commercially available histone deacetylase inhibitor which is only limited to the treatment of cutaneous T-cell lymphoma and has no significant curative effects on many other cancers. Other developed HDAC inhibitors also have certain problems in terms of antitumor activity, toxic and side effects, subtype selectivity and the like. Therefore, it is of great economic and social significance to develop novel compounds having inhibition activity against histone deacetylases.

SUMMARY OF THE PRESENT INVENTION

An objective of the present invention is to provide a compound shown in formula I having a novel structure and medicinal value and preparation methods and applications thereof, and a pharmaceutical composition containing this compound, in order to prepare histone deacetylase inhibitor drugs and provide more and better choices of drugs for patients.

The present invention provides a compound shown in formula I, or stereoisomers, pharmaceutically acceptable salts, crystal forms, solvates or isotopologues thereof:

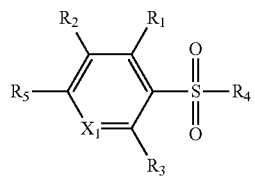

Formula I where $X_1$ is $CR_6$ or N;

$R_1$, $R_2$, $R_3$ and $R_6$ are independently H, halogen, hydroxyl, sulfydryl, amino, phenyl, $C_1$-$C_6$ alkyl, halogen-substituted $C_1$-$C_6$ alkyl, $C_1$-$C_6$ alkoxy or halogen-substituted $C_1$-$C_6$ alkoxy;

$R_4$ is

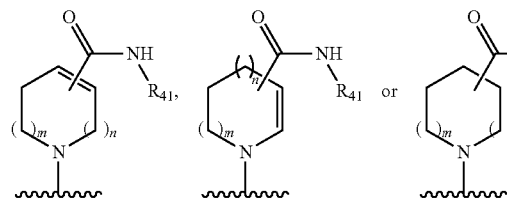

where m and n are independently an integer from 1 to 2;

$R_{41}$ is hydroxyl, sulfydryl, amino, epoxyketone, phenyl or substituted phenyl; and $R_5$ is heterocyclyl, substituted heterocyclyl, aryl, substituted aryl, cycloalkyl or substituted cycloalkyl.

Further, the compound is shown in the following formula II:

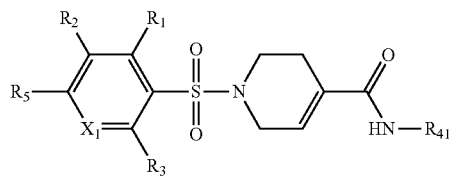

Formula II where $R_1$, $R_2$, $R_3$ and $R_6$ are independently H, F, Cl, methyl, trifluoromethyl, methoxy or trifluoromethoxy;

$R_{41}$ is hydroxyl or sulfydryl; and $R_5$ is imidazolyl, substituted imidazolyl, phenyl, substituted phenyl, pyridyl or substituted pyridyl.

Further, the compound is shown in the following formula IIa:

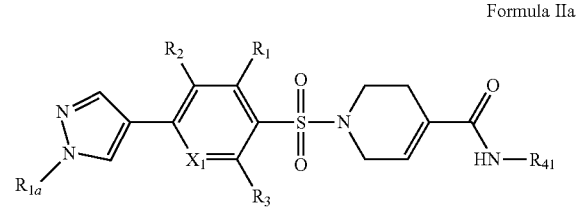

Formula IIa where $R_{1a}$ is H, piperidyl or piperidyl with a substituent group attached to N, wherein the substituent group is $C_1$-$C_6$ alkyl or $C_1$-$C_6$ acyl.

Further, $R_{1a}$ is

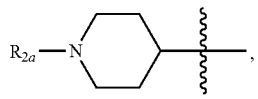

where $R_{2a}$ is H, methyl, ethyl, formyl or acetyl.

Further, the compound shown in the formula IIa is:

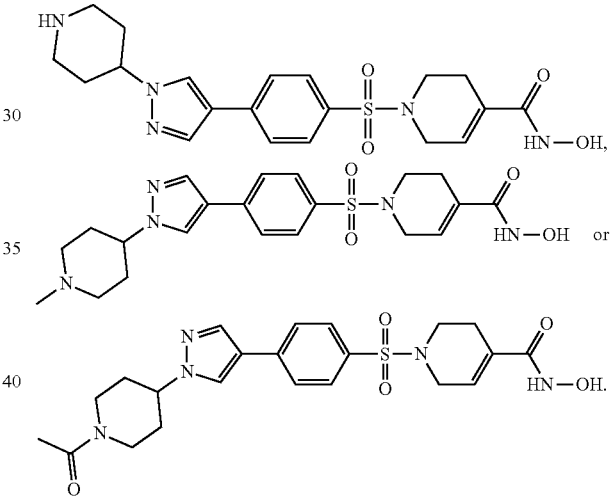

Further, the compound is shown in the following formula IIb:

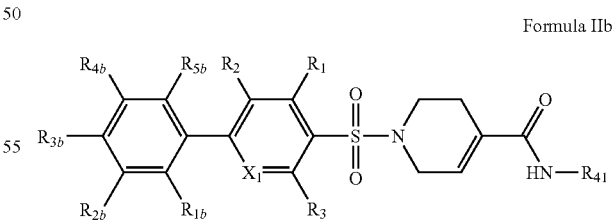

Formula IIb where Rib to $R_{5b}$ are independently H, halogen, hydroxyl, —C(=O)N($R_{21b}$)($R_{22b}$), $C_1$-$C_6$ alkyl, substituted $C_1$-$C_6$ alkyl, piperazinyl, substituted piperazinyl, amino or substituted amino; or, $R_{3b}$ and $R_{4b}$ are linked to form 5-membered to 7-membered heterocyclyl, wherein the heteroatom is N, O or S; and, preferably, the halogen is F or Cl.

Further, only one among $R_{1b}$ to $R_{5b}$ is selected from hydroxyl, —C(=O)N($R_{21b}$)($R_{22b}$), $C_1$-$C_6$ alkyl, substituted $C_1$-$C_6$ alkyl, piperazinyl, substituted piperazinyl, amino or substituted amino; or, $R_{3b}$ and $R_{4b}$ are linked to form 5-membered or 6-membered heterocyclyl, and the heterocyclyl contains only one heteroatom.

Further, when $R_{3b}$ is hydroxyl, the compound is shown in the following formula IIb1:

Formula IIb1

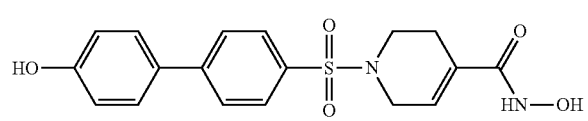

Further, when $R_{3b}$ is —C(=O)N($R_{21b}$)($R_{22b}$), the compound is shown in the following formula IIb2:

Formula IIb2

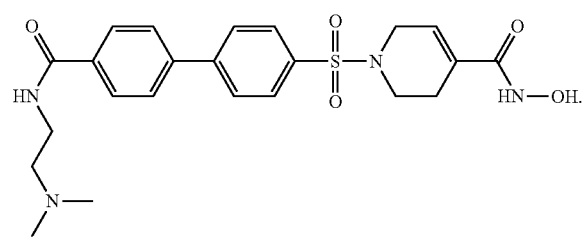

where $R_{21b}$ and $R_{22b}$ are independently H, $C_1$-$C_6$ alkyl, dimethylamino-substituted $C_1$-$C_6$ alkyl or diethylamino-substituted $C_1$-$C_6$ alkyl.

Further, $R_{21b}$ is H, and $R_{22b}$ is $C_1$-$C_3$ alkyl, dimethylamino-substituted $C_1$-$C_3$ alkyl or diethylamino-substituted $C_1$-$C_3$ alkyl.

Further, the compound shown in the formula IIb2 is:

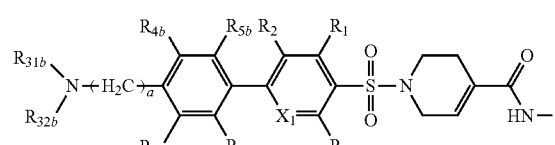

Further, when one of $R_{3b}$ and $R_{5b}$ is selected from substituted amino or substituted $C_1$-$C_6$ alkyl, the compound is shown in the following formula IIb31, IIb32 or IIb33:

Formula IIb31

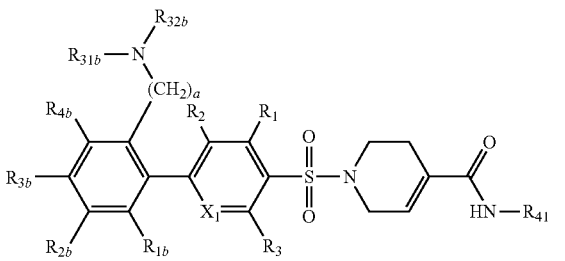

Formula IIb32

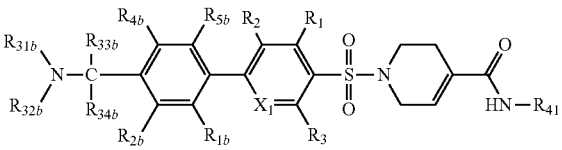

Formula IIb33

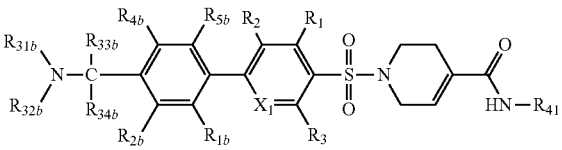

where a is an integer from 0 to 6;

$R_{31b}$ and $R_{32b}$ are independently H, $C_1$-$C_6$ alkyl, substituted $C_1$-$C_6$ alkyl or 5-membered to 7-membered heterocyclyl, wherein the substituent group is $C_1$-$C_6$ alkoxy or $C_1$-$C_6$ alkyl-substituted amino, and the heteroatom is N, O or S; or, $R_{31b}$ and $R_{32b}$ are linked to form 5-membered to 7-membered heterocyclyl; and $R_{33b}$ is H, and $R_{34b}$ is $C_1$-$C_6$ alkyl.

Further, $R_{31b}$ and $R_{32b}$ are independently 6-membered heterocyclyl; or, $R_{31b}$ and $R_{32b}$ are linked to form 6-membered heterocyclyl.

Further, a is an integer from 0 to 3; $R_{31b}$ and $R_{32b}$ are independently H, methyl, ethyl, methoxyethyl, dimethylaminoethyl or

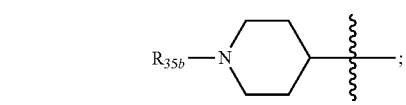

or, $R_{31b}$ and $R_{32b}$ are linked to form

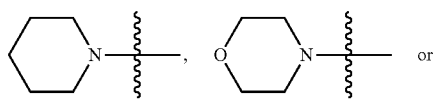

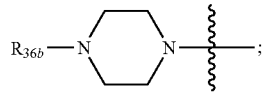

and, $R_{34b}$ is $C_1$-$C_3$ alkyl;

where $R_{35b}$ and $R_{36b}$ are independently $C_1$-$C_6$ alkyl or $C_1$-$C_6$ alkoxy-substituted $C_1$-$C_6$ alkyl.

Further, $R_{35b}$ and $R_{36b}$ are independently $C_1$-$C_4$ alkyl, methoxy-substituted $C_1$-$C_4$ alkyl or ethoxy-substituted $C_1$-$C_4$ alkyl.

Further, the compound shown in the formula IIb31, IIb32 or IIb33 is

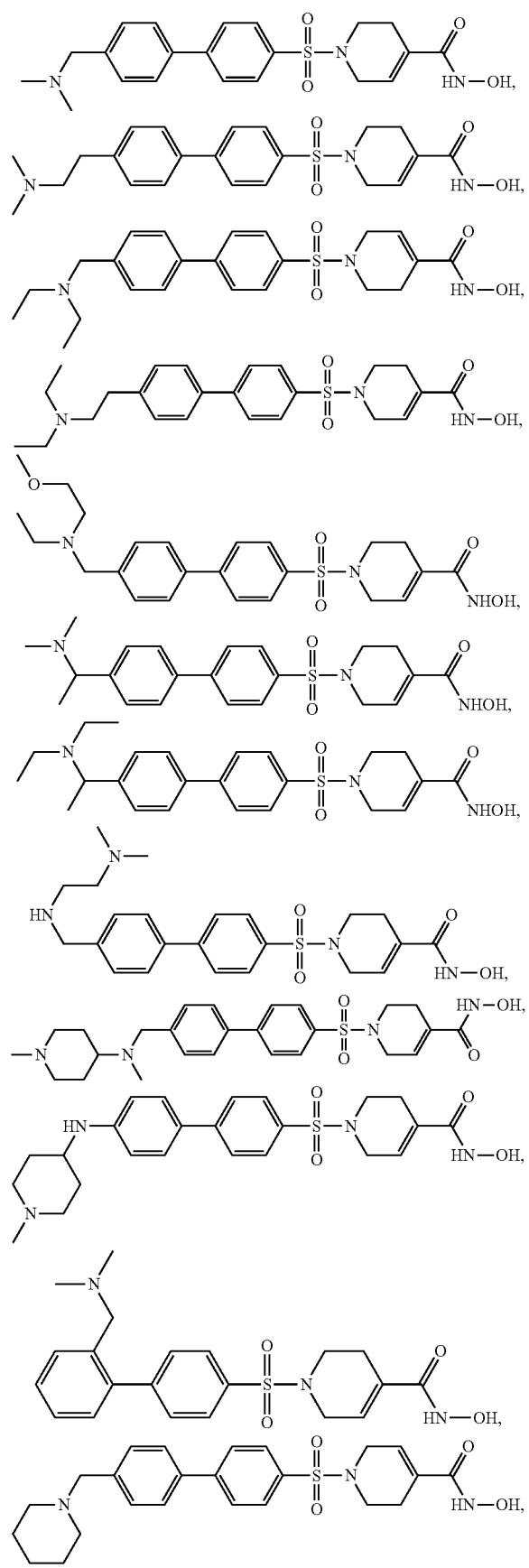

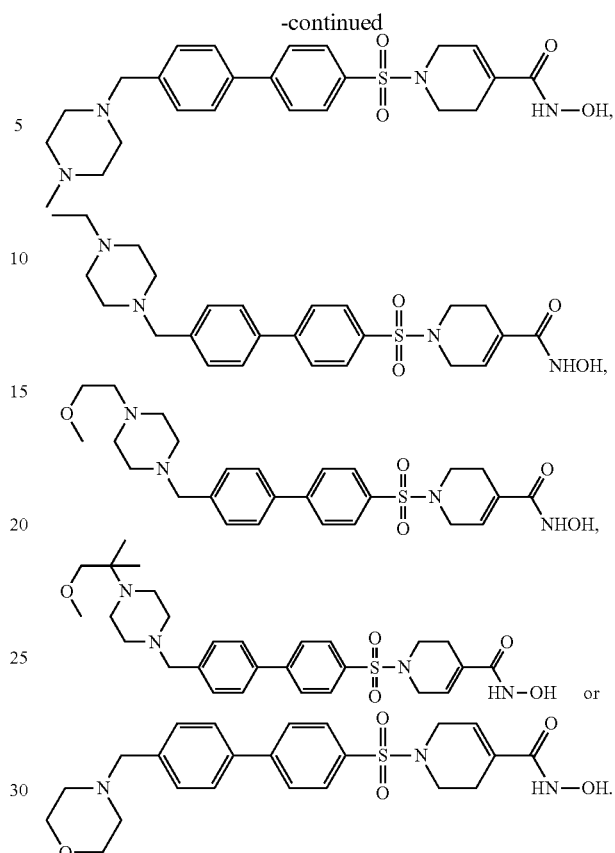

Further, when one of $R_{2b}$ and $R_{3b}$ is selected from piperazinyl or substituted piperazinyl, the compound is shown in the following formula IIb4 or IIb5:

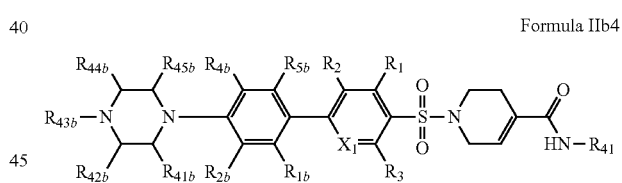

Formula IIb4

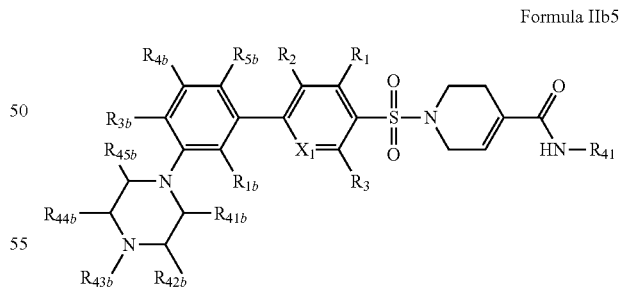

Formula IIb5 where $R_{41b}$, $R_{42b}$, $R_{44b}$ and $R_{45b}$ are independently H or $C_1$-$C_6$ alkyl; and $R_{43b}$ is H, $C_1$-$C_6$ alkyl, methoxy-substituted $C_1$-$C_6$ alkyl, ethoxy-substituted $C_1$-$C_6$ alkyl, $C_1$-$C_6$ acyl or $C_3$-$C_6$ cycloalkyl.

Further, $R_{41b}$, $R_{42b}$, $R_{44b}$ and $R_{45b}$ are independently H, methyl or ethyl; and, $R_{43b}$ is H, methyl, ethyl, methoxy-substituted $C_2$-$C_4$ alkyl, ethoxy-substituted $C_2$-$C_4$ alkyl, acetyl or cyclopropyl.

Further, the compound shown in the formula IIb4 or IIb5 is:

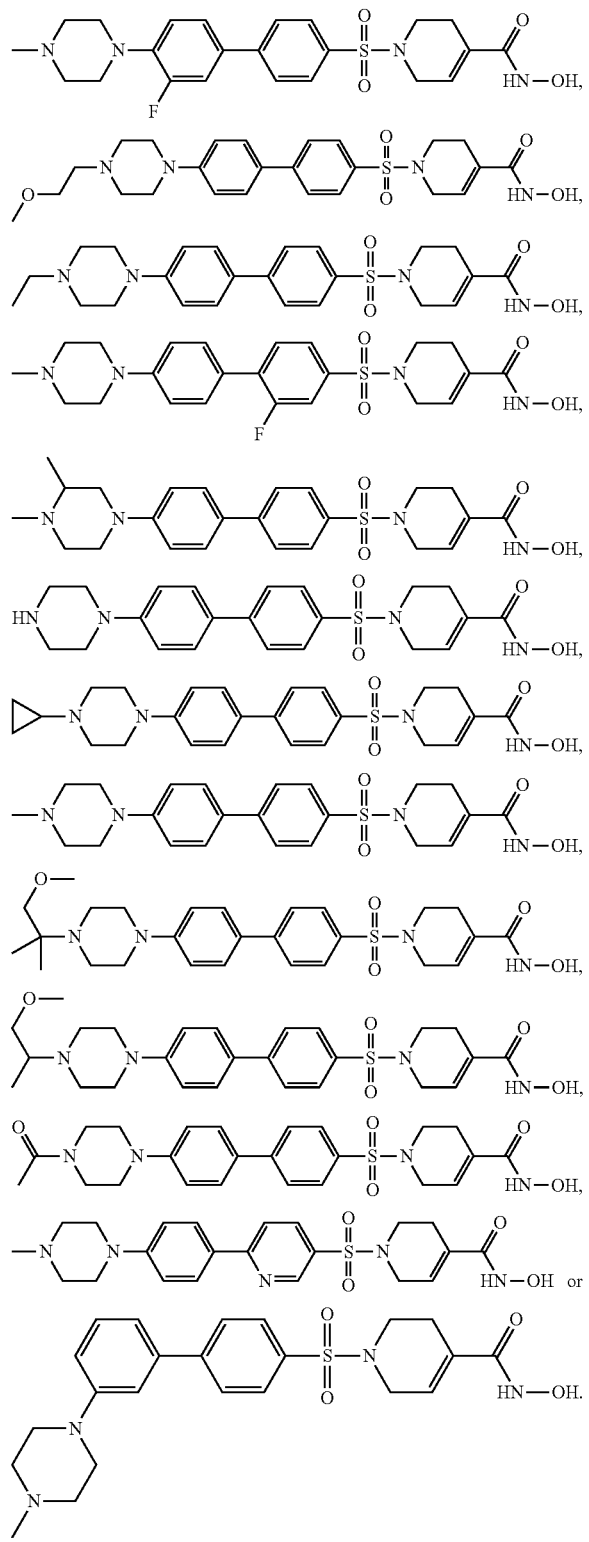

Further, when $R_{3b}$ and $R_{4b}$ are linked to form 5-membered or 6-membered heterocyclyl, the compound is shown in the following formula IIb61 or IIb62:

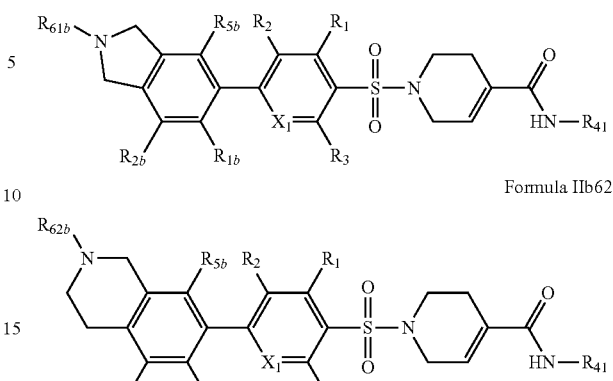

Formula IIb61

Formula IIb62 where $R_{61}b$ and $R_{62b}$ are independently selected from H, $C_1$-$C_6$ alkyl, or $C_1$-$C_6$ alkoxy-substituted $C_1$-$C_6$ alkyl.

Further, $R_{61b}$ and $R_{62b}$ are independently selected from $C_1$-$C_3$ alkyl, methoxy-substituted $C_1$-$C_3$ alkyl or ethoxy-substituted $C_1$-$C_3$ alkyl.

Further, the compound shown in the formula IIb61 or IIb62 is:

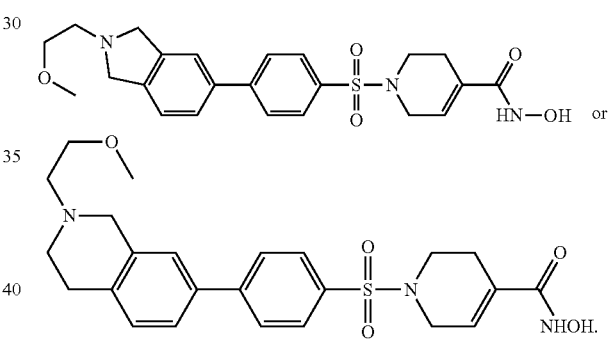

Further, the compound is shown in the following formula IIc:

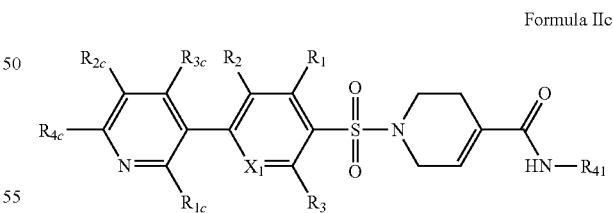

Formula IIc where $R_{1c}$, $R_{2c}$ and $R_3$, are independently H, halogen, $C_1$-$C_6$ alkyl, halogen-substituted $C_1$-$C_6$ alkyl, $C_1$-$C_6$ alkoxy or halogen-substituted $C_1$-$C_6$ alkoxy; and $R_{4c}$ is 5-membered to 7-membered heterocyclyl, wherein the heteroatom is N, O or S.

Further, $R_{1c}$, $R_{2c}$ and $R_3$ are independently H, F, Cl, methyl, trifluoromethyl, methoxy or trifluoromethoxy; and, $R_{4c}$ is 6-membered or 7-membered heterocyclyl, and the heterocyclyl contains at most two heteroatoms.

Further, $R_{4c}$ is

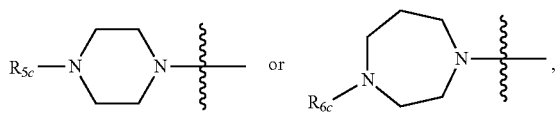

where $R_{5c}$ and $R_{6c}$ are independently selected from $C_1$-$C_6$ alkyl or $C_1$-$C_6$ alkoxy-substituted $C_1$-$C_6$ alkyl; preferably, $R_{5c}$ and $R_{6c}$ are independently selected from $C_1$-$C_3$ alkyl, methoxy-substituted $C_1$-$C_3$ alkyl or ethoxy-substituted $C_1$-$C_3$ alkyl.

Further, the compound shown in the formula IIc is:

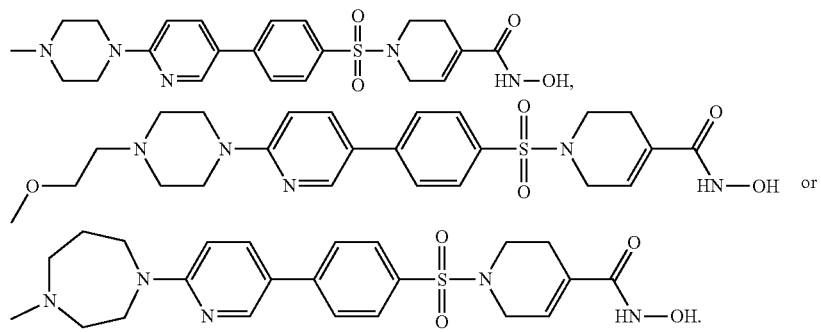

Further, the compound is shown in the following formula III:

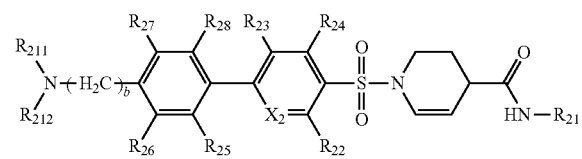

Formula III where $X_2$ is $CR_{29}$ or N;
b is an integer from 0 to 6;
$R_{21}$ is hydroxyl or sulfydryl;
$R_{22}$ to $R_{29}$ are independently H, halogen, $C_1$-$C_6$ alkyl, halogen-substituted $C_1$-$C_6$ alkyl, $C_1$-$C_6$ alkoxy or halogen-substituted $C_1$-$C_6$ alkoxy; and
$R_{211}$ is H, and $R_{212}$ is piperidyl or piperidyl with substituting $C_1$-$C_6$ alkyl attached to N; or, $R_{211}$ and $R_{212}$ are linked to form

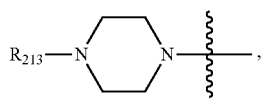

where $R_{213}$ is $C_1$-$C_6$ alkyl or $C_1$-$C_6$ alkoxy-substituted $C_1$-$C_6$ alkyl.

Further, b is 0 or 1; $R_{22}$ to $R_{29}$ are independently H, F, Cl, methyl, trifluoromethyl, methoxy or trifluoromethoxy; $R_{212}$ is piperidyl with substituting $C_1$-$C_3$ alkyl attached to N; $R_{213}$ is $C_1$-$C_4$ alkyl, methoxy-substituted $C_1$-$C_4$ alkyl or ethoxy-substituted $C_1$-$C_4$ alkyl.

Further, the compound shown in the formula III is:

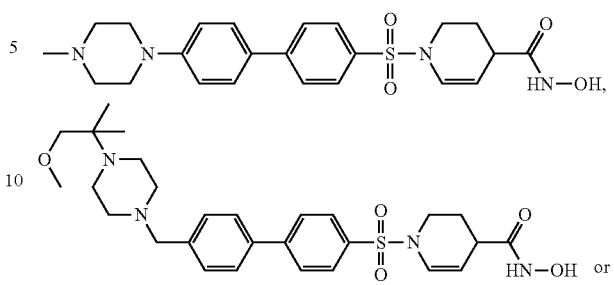

-continued

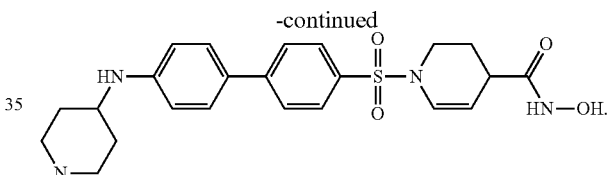

Further, the compound is shown in the following formula IV:

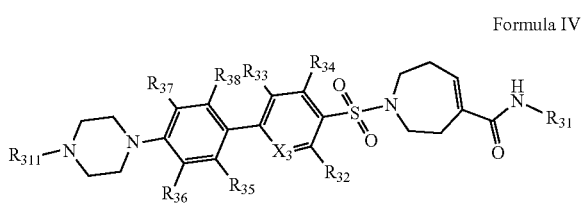

Formula IV where $X_3$ is $CR_{39}$ or N;
$R_{31}$ is hydroxyl or sulfydryl;
$R_{32}$ to $R_{39}$ are independently H, halogen, $C_1$-$C_6$ alkyl, halogen-substituted $C_1$-$C_6$ alkyl, $C_1$-$C_6$ alkoxy or halogen-substituted $C_1$-$C_6$ alkoxy; and
$R_{311}$ is H, $C_1$-$C_6$ alkyl, or $C_1$-$C_6$ alkoxy-substituted $C_1$-$C_6$ alkyl.

Further, $R_{32}$ to $R_{39}$ are independently H, F, Cl, methyl, trifluoromethyl, methoxy or trifluoromethoxy, and $R_{311}$ is methyl or ethyl.

the compound shown in the formula IV is:

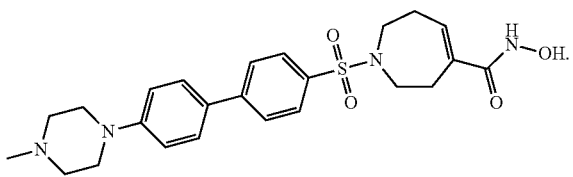 [SMILES: CN1CCN(c2ccc(-c3ccc(S(=O)(=O)N4CCC=C(C(=O)NO)CC4)cc3)cc2)CC1]

The present invention provides a method for preparing the compound, including the following steps: a.

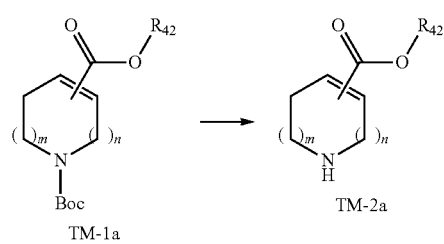

dissolving a compound TM-1a in a halocarbon solvent, adding Lewis acid and reacting to obtain a compound TM-2a;

where $R_{42}$ is $C_1$-$C_6$ alkyl; and preferably, $R_{42}$ is methyl or ethyl;

b.

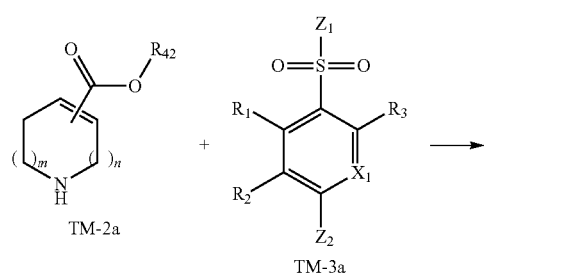

reacting the compound TM-2a, a compound TM-3a and Lewis base in a halocarbon solvent to obtain a compound TM-4a, where $Z_1$ is halogen, and $Z_2$ is halogen or trifluoromethanesulfonate;

c.

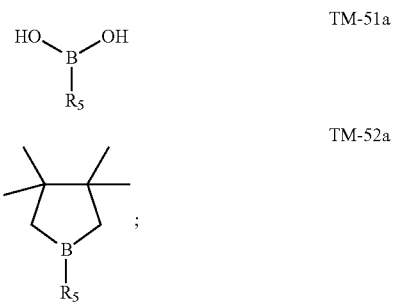

reacting the compound TM-4a, a compound TM-5a, [1,1'-bis(diphenylphosphino)ferrocene]palladium dichloride and Lewis base in a polar aprotic solvent to obtain a compound TM-6a;

where $R_{43}$ and $R_{44}$ are independently selected from H or $C_1$-$C_6$ alkyl; or, $R_{43}$ and $R_{44}$ are linked to form 5-membered to 6-membered dioxaborinane or alkyl-substituted 5-membered to 6-membered dioxaborinane; and, preferably, the compound TM-5a is shown in the structural formula TM-51a or TM-52a:

and
d.

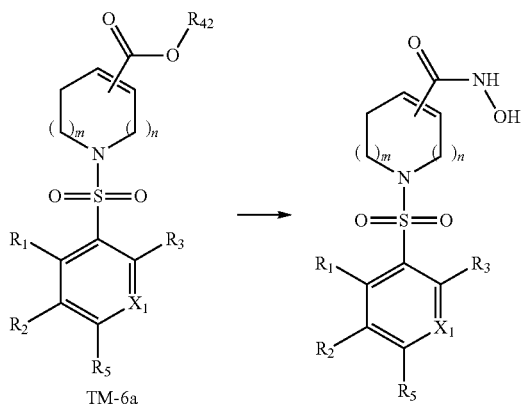

TM-6a dissolving the compound TM-6a in a halocarbon solvent and/or an alcohol solvent, adding hydroxylamine aqueous solution and Lewis base and reacting to obtain the product.

Further:

in the step a, the compound TM-1a is dissolved in the halocarbon solvent at 0° C. to 5° C. and then added with the Lewis acid, and the system is stirred and reacted for 1 h to 12 h at 10° C. to 40° C. to obtain the compound TM-2a, wherein the weight-to-volume ratio of the compound TM-1a to the halocarbon solvent is 1:2-20 g/ml, and the weight-to-volume ratio of the compound TM-1a to the Lewis acid is 1:2-10 g/ml; and the Lewis acid is selected from trifluoroacetic acid or hydrochloric acid;

in the step b, the compound TM-2a, the compound TM-3a, the Lewis base and the halocarbon solvent are stirred and reacted for 1 h to 12 h at 10° C. to 40° C. to obtain the compound TM-4a, wherein the molar ratio of the compound TM-2a to the compound TM-3a is 1:1-2, the molar ratio of the compound TM-2a to the Lewis base is 1:1-5, and the weight-to-volume ratio of the compound TM-2a to the halocarbon solvent is 1:5-200 g/ml; and the Lewis base is selected from triethylamine, diisopropylethylamine or pyridine;

in the step c, under the atmosphere of an inert gas, the compound TM-4a, the compound TM-5a, [1,1'-bis(diphenylphosphino)ferrocene]palladium dichloride, the Lewis base and the polar aprotic solvent are stirred and reacted for 6 h to 24 h at 60° C. to 100° C. to obtain the compound TM-6a, wherein the molar ratio of the compound TM-4a to the compound TM-5a is 1:1-2, the molar ratio of the compound TM-4a to [1,1'-bis(diphenylphosphino)ferrocene]palladium dichloride is 1:0.01-0.2, the molar ratio of the compound TM-4a to the Lewis base is 1:1-5, and the weight-to-volume ratio of the compound TM-4a to the polar aprotic solvent is 1:5-200 g/ml; and the Lewis base is selected from $Na_2CO_3$, $K_2CO_3$ or $Cs_2CO_3$; and in the step d, the compound TM-6a is dissolved in the halocarbon solvent and/or the alcohol solvent at 0° C. to 5° C. and added with hydroxylamine aqueous solution and the Lewis base, and the system is stirred and reacted for 1 h to 12 h at 10° C. to 40° C. to obtain the product, wherein the weight-to-volume ratio of the compound TM-6a to the mixed solvent is 1:10-100 g/ml, the weight-to-volume ratio of the compound TM-6a to the hydroxylamine aqueous solution is 1:5-20 g/ml, and the molar ratio of the compound TM-6a to the Lewis base is 1:2-10;

the volume ratio of the halocarbon solvent to the alcohol solvent in the mixed solvent is 1:0.5-2, and the concentration of the hydroxylamine aqueous solution is 30% to 70%; and the Lewis base is selected from sodium hydroxide or potassium hydroxide.

Further:

in the step a, the reaction temperature is 25° C., the reaction time is 2 h, the weight-to-volume ratio of the compound TM-1a to the halocarbon solvent is 1:5 g/ml, the weight-to-volume ratio of the compound TM-1a to the Lewis acid is 1:5 g/ml, and the Lewis acid is trifluoroacetic acid;

in the step b, the reaction temperature is 25° C., the reaction time is 2 h, the molar ratio of the compound TM-2a to the compound TM-3a is 1:1, the molar ratio of the compound TM-2a to the Lewis base is 1:2, the weight-to-volume ratio of the compound TM-2a to the halocarbon solvent is 1:10-15 g/ml, and the Lewis base is triethylamine;

in the step c, the reaction temperature is 80° C., the reaction time is 12 h, the molar ratio of the compound TM-4a to the compound TM-5a is 1:1, the molar ratio of the compound TM-4a to [1,1'-bis(diphenylphosphino)ferrocene]palladium dichloride is 1:0.05, the molar ratio of the compound TM-4a to the Lewis base is 1:2, the weight-to-volume ratio of the compound TM-4a to the polar aprotic solvent is 1:20-25 g/ml, and the Lewis base is selected from $Na_2CO_3$ or $K_2CO_3$; and in the step d, the reaction temperature is 25° C., the reaction time is 2 h, the weight-to-volume ratio of the compound TM-6a to the mixed solvent is 1:30 g/ml, the weight-to-volume ratio of the compound TM-6a to the hydroxylamine aqueous solution is 1:10 g/ml, the molar ratio of the compound TM-6a to the Lewis base is 1:5, and the volume ratio of the halocarbon solvent to the alcohol solvent in the mixed solvent is 1:1.

Further:

in the step a, the halocarbon solvent is selected from any one or more of dichloromethane, chloroethane, dichloroethane, trichloromethane and carbon tetrachloride;

in the step b, the halocarbon solvent is selected from any one or more of dichloromethane, chloroethane, dichloroethane, trichloromethane and carbon tetrachloride;

in the step c, the inert gas is selected from any one or more of nitrogen, argon and helium, and the polar aprotic solvent is selected from any one or more of N,N-dimethylformamide, N,N-dimethylacetamide, acetonitrile and pyridine; and in the step d, the halocarbon solvent is selected from any one or more of dichloromethane, chloroethane, dichloroethane, trichloromethane and carbon tetrachloride, and the alcohol solvent is selected from any one or more of methanol, ethanol, isopropanol and n-butanol.

The present invention provides an application of the compound or stereoisomers, pharmaceutically acceptable salts, crystal forms, solvates or isotopologues thereof in preparing histone deacetylase inhibitor drugs.

Further, the drugs are drugs for inhibiting one or more of HDAC1, HDAC3 and HDAC6.

The present invention provides an application of the compound or stereoisomers, pharmaceutically acceptable salts, crystal forms, solvates or isotopologues thereof in preparing drugs for treating and/or preventing cell proliferation disorder diseases, autoimmune diseases, inflammations, neurodegenerative diseases or viral diseases.

The present invention provides an application of the compound or stereoisomers, pharmaceutically acceptable salts, crystal forms, solvates or isotopologues thereof in preparing drugs for treating and/or preventing cancers.

Further, the drugs are drugs for treating and/or preventing liver cancer.

The present invention provides a pharmaceutical composition for inhibiting histone deacetylases, which is a preparation prepared from the compound or stereoisomers, pharmaceutically acceptable salts, crystal forms, solvates or isotopologues thereof as an active ingredient, and pharmaceutically acceptable adjuvants or auxiliary ingredients.

Further, the preparation is an oral preparation, a sublingual preparation, a buccal preparation, a transdermal absorption preparation or an injectable preparation.

The present invention prepares the following compounds having excellent inhibition activity against histone deacetylases, referring to Table 1:

TABLE 1

Compounds prepared by the present invention

| Number | Structure | Name |
|---|---|---|
| 1 | 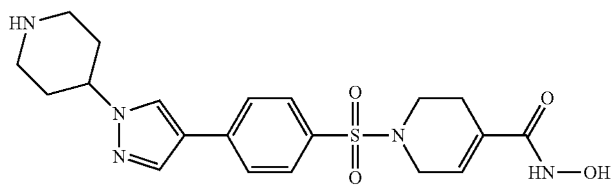 [SMILES: O=C(NO)C1=CCN(S(=O)(=O)c2ccc(-c3cnn(C4CCNCC4)c3)cc2)CC1] | N-hydroxyl-1-((4-(1-(piperidine-4-yl)-1H-pyrazol-4-yl)phenyl)sulfonyl)-1,2,3,6-tetrahydropyridine-4-formamide |
| 2 | 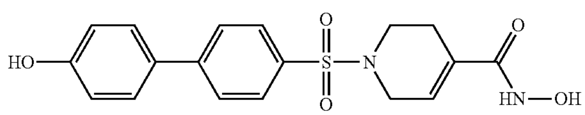 [SMILES: O=C(NO)C1=CCN(S(=O)(=O)c2ccc(-c3ccc(O)cc3)cc2)CC1] | N-hydroxyl-1-((4'-hydroxyl-[1,1'-biphenyl]-4-yl)sulfonyl)-1,2,3,6-tetrahydropyridine-4-formamide |
| 3 | 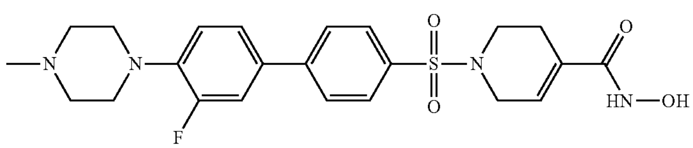 | N-hydroxyl-1-((3'-fluoro-4'-(4-methylpiperazine-1-yl)-[1,1'-biphenyl]-4-yl)sulfonyl)-1,2,3,6-tetrahydropyridine-4-formamide |
| 4 | 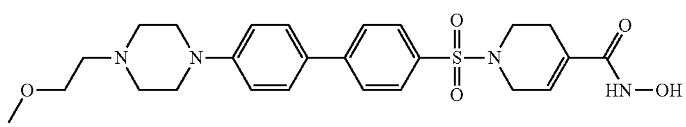 [SMILES: COCCN1CCN(c2ccc(-c3ccc(S(=O)(=O)N4CC=C(C(=O)NO)CC4)cc3)cc2)CC1] | N-hydroxyl-1-((4'-(4-(2-methoxyethyl)piperazine-1-yl)-[1,1'-biphenyl]-4-yl)sulfonyl)-1,2,3,6-tetrahydropyridine-4-formamide |
| 5 | 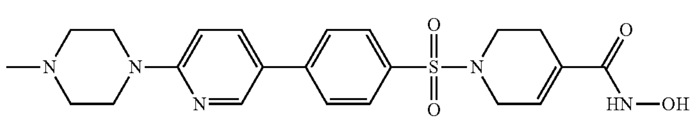 [SMILES: CN1CCN(c2ccc(-c3ccc(S(=O)(=O)N4CC=C(C(=O)NO)CC4)cc3)cn2)CC1] | N-hydroxyl-1-(4-(6-(4-methylpiperazine-1-yl)pyridine-3-yl)phenyl)sulfonyl)-1,2,3,6-tetrahydropyridine-4-formamide |
| 6 | 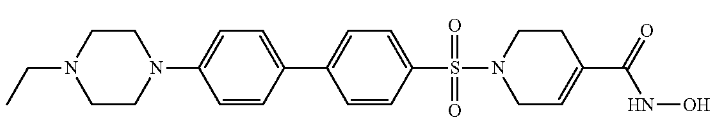 [SMILES: CCN1CCN(c2ccc(-c3ccc(S(=O)(=O)N4CC=C(C(=O)NO)CC4)cc3)cc2)CC1] | N-hydroxyl-1-(4'-(4-ethylpiperazine-1-yl)-[1,1'-biphenyl]-4-yl)sulfonyl)-1,2,3,6-tetrahydropyridine-4-formamide |
| 7 | 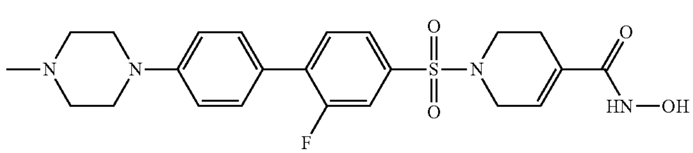 [SMILES: CN1CCN(c2ccc(-c3ccc(S(=O)(=O)N4CC=C(C(=O)NO)CC4)cc3F)cc2)CC1] | N-hydroxyl-1-((2-fluoro-4'-(4-methylpiperazine-1-yl)-[1,1'-biphenyl]-4-yl)sulfonyl)-1,2,3,6-tetrahydropyridine-4-formamide |
| 8 | 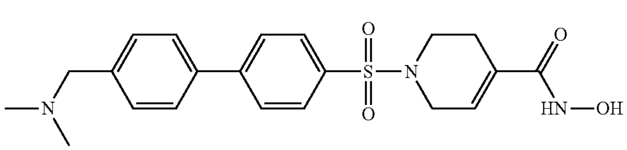 [SMILES: CN(C)Cc1ccc(-c2ccc(S(=O)(=O)N3CC=C(C(=O)NO)CC3)cc2)cc1] | N-hydroxyl-1((4'-((dimethylamino)methyl)-[1,1'-biphenyl]-4-yl)sulfonyl)-1,2,3,6-tetrahydropyridine-4-formamide |

TABLE 1-continued

Compounds prepared by the present invention

| Number | Structure | Name |
|---|---|---|
| 9 | 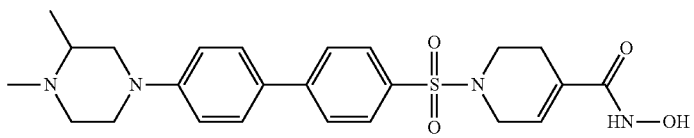 [SMILES: CC1CN(c2ccc(-c3ccc(S(=O)(=O)N4CC=C(C(=O)NO)CC4)cc3)cc2)CCN1C] | N-hydroxyl-1-((4'-(3,4'-dimethylpiperazine-1-yl)-[1,1'-biphenyl]-4-yl)sulfonyl)-1,2,3,6-tetrahydropyridine-4-formamide |
| 10 | 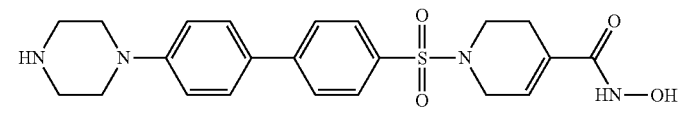 [SMILES: O=C(NO)C1=CCN(S(=O)(=O)c2ccc(-c3ccc(N4CCNCC4)cc3)cc2)CC1] | N-hydroxyl-1-((4'-(piperazine-1-yl)-[1,1'-biphenyl]-4-yl)sulfonyl)-1,2,3,6-tetrahydropyridine-4-formamide |
| 11 | 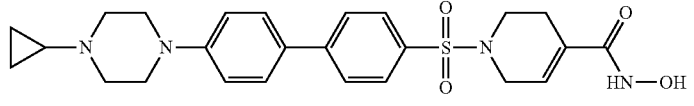 [SMILES: O=C(NO)C1=CCN(S(=O)(=O)c2ccc(-c3ccc(N4CCN(C5CC5)CC4)cc3)cc2)CC1] | N-hydroxyl-1-((4'-(4-cyclopropylpiperazine-1-yl)-[1,1'-biphenyl]-4-yl)sulfonyl)-1,2,3,6-tetrahydropyridine-4-formamide |
| 12 | 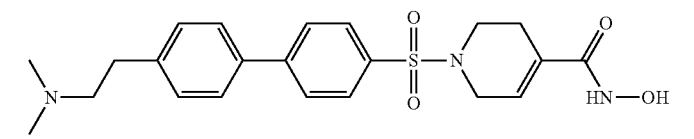 [SMILES: CN(C)CCc1ccc(-c2ccc(S(=O)(=O)N3CC=C(C(=O)NO)CC3)cc2)cc1] | N-hydroxyl-1-((4'-(2-(dimethylamino)ethyl)-[1,1'-biphenyl]-4-yl)sulfonyl)-1,2,3,6-tetrahydropyridine-4-formamide |
| 13 | 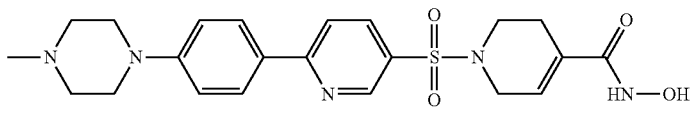 | N-hydroxyl-1-((6-(4-(4-methylpiperazine-1-yl)phenyl)pyridine-3-yl)sulfonyl)-1,2,3,6-tetrahydropyridine-4-formamide |
| 14 | 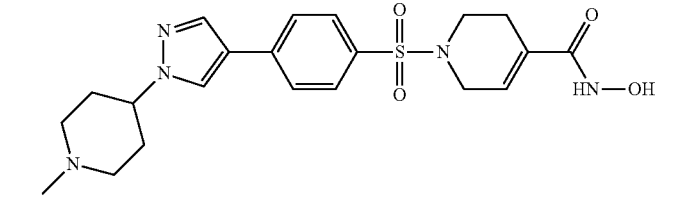 [SMILES: CN1CCC(n2cc(-c3ccc(S(=O)(=O)N4CC=C(C(=O)NO)CC4)cc3)cn2)CC1] | N-hydroxyl-1-((4-(1-(1-methylpiperidine-4-yl)-1H-pyrazol-4-yl)phenyl)sulfonyl)-1,2,3,6-tetrahydropyridine-4-formamide |
| 15 | 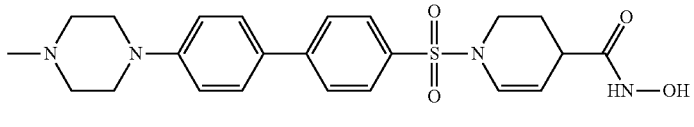 | N-hydroxyl-1-((4'-(4-methylpiperazine-1-yl)-[1,1'-biphenyl]-4-yl)sulfonyl)-1,2,3,4-tetrahydropyridine-4-formamide |
| 16 | 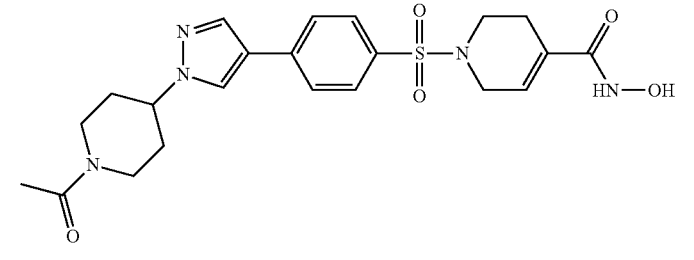 [SMILES: CC(=O)N1CCC(n2cc(-c3ccc(S(=O)(=O)N4CC=C(C(=O)NO)CC4)cc3)cn2)CC1] | N-hydroxyl-1-((4-(1-acetylpiperidine-4-yl)-1H-pyrazol-4-yl)phenyl)sulfonyl)-1,2,3,6-tetrahydropyridine-4-formamide |
| 17 | 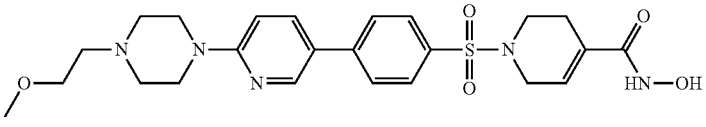 [SMILES: COCCN1CCN(c2ccc(-c3ccc(S(=O)(=O)N4CC=C(C(=O)NO)CC4)cc3)cn2)CC1] | N-hydroxyl-1-((4-(6-(4-(2-methoxyethyl)piperazine-1-yl)pyridine-3-yl)phenyl)sulfonyl)-1,2,3,6-tetrahydropyridine-4-formamide |

TABLE 1-continued

Compounds prepared by the present invention

| Number | Structure | Name |
|---|---|---|
| 18 | 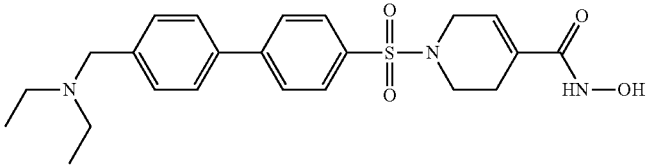 | N-hydroxyl-1-((4'-((diethylamino)methyl)-[1,1'-biphenyl]-4-yl)sulfonyl)-1,2,3,6-tetrahydropyridine-4-formamide |
| 19 | 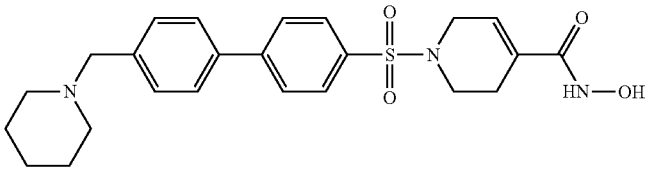 [SMILES: O=C(NO)C1=CCN(S(=O)(=O)c2ccc(-c3ccc(CN4CCCCC4)cc3)cc2)CC1] | N-hydroxyl-1-((4'-(piperidine-1-ylmethyl)-[1,1'-biphenyl]-4-yl)sulfonyl)-1,2,3,6-tetrahydropyridine-4-formamide |
| 20 | 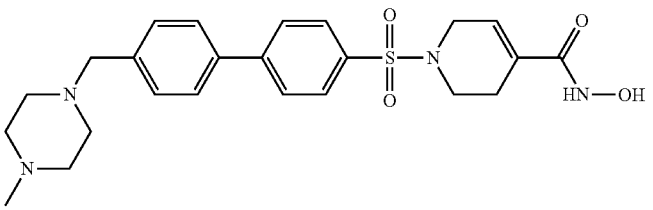 [SMILES: CN1CCN(Cc2ccc(-c3ccc(S(=O)(=O)N4CC=C(C(=O)NO)CC4)cc3)cc2)CC1] | N-hydroxyl-1-((4'-((4-methylpiperazine-1-yl)methyl)-[1,1'-biphenyl]-4-yl)sulfonyl)-1,2,3,6-tetrahydropyridazole-4-formamide |
| 21 | 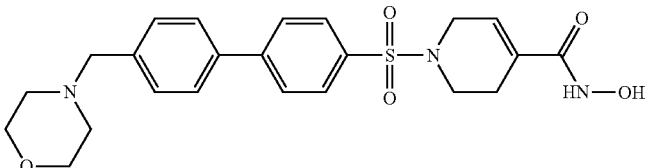 | N-hydroxyl-1-((4'-(morpholinylmethyl)-[1,1'-biphenyl]-4-yl)sulfonyl)-1,2,3,6-tetrahydropyridine-4-formamide |
| 22 | 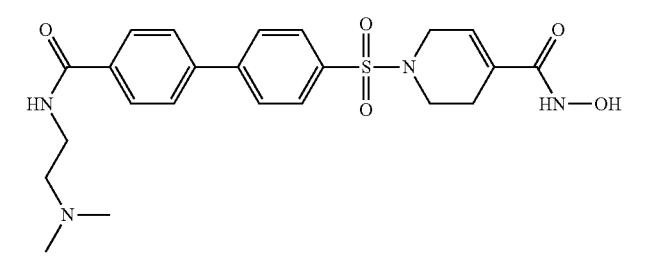 [SMILES: CN(C)CCNC(=O)c1ccc(-c2ccc(S(=O)(=O)N3CC=C(C(=O)NO)CC3)cc2)cc1] | N-hydroxyl-1-((4'-((2-(dimethylamino)ethyl)aminoformyl)-[1,1'-biphenyl]-4-yl)sulfonyl)-1,2,3,6-tetrahydropyridine-4-formamide |
| 23 | 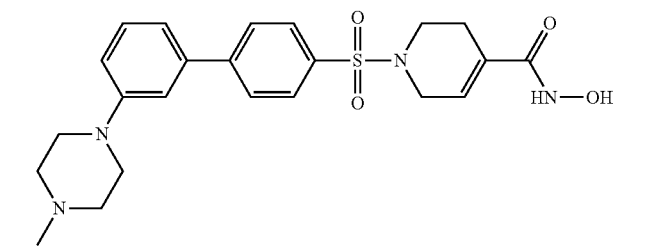 [SMILES: CN1CCN(c2cccc(-c3ccc(S(=O)(=O)N4CC=C(C(=O)NO)CC4)cc3)c2)CC1] | N-hydroxyl-1-((3'-(4-methylpiperazine-1-yl)-[1,1'-biphenyl]-4-yl)sulfonyl)-1,2,3,6-tetrahydropyridine-4-formamide |
| 24 | 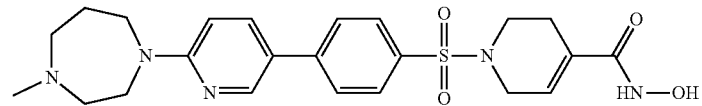 [SMILES: CN1CCCN(c2ccc(-c3ccc(S(=O)(=O)N4CC=C(C(=O)NO)CC4)cc3)cn2)CC1] | N-hydroxyl-1-((4-(6-(4-methyl-1,4-diazaheptane-1-yl)pyridine-3-yl)phenyl)sulfonyl)-1,2,3,6-tetrahydropyridine-4-formamide |

TABLE 1-continued

Compounds prepared by the present invention

| Number | Structure | Name |
|---|---|---|
| 25 | 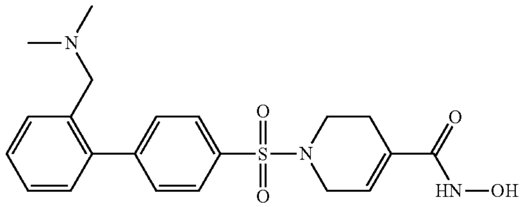 [SMILES: CN(C)Cc1ccccc1-c1ccc(S(=O)(=O)N2CC=C(C(=O)NO)CC2)cc1] | N-hydroxyl-1-((2'-((dimethylamino)methyl-[1,1'-biphenyl]-4-yl)sulfonyl)-1,2,3,6-tetrahydropyridine-4-formamide |
| 26 | 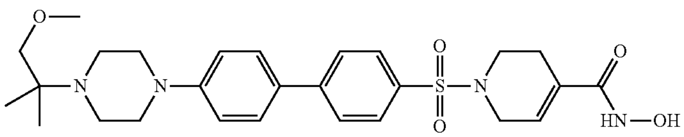 [SMILES: COCC(C)(C)N1CCN(c2ccc(-c3ccc(S(=O)(=O)N4CC=C(C(=O)NO)CC4)cc3)cc2)CC1] | N-hydroxyl-1-(((4'-(4-(1-methoxy-2-methylpropane-2-yl)piperazine-1-yl)-[1,1'-biphenyl]-4-yl)sulfonyl)-1,2,3,6-tetrahydropyridine-4-formamide |
| 27 | 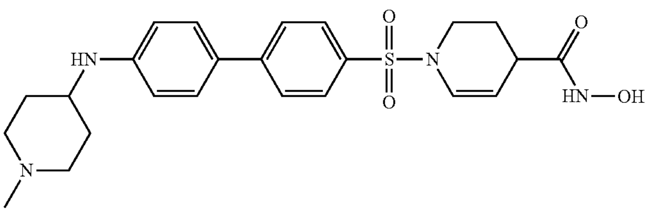 [SMILES: CN1CCC(Nc2ccc(-c3ccc(S(=O)(=O)N4C=CC(C(=O)NO)CC4)cc3)cc2)CC1] | N-hydroxyl-1-((4'-((methylpiperidine-4-yl)amino)-[1,1'-biphenyl]-4-yl)sulfonyl)-1,2,3,6-tetrahydropyridine-4-formamide |
| 28 | 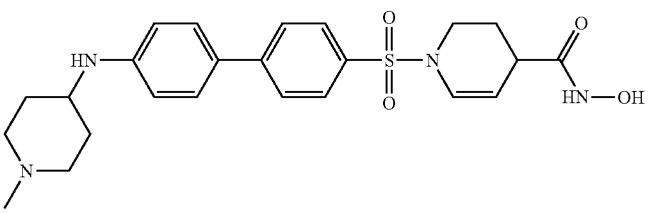 [SMILES: CN1CCC(Nc2ccc(-c3ccc(S(=O)(=O)N4C=CC(C(=O)NO)CC4)cc3)cc2)CC1] | N-hydroxyl-1-((4'-((methylpiperidine-4-yl)amino)-[1,1'-biphenyl]-4-yl)sulfonyl)-1,2,3,4-tetrahydropyridine-4-formamide |
| 29 | 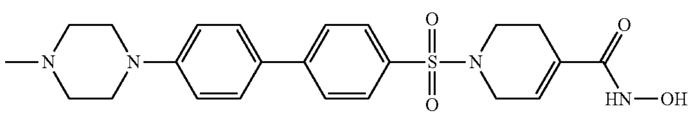 | N-hydroxyl-1-((4'-(4-methylpiperazinyl)-[1,1'-biphenyl]-4-yl)sulfonyl)-1,2,3,6-tetrahydropyridine-4-formamide |
| 30 | 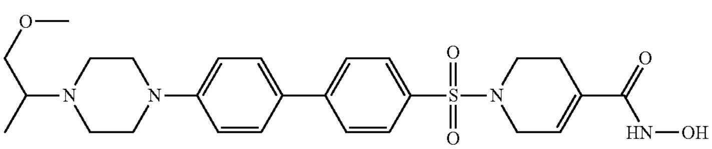 [SMILES: COCC(C)N1CCN(c2ccc(-c3ccc(S(=O)(=O)N4CC=C(C(=O)NO)CC4)cc3)cc2)CC1] | N-hydroxyl-1-((4'-(4-(1-methoxyisopropyl)piperazinyl)-[1,1'-biphenyl]-4-yl)sulfonyl)-1,2,3,6-tetrahydropyridine-4-formamide |
| 31 | 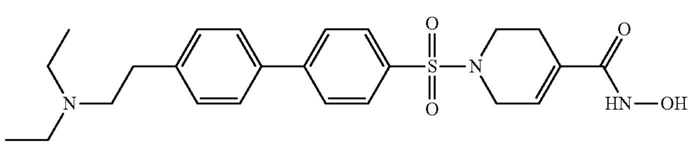 [SMILES: CCN(CC)CCc1ccc(-c2ccc(S(=O)(=O)N3CC=C(C(=O)NO)CC3)cc2)cc1] | N-hydroxyl-1-((4'-(2-(diethylamino)ethyl)-[1,1'-biphenyl]-4-yl)sulfonyl)-1,2,3,6-tetrahydropyridine-4-formamide |
| 32 | 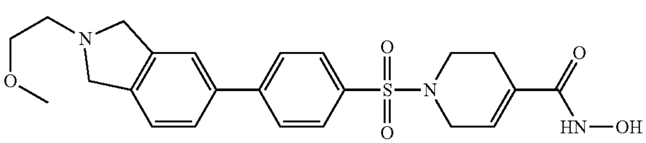 [SMILES: COCCN1Cc2ccc(-c3ccc(S(=O)(=O)N4CC=C(C(=O)NO)CC4)cc3)cc2C1] | N-hydroxyl-1-((4-(2-(2-methoxyethyl)isoindoline-5-yl)phenyl)sulfonyl)-1,2,3,6-tetrahydropyridine-4-formamide |
| 33 | 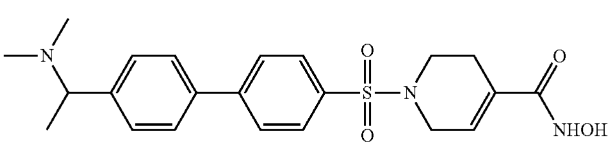 | 1-((4'-(1-(dimethylamino)ethyl)-[1,1'-biphenyl]-4-yl)sulfonyl)-N-hydroxyl-1,2,3,6-tetrahydropyridine-4-formamide |

TABLE 1-continued

Compounds prepared by the present invention

| Number | Structure | Name |
|---|---|---|
| 34 | 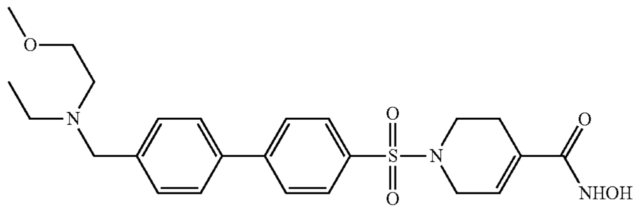 | 1-((4'-((4-(ethyl(2-methoxyethyl)amino)methyl)-[1,1'-biphenyl]-4-yl)sulfonyl)-N-hydroxyl-1,2,3,6-tetrahydropyridine-4-formamide |
| 35 | 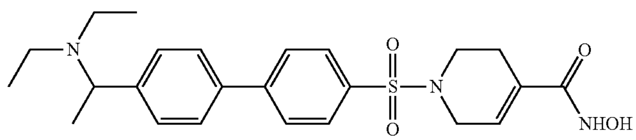 | 1-((4'-(1-(diethylamino)ethyl)-[1,1'-biphenyl]-4-yl)sulfonyl)-N-hydroxyl-1,2,3,6-tetrahydropyridine-4-formamide |
| 36 | 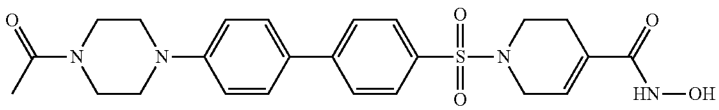 [SMILES: CC(=O)N1CCN(c2ccc(-c3ccc(S(=O)(=O)N4CC=C(C(=O)NO)CC4)cc3)cc2)CC1] | 1-((4'-(acetylpiperazine-1-yl)-[1,1'-biphenyl]-4-yl)sulfonyl)-N-hydroxyl-1,2,3,6-tetrahydropyridine-4-formamide |
| 37 | 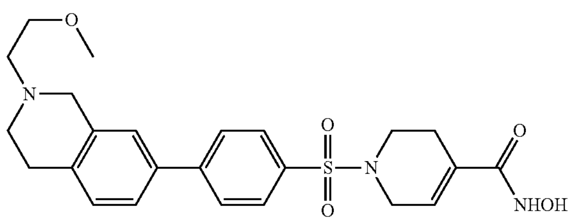 | N-hydroxyl-1-((4-(2-(2-methoxyethyl)-1,2,3,4-tetrahydroisoquinoline-7-yl)phenyl)sulfonyl)-1,2,3,6-tetrahydropyridine-4-formamide |
| 38 | 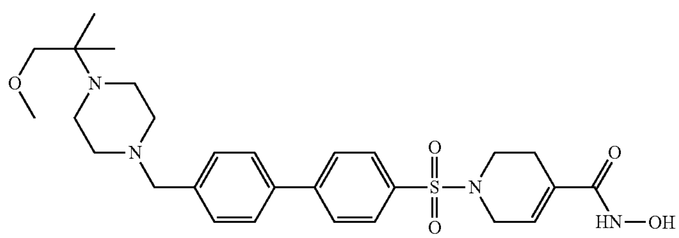 [SMILES: COCC(C)(C)N1CCN(Cc2ccc(-c3ccc(S(=O)(=O)N4CC=C(C(=O)NO)CC4)cc3)cc2)CC1] | N-hydroxyl-1-((4'-((4-(1-methoxy-2-methylpropane-2-yl)piperazine-1-yl)methyl)-[1,1'-biphenyl]-4-yl)sulfonyl)-1,2,3,6-tetrahydropyridine-4-formamide |
| 39 | 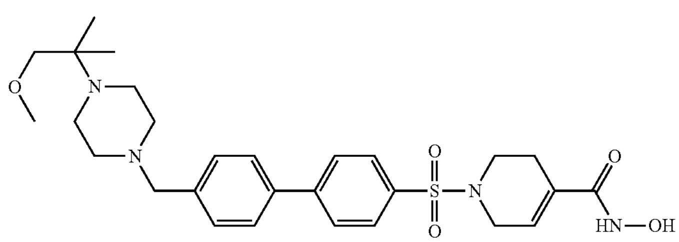 [SMILES: COCC(C)(C)N1CCN(Cc2ccc(-c3ccc(S(=O)(=O)N4CC=C(C(=O)NO)CC4)cc3)cc2)CC1] | N-hydroxyl-1-((4'-((4-(1-methoxy-2-methylpropane-2-yl)piperazine-1-yl)methyl)-[1,1'-biphenyl]-4-yl)sulfonyl)-1,2,3,4-tetrahydropyridine-4-formamide |
| 40 | 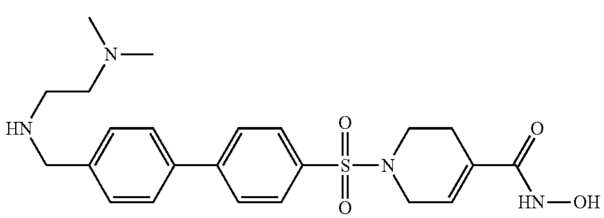 [SMILES: CN(C)CCNCc1ccc(-c2ccc(S(=O)(=O)N3CC=C(C(=O)NO)CC3)cc2)cc1] | N-hydroxyl-1-((4'-(((2-(dimethylamino)ethyl)amino)methyl)-[1,1'-biphenyl]-4-yl)sulfonyl)-1,2,3,6-tetrahydropyridine-4-formamide |
| 41 | 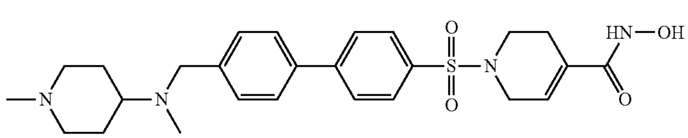 [SMILES: CN1CCC(N(C)Cc2ccc(-c3ccc(S(=O)(=O)N4CC=C(C(=O)NO)CC4)cc3)cc2)CC1] | N-hydroxyl-1-((4'-((methyl(1-methylpiperidine-4-yl)amino)methylene)-[1,1'-biphenyl]-4-yl)sulfonyl)-1,2,3,6-tetrahydropyridine-4-formamide |

TABLE 1-continued

Compounds prepared by the present invention

| Number | Structure | Name |
|---|---|---|
| 42 | 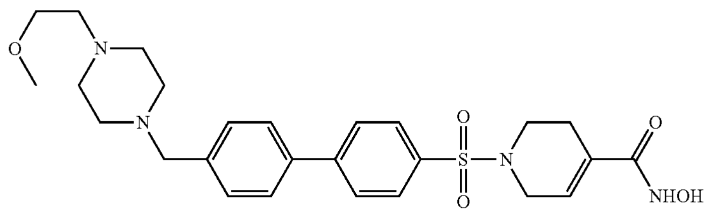 | N-hydroxyl-1-((4'-((4-(2-methoxyethyl)-1-piperazinyl)methyl)-[1,1'-biphenyl]-4-yl)sulfonyl)-1,2,3,6-tetrahydropyridine-4-formamide |
| 43 | 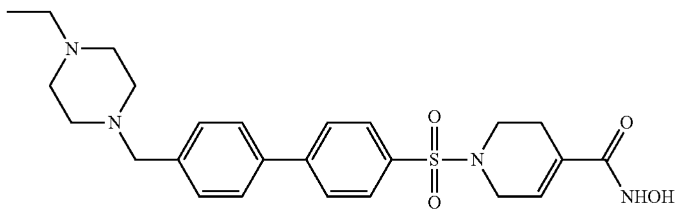 | 1-((4'-((4-ethylpiperazine-1-yl)methyl)-[1,1'-biphenyl]-4-yl)sulfonyl)-N-hydroxyl-1,2,3,6-tetrahydropyridine-4-formamide |
| 44 | 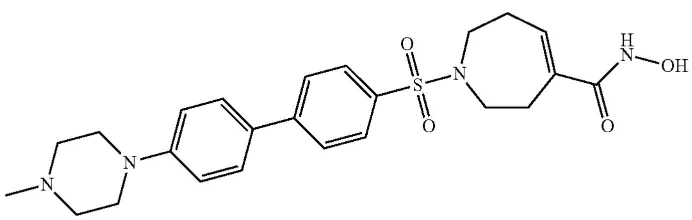 [SMILES: CN1CCN(c2ccc(-c3ccc(S(=O)(=O)N4CCC=C(C(=O)NO)CC4)cc3)cc2)CC1] | N-hydroxyl-1-((4'-(4-methylpiperazine-1-yl)-[1,1'-biphenyl]-4-yl)sulfonyl)-2,3,6,7-tetrahydro-1H-aza-4-formamide |

The compounds and derivatives provided in the present invention can be named according to the naming system of the IUPAC (International Union of Pure and Applied Chemistry) or CAS (Chemical Abstracts, Columbus, Ohio).

For the definitions of the terms used herein, unless otherwise stated, the initial definition of a group or a term used herein is applicable to this group or this term throughout the description. For the terms that are not specifically defined herein, their meanings should be given by those skilled in the art according to the disclosed content and the context.

The "substitution" means that hydrogen atoms in a molecule are substituted with other different atoms or molecules.

The minimum value and the maximum value of the number of carbon atoms in a hydrocarbon group are expressed by a prefix. For example, the alkyl having a prefix of Ca-Cb indicates any alkyl containing a to b carbon atoms. Therefore, for example, the $C_1$-$C_4$ alkyl means alkyl containing 1 to 4 carbon atoms; and, the substituted $C_1$-$C_6$ alkyl means that alkyl contains 1 to 6 carbon atoms, excluding carbon atoms on a substituent group. The alkyl is a straight-chain or branched-chain saturated hydrocarbonyl group.

The term "heterocyclyl" refers to a group on a non-aromatic ring having heteroatoms, and this group may be saturated or partially unsaturated.

The term "pharmaceutically acceptable" means that a carrier, a carried substance, a diluent, an adjuvant and/or the formed salt is chemically or physically compatible with other components forming a certain dosage form and physiologically compatible with an acceptor.

The terms "salts" and "medicinal salts" refer to acidic salts and/or basic salts formed by the compounds or stereisomers thereof and inorganic and/or organic acid or base, including zwitterionic salts (inner salts) and quaternary ammonium salts, for example, alkylammonium salts. These salts may be directly obtained by final separation and purification of the compounds. These salts may also be obtained by mixing the compounds or stereisomers thereof with a proper amount (for example, equivalent amount) of acid or base. These salts may be collected by filtering precipitation in the solution, or obtained by evaporating the solvent and recycling, or obtained by reacting in an aqueous medium and then freeze-drying. The salts in the present invention may be hydrochloride, sulfate, citrate, benzenesulfonate, hydrobromide, hydrofluoride, phosphate, acetate, propionate, succinate, oxalate, malate, succinate, fumarate, maleate, tartrate or trifluoroacetate of the compounds.

The term "stereoisomer" has stereocenters (for example, C with four different substituent groups), axial asymmetry, for example, bond asymmetry and plane asymmetry, and mixtures thereof.

In some implementations of the present invention, the compounds of the present invention include isotope-labeled compounds. The isotope-labeled compounds are the same as the compounds listed herein, but one or more atoms are substituted by another atom and the atomic mass or mass number of this atom is different from the common atomic mass or mass number in natural world. Isotopes that can be introduced into the compounds shown in Formula (I) include hydrogen, carbon, nitrogen, oxygen and sulfur, i.e., $^2$H, $^3$H, $^{13}$C, $^{14}$C, $^{15}$N, $^{17}$O, $^{18}$O and $^{35}$S. The compounds containing the above isotopes and/or isotopes of other atoms and stereoisomers thereof as well as medicinal salts of the compounds and stereoisomers shall fall into the scope of the present invention.

The term "isotopologue" refers to any form of a compound in which at least one atom of the natural isotope abundance is replaced with an isotope enrichment form different from the natural abundance. Isotopologues may be based on the replacement of hydrogen with deuterium and/or tritium. Similarly, 12C of the natural abundance may be replaced with 13C or 14C; 14N of the natural abundance may be replaced with 15N; 16O of the natural abundance may be replaced with 17O or 18O; or, any combination of the above situations is possible. The isotopologue may include the replacement of any number of atoms in the compound with the isotope enrichment form. Any degree of isotope enrichment may be realized.

In the present invention, the method for separating and purifying key intermediates and compounds is the common separation and purification method in the organic chemistry, and examples of the method include filtration, extraction, drying, spin-drying and various types of chromatography. Optionally, intermediates may participate in the subsequent reaction, without purification.

In some implementations, one or multiple compounds of the present invention may be used together. It is possible that the compound of the present invention is used together with any other active reagents to prepare drugs or pharmaceutical compositions for regulating cell functions or treating diseases. If a group of compounds are used, these compounds may be administrated on a subject simultaneously, separately or sequentially.

The administration method of the compound or pharmaceutical composition of the present invention is not specifically limited, and the representative administration method includes (not limited to): oral administration, parenteral (intravenous, intramuscular or subcutaneous) administration and topical administration.

The solid dosage form for oral administration includes capsule, tablet, pill, powder and granule. In the solid dosage form, the active compound is mixed with at least one conventional inert excipient (or carrier), for example, sodium citrate or dicalcium phosphate, or mixed with the following components: (a) a filler or compatibilizer, for example, starch, lactose, sucrose, glucose, mannitol and silicic acid; (b) a binder, for example, hydroxymethyl cellulose, alginate, gelatin, polyvinyl pyrrolidone, sucrose and Arabic gum; (c) a moisturizer, for example, glycerol; (d) a disintegrant, for example, agar, calcium carbonate, potato starch or cassava starch, alginic acid, some composite silicates, and sodium carbonate; (e) a solution retardant, for example, paraffin; (f) an absorption accelerator, for example, quaternary ammonium compounds; (g) a wetting agent, for example, spermol and glyceryl monostearate; (h), an adsorbent, for example, kaolin; and, (i) a lubricant, for example, talcum, calcium stearate, magnesium stearate, solid polyethylene glycol, sodium dodecyl sulfate or mixtures thereof. In the capsules, tablets and pills, the dosage form may also contain a buffer.

The solid dosage form such as the tablet, sugared pill, capsule, pill and granule may be prepared from a coating and a shell material, for example, casing and other known materials in the art. An opacifying agent may be contained, and the active compound in the composition or the compound may be released in a certain part of the digestive duct in a deferred manner. Examples of available inclusion components include polymers and waxy substances. If necessary, the active compound may also form microcapsules with one or more of the above excipients.

The liquid dosage form for oral administration includes pharmaceutically acceptable emulsion, solution, suspension, syrup or tincture. In addition to the active compound, the liquid dosage form may include an inert diluent commonly used in the art (e.g., water or other solvents), a solubilizer and an emulsifier, for example, ethanol, isopropanol, ethyl carbonate, ethyl acetate, propanediol, 1,3-butanediol, dimethylformamide and oil, particularly cottonseed oil, peanut oil, maize embryo oil, olive oil, castor oil, sesame oil or a mixture thereof, and the like.

In addition to the inert diluent, the composition may further contain an auxiliary agent, for example, a wetting agent, an emulsifier, a suspending agent, a sweetening agent, a corrigent and a spice.

In addition to the active compound, the suspension may further contain a suspending agent, for example, ethoxylated isooctadecane, polyoxyethylene sorbitol, isosorbide dinitrate, microcrystalline cellulose, aluminum methoxide, agar, mixtures thereof and the like.

The composition for parenteral injection may include physiologically acceptable sterile aqueous or anhydrous solution, dispersion liquid, suspension or emulsion, and sterile power that is re-dissolved to form sterile injectable solution or dispersion liquid. The proper aqueous or anhydrous carrier, diluent, solvent or excipient includes water, ethanol, polyalcohol and a proper mixture thereof.

The dosage form of the compound of the present invention suitable for topical administration includes ointment, powder, patch, spray and inhalation. The active ingredient is mixed with a physiologically acceptable carrier and any preservative and buffer, or mixed with possibly needed propellant if necessary.

In the present invention, the pharmaceutically acceptable adjuvants refer to substances contained in the dosage form in addition to the active ingredient.

In the present invention, the pharmaceutically acceptable auxiliary ingredients have a certain physiological activity, but will not change the leading role of the pharmaceutical composition in the disease treatment process and merely show auxiliary effects. These auxiliary effects merely make use of the known activities of these ingredients. The addition of the auxiliary ingredients is a common adjuvant treatment method in the medical field. If the auxiliary ingredients are used together with the pharmaceutical composition of the present invention, the auxiliary ingredients shall fall into the protection scope of the present invention.

The compound of the present invention has the activities of inducing differentiation, regulating immunity, impeding the cell cycle and facilitating cell apoptosis and excellent HDAC subtype selectivity, and is aimed at having better curative effects on various cancers and overcoming the toxic and side effects of the existing HDAC inhibitors, for example, anemia, ischemic stroke, deep venous thrombosis, thrombocytopenia, emesis and the like.

The compound having a novel structure provided by the present invention shows excellent inhibition activity against histone deacetylases, has remarkable inhibition effects on cancer cells, and provides a new choice of drugs used for the clinic treatment and diseases related to the abnormal activity of histone deacetylases.

Apparently, without departing from the basic technical concept of the present invention, other modifications, replacements or alterations in various forms may be made to the contents of the present invention in accordance with the common technical knowledge and common means in the art.

The contents of the present invention will be further described below in detail by specific implementations in form of embodiments. The scope of the theme should not be regarded as being limited to the following examples. All techniques realized based on the contents of the present invention shall fall into the scope of the present invention.

DETAILED DESCRIPTION OF THE PRESENT INVENTION

All raw materials and facilities used in the specific implementations of the present invention are known products and commercially available products.

Embodiment 1: Preparation of N-hydroxyl-1-((4-(1-(piperidine-4-yl)-1H-pyrazol-4-yl)phenyl)sulfonyl)-1,2,3,6-tetrahydropyridine-4-formamide

1. Preparation of ethyl 1,2,3,6-tetrahydropyridine-4-formate

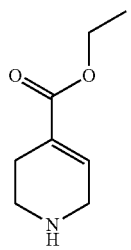

Ethyl N-t-butyloxycarboryl-1,2,3,6-tetrahydropyridine-4-formate (10.0 g, 39.2 mmol, produced by Nanjing Ailikaide Chemical Co., Ltd.) was dissolved in 50.0 mL of dichloromethane solution in an ice bath, then added dropwise with 50.0 mL of trifluoroacetic acid and stirred. The mixture was slowly heated to the room temperature and then continuously stirred for 2 h. Subsequently, the reaction solution was condensed to obtain yellow oily ethyl 1,2,3,6-tetrahydropyridine-4-formate (5.80 g, 37.4 mmol, 96% yield).

MS (ESI) m/z 156 (M+1)+.

2. Preparation of ethyl 1-((4-bromophenyl)sulfonyl)-1,2,3,6-tetrahydropyridine-4-formate

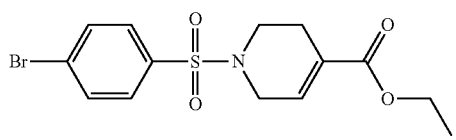 [SMILES: CCOC(=O)C1=CCN(S(=O)(=O)c2ccc(Br)cc2)CC1]

Ethyl 1,2,3,6-tetrahydropyridine-4-formate (2.00 g, 5.40 mmol) and triethylamine (1.09 g, 10.8 mmol) were dissolved in dichloromethane (20.0 ml), and 4-bromophenyl-1-sulfonylchloride (1.38 g, 5.40 mmol) was added in the reaction solution at the room temperature. The reaction solution was stirred for 2 h at the room temperature and condensed to remove the solvent, and the crude product was purified by column chromatography to obtain white solid ethyl 1-((4-bromophenyl)sulfonyl)-1,2,3,6-tetrahydropyridine-4-formate (1.51 g, 4.05 mmol, 75% yield).

MS (ESI) m/z 374 (M+1)+.

3. Preparation of ethyl 1-((4-(1-(piperidine-4-yl)-1H-pyrazol-4-yl)phenyl)sulfonyl)-1,2,3,6-tetrahydropyridine-4-formate

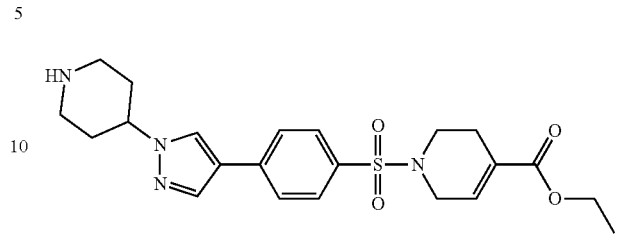

Ethyl 1-((4-bromophenyl)sulfonyl)-1,2,3,6-tetrahydropyridine-4-formate (500 mg, 1.34 mmol), tert-butyl 4-[4-(4,4,5,5-tetramethyl-1,3,2-dioxocyclopentaborane-2-yl)-1H-pyrazol-1-yl]piperidine-1-formate (506 mg, 1.34 mmol, produced by Nanjing Ailikaide Chemical Co., Ltd.), [1,1'-bis(diphenylphosphino)ferrocene]palladium dichloride (49.0 mg, 67.0 μmol) and sodium carbonate (284 mg, 2.68 mmol) were dissolved in N,N-dimethylformamide (12.0 ml). Under the atmosphere of nitrogen, the reaction solution was heated to 80° C. and stirred overnight. At the end of reaction, the reaction solution was condensed to remove the solvent. The crude product was dissolved in water (40.0 ml) and extracted with ethyl acetate (40.0 ml×3). The organic phases were combined, then condensed to remove the solvent and purified by column chromatography to obtain white solid. The white solid was dissolved in dichloromethane (3.00 ml) and then added dropwise with trifluoroacetic acid (3.00 ml) in an ice bath. After the dropwise addition is completed, the reaction system was heated to the room temperature and reacted for 1 h, and condensed at a reduced pressure to remove the solvent to obtain ethyl 1-((4-(1-(piperidine-4-yl)-1H-pyrazol-4-yl)phenyl)sulfonyl)-1,2,3,6-tetrahydropyridine-4-formate (202 mg, 456 μmol, 34% yield).

MS (ESI) m/z 445 (M+1)+.

4. Preparation of N-hydroxyl-1-((4-(1-(piperidine-4-yl)-1H-pyrazol-4-yl)phenyl)sulfonyl)-1,2,3,6-tetrahydropyridine-4-formamide

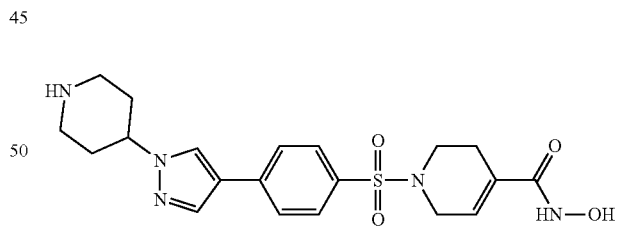

Ethyl 1-((4-(1-(piperidine-4-yl)-1H-pyrazol-4-yl)phenyl)sulfonyl)-1,2,3,6-tetrahydropyridine-4-formate (202 mg, 456 μmol) was dissolved in dichloromethane (3.00 ml) and methanol (3.00 ml), and then added with hydroxylamine aqueous solution (505, 2.00 mL) and NaOH (83.1 mg, 2.10 mmol) while stirring. The mixture was slowly heated to the room temperature and then continuously stirred for 2 h. The reaction system was condensed to remove the solvent, and the crude product was purified by preparative liquid chromatography to obtain white solid N-hydroxyl-1-((4-(1-(piperidine-4-yl)-1H-pyrazol-4-yl)phenyl)sulfonyl)-1,2,3,6-tetrahydropyridine-4-form amide (14.4 mg, 33.3 μmol, 7.3% yield).

MS (ESI) m/z 432 (M+1)+.

¹HNMR (400 MHz, DMSO) δ=8.44 (s, 1H), 8.31 (s, 1H), 8.06 (s, 1H), 7.86-7.84 (d, J=8.4 Hz, 2H), 7.75-7.73 (d, J=8.4 Hz, 2H), 6.35 (s, 1H), 4.39-4.37 (m, 1H), 3.64-3.63 (d, J=2.8 Hz, 2H), 3.23-3.21 (d, J=8.8 Hz, 2H), 2.87-2.83 (m, 2H), 2.29 (br, 2H), 2.10-2.09 (s, 2H), 2.02-1.97 (m, 2H).

Embodiment 2: Preparation of N-hydroxyl-1-((4'-hydroxyl-[1,1'-biphenyl]-4-yl)sulfonyl)-1,2,3,6-tetrahydropyridine-4-formamide

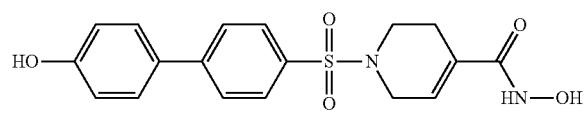

By using ethyl N-t-butyloxycarboryl-1,2,3,6-tetrahydropyridine-4-formate, 4-bromophenyl-1-sulfonylchloride and 4-hydroxyphenylboronic acid as raw materials, white solid N-hydroxyl-1-((4'-hydroxyl-[1,1'-biphenyl]-4-yl)sulfonyl)-1,2,3,6-tetrahydropyridine-4-formamide (3.4% total yield) was prepared by steps similar to those in Embodiment 1.

MS (ESI) m/z 375 (M+1)+.

¹HNMR (400 MHz, DMSO) δ=9.80 (s, 1H), 7.85-7.83 (m, 2H), 7.79-7.77 (m, 2H), 7.61-7.59 (d, J=8.7, 2H), 6.90-6.88 (d, J=8.6, 2H), 6.36 (s, 1H), 3.64-3.63 (d, J=2.6, 2H), 3.14-3.11 (t, J=5.6, 2H), 2.32-2.28 (m, 2H).

Embodiment 3: Preparation of N-hydroxyl-1-((3'-fluoro-4'-(4-methylpiperazine-1-yl)-[1,1'-biphenyl]-4-yl)sulfonyl)-1,2,3,6-tetrahydropyridine-4-formamide 1. Preparation of 1-(4-bromo-2-fluorophenyl)-4-methylpiperazine

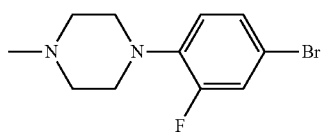

3-fluoro-4-(4-methylpiperazine-1-yl)aniline (2.00 g, 9.56 mmol) was dissolved in 5.00 ml of water in an ice bath, then added with 2.00 ml of solution of hydrobromic acid in acetic acid and sodium nitrite (663 mg, 10.5 mmol), stirred for half an hour, and added with cuprous bromide (4.11 g, 28.7 mmol). The reaction system was reacted for 2 h, then added with solid potassium carbonate to adjust the pH of the solution as 9 to 10, and extracted with dichloromethane (100 ml×5). The organic phases were combined, dried, condensed and purified by column chromatography to obtain brown oily 1-(4-bromo-2-fluorophenyl)-4-methylpiperazine (600 mg, 2.20 mmol, 23% yield).

MS (ESI) m/z 273 (M+1)+.

2. Preparation of 3-fluoro-4-(4-methylpiperazine-1-yl)-phenylboronic acid pinacol ester

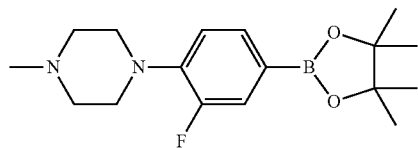

1-(4-bromo-2-fluorophenyl)-4-methylpiperazine (500 mg, 1.83 mmol) was dissolved in 1,4-dioxane (10.0 ml) at the room temperature, and added with potassium acetate (128 mg, 1.35 mmol), [1,1'-bis(diphenylphosphino)ferrocene]palladium dichloride (50.0 mg, 183 µmol) and bis(pinacolato)diboron (465 mg, 1.83 mmol). Nitrogen replacement was performed for three times, and the reaction system was heated to 90° C. and reacted for 2 h. The reaction solution was condensed and purified by column chromatography to obtain brown oily 3-fluoro-4-(4-methylpiperazine-1-yl)-phenylboronic acid pinacol ester (300 mg, 937 µmol, 51% yield).

3. Preparation of N-hydroxyl-1-((3'-fluoro-4'-(4-methylpiperazine-1-yl)-[1,1'-biphenyl]-4-yl)sulfonyl)-1,2,3,6-tetrahydropyridine-4-formamide

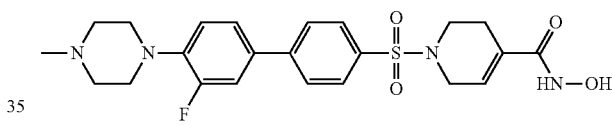

By using ethyl N-t-butyloxycarboryl-1,2,3,6-tetrahydropyridine-4-formate (10.0 g, 39.2 mmol), 4-bromophenyl-1-sulfonylchloride (1.38 g, 5.40 mmol) and 3-fluoro-4-(4-methylpiperazine-1-yl)-phenylboronic acid pinacol ester (319 mg, 1.34 mmol) as raw materials, white solid N-hydroxyl-1-((3'-fluoro-4'-(4-methylpiperazine-1-yl)-[1,1'-biphenyl]-4-yl)sulfonyl)-1,2,3,6-tetrahydropyridine-4-formamide (22.2 mg, 46.9 µmol, 3.5% total yield) was prepared by steps similar to those in Embodiment 1.

MS (ESI) m/z 475 (M+1)+.

¹HNMR (400 MHz, DMSO) δ=8.25 (s, 1H), 7.92 (d, J=7.6 Hz, 2H), 7.81 (d, J=8.8 Hz, 2H), 7.63-7.53 (m, 2H), 7.14 (t, J=8.8 Hz, 1H), 6.36 (s, 1H), 3.66 (s, 2H), 3.6-3.09 (m, 6H), 2.32 (s, 2H), 2.24 (s, 3H).

Embodiment 4: Preparation of N-hydroxyl-1-((4'-(4-(2-methoxyethyl)piperazine-1-yl)-[1,1'-biphenyl]-4-yl)sulfonyl)-1,2,3,6-tetrahydropyridine-4-formamide 1. Preparation of 4-(4-bromophenyl)benzenesulfonic acid

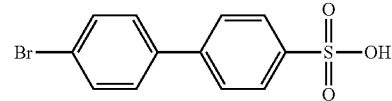 [SMILES: O=S(=O)(O)c1ccc(-c2ccc(Br)cc2)cc1]

4-bromobiphenyl (10.0 g, 42.9 mmol) was dissolved in dichloromethane (100 mL) in an ice bath, and then slowly added dropwise with chlorosulfonic acid (6.53 g, 55.8 mmol). The reaction system was heated to the room temperature and then reacted for 1 h. The reaction solution was filtered to obtain white solid 4-(4-bromophenyl)benzenesulfonic acid (11.5 g, 36.7 mmol, 86% yield).

2. Preparation of 4-(4-bromophenyl)benzenesulfonyl chloride

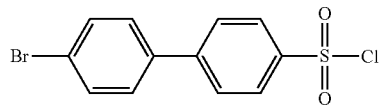 [SMILES: O=S(=O)(Cl)c1ccc(-c2ccc(Br)cc2)cc1]

4-(4-bromophenyl)benzenesulfonic acid (10.5 g, 33.5 mmol) was dissolved in thionyl chloride (60.0 mL). The reaction system was heated to 80° C. and then reacted for 4 h. The reaction solution was added dropwise in icy water (300 mL), and extracted with ethyl acetate (100 mL×2). The organic layer was dried with anhydrous sodium sulfate and condensed to obtain white solid 4-(4-bromophenyl)benzenesulfonyl chloride (11.5 g, 34.7 mmol, 100% yield).

3. Preparation of ethyl 1-(4-(4-bromophenyl)phenyl)sulfonyl-1,2,3,6-tetrahydropyridine-4-formate

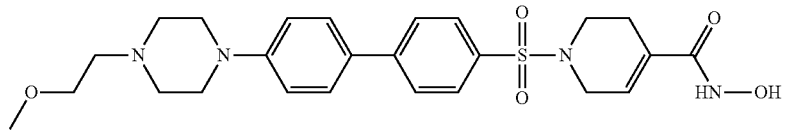

Ethyl 1,2,3,6-tetrahydropyridine-4-formate (5.38 g, 34.7 mmol) was dissolved in tetrahydrofuran (80.0 mL) and water (80.0 mL), and then added with solid sodium bicarbonate (11.9 g, 139 mmol) and 4-(4-bromophenyl)benzenesulfonyl chloride (11.5 g, 34.7 mmol). The reaction system was stirred and reacted for 1 h. The reaction solution was condensed, and extracted with ethyl acetate (100 mL×2). The organic layer was combined, dried with anhydrous sodium sulfate and condensed to obtain white solid ethyl 1-(4-(4-bromophenyl)phenyl)sulfonyl-1,2,3,6-tetrahydropyridine-4-formate (10.5 g, 13.3 mmol, 67% yield).

4. Preparation of ethyl 1-[4-[4-[4-(2-methoxyethyl)piperazine-1-yl]phenyl]phenyl]sulfony-1,2,3,6-tetrahydropyridine-4-formate

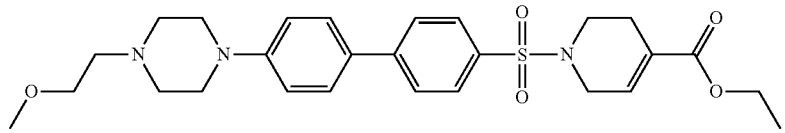 [SMILES: CCOC(=O)C1=CCN(S(=O)(=O)c2ccc(-c3ccc(N4CCN(CCOC)CC4)cc3)cc2)CC1]

Ethyl 1-(4-(4-bromophenyl)phenyl)sulfonyl-1,2,3,6-tetrahydropyridine-4-formate (3.00 g, 6.66 mmol) was dissolved in methylbenzene (30.0 mL), and added with solid cesium carbonate (3.25 g, 9.99 mmol), 2-dicyclohexylphosphonio-2,4,6-triisopropyl biphenyl (200 mg, 6.66 mmol), tris(dibenzylideneacetone)dipalladium (200 mg, 6.66 mmol) and 4-(2-methoxyethyl)piperazine (1.44 g, 9.99 mmol). The reaction system was heated to 100° C. and reacted for 4 h in the atmosphere of nitrogen. The reaction solution was filtered, and the filtrate was condensed and purified by column chromatography to obtain light yellow solid ethyl 1-[4-[4-[4-(2-methoxyethyl)piperazine-1-yl]phenyl]phenyl]sulfony-1,2,3,6-tetrahydropyridine-4-formate (2.50 g, 4.62 mmol, 69% yield).

5: Preparation of N-hydroxyl-1-((4'-(4-(2-methoxyethyl)piperazine-1-yl)-[1,1'-biphenyl]-4-yl)sulfonyl)-1,2,3,6-tetrahydropyridine-4-formamide Ethyl 1-[4-[4-[4-(2-methoxyethyl)piperazine-1-yl]phenyl]phenyl]sulfony-1,2,3,6-tetrahydropyridine-4-formate (2.00 g, 3.89 mmol) was dissolved in methanol (20.0 mL) and dichloromethane (20.0 mL), then added with hydroxylamine aqueous solution (6.19 g, 117 mmol), stirred for 10 min, and added with solid sodium hydroxide (779 mg, 19.5 mmol). The reaction system was reacted for 1.5 h at the room temperature. The reaction solution was added with 20 mL of water, and extracted with dichloromethane (50 ml×5). The organic phases were combined, dried, condensed and purified by column chromatography to obtain white solid N-hydroxyl-1-((4'-(4-(2-methoxyethyl)piperazine-1-yl)-[1,1'-biphenyl]-4-yl)sulfonyl)-1,2,3,6-tetrahydropyridine-4-formamide (800 mg, 1.60 mmol, 41.08% yield).

MS (ESI) m/z 502 (M+1)+.

$^1$HNMR (400 MHz, DMSO) δ=10.67 (br, 1H), 8.82 (br, 1H), 8.14 (s, 0.5H), 7.89-7.87 (m, 2H), 7.80-7.78 (m, 2H), 7.68-7.66 (m, 2H), 7.09 (d, J=8.8 Hz, 2H), 6.36 (s, 1H), 3.46 (s, 4H), 3.27 (s, 3H), 3.14-3.10 (m, 2H), 2.94-2.91 (m, 6H), 2.28 (s, 2H).

Embodiment 5: Preparation of N-hydroxyl-1-(4-(6-(4-methylpiperazine-1-yl)pyridine-3-yl)phenyl)sulfonyl)-1,2,3,6-tetrahydropyridine-4-formamide

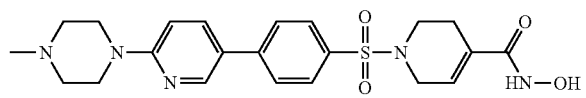

By using ethyl N-t-butyloxycarboryl-1,2,3,6-tetrahydropyridine-4-formate, 4-bromophenyl-1-sulfonylchloride and 2-(4-methylpiperazine-1-yl)pyridine-5-boronic acid pinacol ester (produced by Nanjing Ailikaide Chemical Co., Ltd.) as raw materials, white solid N-hydroxyl-1-(4-(6-(4-methylpiperazine-1-yl)pyridine-3-yl)phenyl)sulfonyl)-1,2, 3,6-tetrahydropyridine-4-formamide (18% total yield) was prepared by steps similar to those in Embodiment 1.

MS (ESI) m/z 458 (M+1)+.

¹HNMR (400 MHz, DMSO) δ=10.80 (br, 1H), 8.57 (d, J=2.4 Hz, 1H), 8.15 (s, 2H), 7.99 (d, J=2.8 Hz, 2H), 7.91 (d, J=9.2 Hz, 2H), 7.80 (d, J=8.8 Hz, 2H), 6.98 (d, J=8.8 Hz, 2H), 6.36 (s, 1H), 3.65 (s, 6H), 3.14 (t, J=1.6 Hz, 2H), 2.62-2.60 (m, 4H), 2.36-2.32 (m, 4H).

Embodiment 6: Preparation of N-hydroxyl-1-(4'-(4-ethylpiperazine-1-yl)-[1, t-biphenyl]-4-yl)sulfonyl)-1,2,3,6-tetrahydropyridine-4-formamide

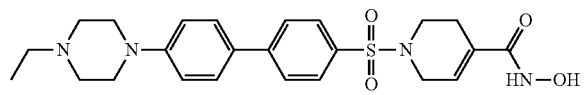 [SMILES: CCN1CCN(c2ccc(-c3ccc(S(=O)(=O)N4CC=C(C(=O)NO)CC4)cc3)cc2)CC1]

By using ethyl N-t-butyloxycarboryl-1,2,3,6-tetrahydropyridine-4-formate, 4-bromophenyl-1-sulfonylchloride and 1-((4'-4-methylethylpiperazine-1-yl)phenylboronic acid pinacol ester (produced by Shanghai Shuya Chemical Science and Technology Co., Ltd.) as raw materials, white solid N-hydroxyl-1-(4'-(4-ethylpiperazine-1-yl)-[1,1'-biphenyl]-4-yl)sulfonyl)-1,2,3,6-tetrahydropyridine-4-form amide (13% total yield) was prepared by steps similar to those in Embodiment 1.

MS (ESI) m/z 471 (M+1)+.

¹HNMR (400 MHz, DMSO) δ=10.67 (br, 1H), 8.82 (br, 1H), 8.15 (s, 1H), 7.88 (d, J=8.8 Hz, 2H), 7.80 (d, J=3.6 Hz, 2H), 7.67 (d, J=8.8 Hz, 2H), 7.10 (d, J=8.8 Hz, 2H), 6.37 (s, 1H), 3.64 (s, 2H), 3.40 (s, 4H), 3.12 (t, J=5.6 Hz, 2H), 3.03 (s, 4H), 2.88 (d, J=7.2 Hz, 2H), 2.28 (s, 2H), 1.18 (t, J=7.2 Hz, 2H).

Embodiment 7: Preparation of N-hydroxyl-1-((2-fluoro-4'-(4-methylpiperazine-1-yl)-[1,1'-biphenyl]-4-yl)sulfonyl)-1,2,3,6-tetrahydropyridine-4-formamide

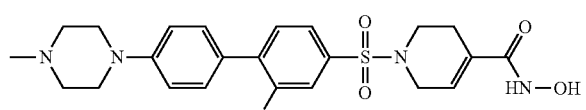

By using ethyl N-t-butyloxycarboryl-1,2,3,6-tetrahydropyridine-4-formate, 4-bromo-3-fluorophenyl-1-sulfonylchloride and (4-(4-methylpiperazine-1-yl)phenyl)boronic acid pinacol ester (produced by Shanghai Accela ChemBio Co., Ltd.) as raw materials, white solid N-hydroxyl-1-((2-fluoro-4'-(4-methylpiperazine-1-yl)-[1,1'-biphenyl]-4-yl)sulfonyl)-1,2,3,6-tetrahydropyridine-4-formamide (2.6% total yield) was prepared by steps similar to those in Embodiment 1.

MS (ESI) m/z 475 (M+1)+.

¹HNMR (400 MHz, DMSO) δ=10.63 (br, 1H), 8.75 (s, 1H), 7.77 (t, J=2 Hz, 1H), 7.64 (t, J=6 Hz, 2H), 7.53 (d, J=1.6 Hz, 2H), 7.51 (d, J=1.2 Hz, 2H), 7.08 (d, J=9.2 Hz, 2H), 6.38 (s, 1H), 3.70 (d, J=2.4 Hz, 2H), 3.37-3.20 (m, 4H), 3.20 (t, J=5.6 Hz, 2H), 2.64-2.63 (m, 4H), 2.35 (s, 3H), 2.34-2.32 (m, 2H).

Embodiment 8: Preparation of N-hydroxyl-1-((4'-((dimethylamino)methyl)-[1,1'-biphenyl]-4-yl)sulfonyl)-1,2,3,6-tetrahydropyridine-4-formamide

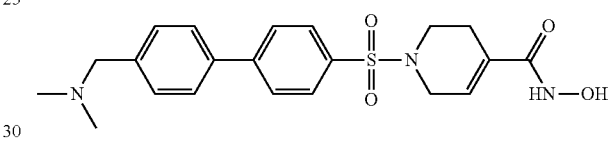

By using ethyl N-t-butyloxycarboryl-1,2,3,6-tetrahydropyridine-4-formate, 4-bromophenyl-1-sulfonylchloride and 4-(N,N-dimethylaminomethyl)phenylboronic acid pinacol ester (produced by J&K Scientific LTD.) as raw materials, white solid N-hydroxyl-1-((4'-((dimethylamino)methyl)-[1,1'-biphenyl]-4-yl)sulfonyl)-1,2,3,6-tetrahydropyridine-4-formamide (20.1% total yield) was prepared by steps similar to those in Embodiment 1.

MS (ESI) m/z 416 (M+1)+.

¹HNMR (400 MHz, DMSO) δ=8.27 (s, 1H), 7.93 (d, J=7.6 Hz, 2H), 7.85 (d, J=8.8 Hz, 2H), 7.76 (d, J=8.0 Hz, 2H), 7.52 (d, J=8.4 Hz, 2H), 6.33 (s, 1H), 3.67 (d, J=2.4 Hz, 2H), 3.14 (t, J=5.6 Hz, 2H), 2.44 (s, 6H), 2.27 (s, 2H).

Embodiment 9: Preparation of N-hydroxyl-1-((4'-(3,4-dimethylpiperazine-1-yl)-[1,1'-biphenyl]-4-yl)sulfonyl)-1,2,3,6-tetrahydropyridine-4-formamide

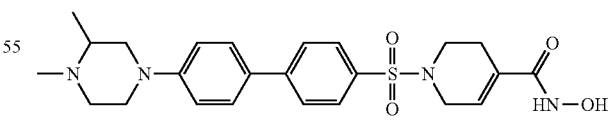

By using ethyl N-t-butyloxycarboryl-1,2,3,6-tetrahydropyridine-4-formate, 4-bromophenyl-1-sulfonylchloride and (4-(3,4-dimethylpiperazine-1-yl)phenyl)boronic acid (produced by Nanjing Ailikaide Chemical Co., Ltd.) as raw materials, white solid N-hydroxyl-1-((4'-(3,4-dimethylpiperazine-1-yl)-[1,1'-biphenyl]-4-yl)sulfonyl)-1,2,3,6-tetrahydropyridine-4-formamide (5.6% total yield) was prepared by steps similar to those in Embodiment 1.

MS (ESI) m/z 471 (M+1)+.

¹HNMR (400 MHz, DMSO) δ=8.21 (s, 1H), 7.85 (d, J=8.4 Hz, 2H), 7.77 (d, J=8.4 Hz, 2H), 7.64 (d, J=8.8 Hz, 2H), 7.06 (d, J=8.8 Hz, 2H), 6.33 (s, 1H), 3.72-3.64 (m, 4H), 3.12 (t, J=5.6 Hz, 2H), 2.61 (s, 3H), 2.42 (s, 3H), 2.28 (s, 2H), 1.16 (s, 3H).

Embodiment 10: Preparation of N-hydroxyl-1-((4'-(piperazine-1-yl)-[1, t-biphenyl]-4-yl)sulfonyl)-1,2,3,6-tetrahydropyridine-4-formamide

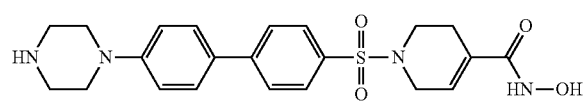

By using
ethyl N-t-butyloxycarboryl-1,2,3,6-tetrahydropyridine-4-formate, 4-bromophenyl-1-sulfonylchloride and (4-(piperazine-1-yl)phenyl)boronic acid pinacol ester (produced by Nanjing Ailikaide Chemical Co., Ltd.) as raw materials, white solid N-hydroxyl-1-((4'-(piperazine-1-yl)-[1,1'-biphenyl]-4-yl)sulfonyl)-1,2,3,6-tetrahydropyridine-4-formamide (11.3% total yield) was prepared by steps similar to those in Embodiment 1.

MS (ESI) m/z 443 (M+1)+.

¹HNMR (400 MHz, DMSO) δ=8.21 (s, 1H), 7.85 (d, J=8.4 Hz, 2H), 7.77 (d, J=8.4 Hz, 2H), 7.64 (d, J=8.8 Hz, 2H), 7.06 (d, J=8.8 Hz, 2H), 6.33 (s, 1H), 3.72-3.64 (m, 4H), 3.12 (t, J=5.6 Hz, 2H), 2.61 (s, 3H), 2.42 (s, 3H), 2.28 (s, 2H), 1.16 (s, 3H).

Embodiment 11: Preparation of N-hydroxyl-1-((4'-(4-cyclopropylpiperazine-1-yl)-[1,1'-biphenyl]-4-yl)sulfonyl)-1,2,3,6-tetrahydropyridine-4-formamide

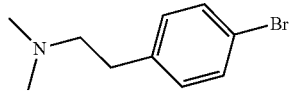

By using ethyl N-t-butyloxycarboryl-1,2,3,6-tetrahydropyridine-4-formate, 4-bromophenyl-1-sulfonylchloride and (4-(4-cyclopropylpiperazine-1-yl)phenyl)boronic acid (produced by Nanjing Ailikaide Chemical Co., Ltd.) as raw materials, white solid N-hydroxyl-1-((4'-(4-cyclopropylpiperazine-1-yl)-[1,1'-biphenyl]-4-yl)sulfonyl)-1,2,3,6-tetrahydropyridine-4-formamide (7.4% total yield) was prepared by steps similar to those in Embodiment 1.

MS (ESI) m/z 483 (M+1)+.

¹HNMR (400 MHz, DMSO) δ=7.86 (d, J=8.6, 2H), 7.78 (d, J=8.0, 2H), 7.64 (d, J=8.9, 2H), 7.05 (d, J=8.9, 2H), 6.36 (s, 1H), 3.65-3.64 (m, 2H), 3.21-3.16 (m, 4H), 3.14-3.12 (t, J=5.7, 2H), 2.69-2.67 (m, 4H), 3.42-3.29 (m, 2H), 1.68-1.65 (m, 1H), 0.46-0.44 (m, 2H), 0.37-0.35 (m, 2H).

Embodiment 12: Preparation of N-hydroxyl-1-((4'-(2-(dimethylamino)ethyl)-[1,1'-biphenyl]-4-yl)sulfonyl)-1,2,3,6-tetrahydropyridine-4-formamide 1. Preparation of 2-(4-bromophenyl)-N,N-dimethylacetamide

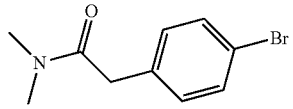

4-bromophenylacetic acid (2.00 g, 9.30 mmol) was dissolved in dichloromethane (50.0 mL), then added with N,N-diisopropylethylamine (3.61 g, 27.9 mmol, 4.87 mL), 1-ethyl-(3-dimethylaminopropyl)carbodiimide hydrochloride (3.57 g, 18.6 mmol), 1-hydroxybenzotriazole (1.21 g, 18.6 mmol) and dimethylamine (2.10 g, 46.5 mmol). The reaction system was stirred and reacted for 2 h. The reaction solution was poured into 50.0 mL of water, and extracted for two times with dichloromethane. The organic phases were combined, condensed and purified by column chromatography to obtain colorless oily 2-(4-bromophenyl)-N,N-dimethylacetamide (2.00 g, 8.26 mmol, 88.82% yield).

2. Preparation of 2-(4-bromophenyl)-N,N-dimethylethylamide

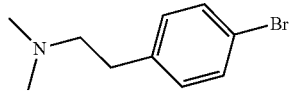

2-(4-bromophenyl)-N,N-dimethylacetamide (2.00 g, 8.26 mmol) was dissolved in tetrahydrofuran (50.0 mL) in an ice bath, added with lithium aluminum hydride (245 mg, 6.44 mmol) and reacted for 1 h. 1N NaOH was added to quench the reaction, and the reaction solution was filtered. The filtrate was condensed and purified by column chromatography to obtain colorless oily 2-(4-bromophenyl)-N,N-dimethylethylamide (800 mg, 3.51 mmol, 65.30% yield).

3. Preparation of 4-((N,N-dimethylamino)ethyl)phenylboronic acid pinacol ester

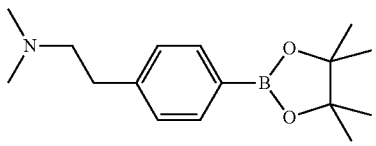

2-(4-bromophenyl)-N,N-dimethylethylamide (800 mg, 3.51 mmol) was added in 1,4-dioxane (10.0 mL) at the room temperature, and then added with bis(pinacolato)diboron (891 mg, 3.51 mmol), potassium acetate (369 mg, 5.27 mmol) and [1,1'-bis(diphenylphosphino)ferrocene]palladium dichloride (80.0 mg, 3.51 mmol). The reaction system was heated to 90° C. and reacted for 2 h in the atmosphere of nitrogen. The reaction solution was condensed and purified by column chromatography to obtain brown oily 4-((N,N-dimethylamino)ethyl)phenylboronic acid pinacol ester (500 mg, 1.82 mmol, 51.76% yield).

4. Preparation of N-hydroxyl-1-((4'-(2-(dimethylamino)ethyl)-[1,1'-biphenyl]-4-yl)sulfonyl)-1,2,3,6-tetrahydropyridine-4-formamide

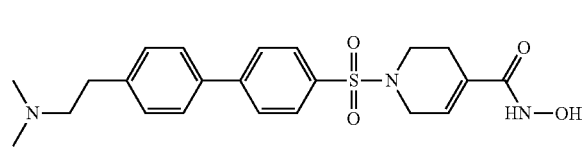 [SMILES: CN(C)CCc1ccc(-c2ccc(S(=O)(=O)N3CC=C(C(=O)NO)CC3)cc2)cc1]

By using ethyl N-t-butyloxycarboryl-1,2,3,6-tetrahydropyridine-4-formate (10.0 g, 39.2 mmol), 4-bromophenyl-1-sulfonylchloride (1.38 g, 5.40 mmol) and (4-(2-(dimethylamino)ethyl-phenylboronic acid pinacol ester (369 mg, 1.34 mmol) as raw materials, white solid N-hydroxyl-1-((4'-(2-(dimethylamino)ethyl)-[1,1'-biphenyl]-4-yl)sulfonyl)-1,2,3,6-tetrahydropyridine-4-formamide (30.5 mg, 71.0 μmol, 5.3% total yield) was prepared by steps similar to those in Embodiment 1.

MS (ESI) m/z 430 (M+1)+.

¹HNMR (400 MHz, DMSO) δ=8.29 (s, 0.7H), 7.91 (d, J=8.8 Hz, 2H), 7.84 (d, J=8.4 Hz, 2H), 7.69 (d, J=8.4 Hz, 2H), 7.40 (d, J=8.0 Hz, 2H), 6.34 (s, 1H), 3.76-3.66 (m, 4H), 3.13 (t, J=5.2 Hz, 2H), 3.02-2.90 (m, 4H), 2.59 (s, 6H), 2.28 (s, 2H).

Embodiment 13: Preparation of N-hydroxyl-1-(6-(4-(4-methylpiperazine-1-yl)phenyl)pyridine-3-yl)sulfonyl)-1,2,3,6-tetrahydropyridine-4-formamide

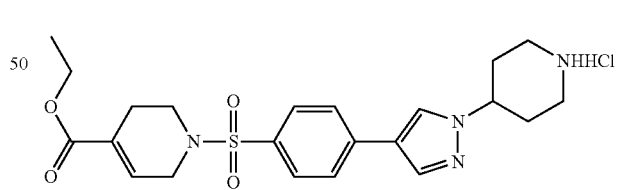

By using ethyl N-t-butyloxycarboryl-1,2,3,6-tetrahydropyridine-4-formate, 6-bromopyridyl-3-sulfonylchloride and 4-(4-methylpiperazine-1-yl)phenylboronic acid pinacol ester (produced by Shanghai Accela ChemBio Co., Ltd.) as raw materials, white solid N-hydroxyl-1-(6-(4-(4-methylpiperazine-1-yl)phenyl)pyridine-3-yl)sulfonyl)-1,2,3,6-tetrahydropyridine-4-formamide (12.6% total yield) was prepared by steps similar to those in Embodiment 1.

MS (ESI) m/z 458 (M+1)+.

¹HNMR (400 MHz, DMSO) δ=8.87 (s, 1H), 8.24 (s, 1H), 8.14-8.02 (m, 3H), 7.06 (d, J=9.2 Hz, 2H), 6.34 (s, 1H), 3.71 (s, 2H), 3.33 (s, 4H), 3.19 (t, J=5.2 Hz, 2H), 2.67 (s, 4H), 2.59-2.34 (m, 3H), 2.27 (s, 2H).

Embodiment 14: Preparation of N-hydroxyl-1-((4-(1-(1-methylpiperidine-4-yl)-1H-pyrazol-4-yl)phenyl)sulfonyl)-1,2,3,6-tetrahydropyridine-4-formamide 1. Preparation of ethyl 1-((4-(1-(tert-butoxycarbonyl)piperidine-4-yl)-1H-pyrazol-4-yl)phenyl)sulfonyl)-1,2,3,6-tetrahydropyridine-4-formate

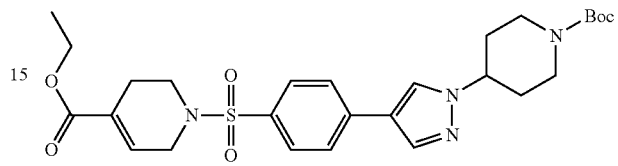

Ethyl 1-((4-bromophenyl)sulfonyl)-1,2,3,6-tetrahydropyridine-4-formate (1.00 g, 2.67 mmol) was dissolved in DMF (12.0 mL) and water (4.00 mL), and then added with tert-butyl 4-(4-(4,4,5,5-tetramethyl-1,3,2-dioxocyclopentaborane-2-yl)-1H-pyrazol-1-yl)piperidine-1-formate (1.00 mg, 2.67 mmol, produced by Nanjing Ailikaide Chemical Co., Ltd.), [1,1'-bis(diphenylphosphino)ferrocene]palladium dichloride. The reaction system was stirred and reacted for 3 h at 80° C. in the atmosphere of nitrogen. The reaction solution was added with ethyl acetate (60.0 mL) and water (40.0 mL) to extract the organic layer, and then extracted with ethyl acetate (40.0 mL×2). The organic layer was combined, dried with anhydrous sodium sulfate, and evaporated to remove the solvent. The crude product was purified by column chromatography to obtain ethyl 1-((4-(1-(tert-butoxycarbonyl)piperidine-4-yl)-1H-pyrazol-4-yl)phenyl)sulfonyl)-1,2,3,6-tetrahydropyridine-4-formate (1.45 g, 2.17 mmol, 81% yield).

2. Preparation of ethyl 1-((4-(1-(piperidine-4-yl)-1H-pyrazol-4-yl)phenyl)sulfonyl)-1,2,3,6-tetrahydropyridine-4-formate hydrochloride Ethyl 1-((4-(1-(tert-butoxycarbonyl)piperidine-4-yl)-1H-pyrazol-4-yl)phenyl)sulfonyl)-1,2,3,6-tetrahydropyridine-4-formate (1.45 g, 2.17 mmol) was dissolved in dichloromethane (20.0 mL), then added with 5.00 mL of concentrated hydrochloric acid (12N), and stirred for 1 h at the room temperature. The reaction solution was evaporated to remove the solvent so as to obtain ethyl 1-((4-(1-(tert-butoxycarbonyl)piperidine-4-yl)-1H-pyrazol-4-yl)phenyl)sulfonyl)-1,2,3,6-tetrahydropyridine-4-formate hydrochloride (1.22 g, 2.54 mmol, 95% yield).

3. Preparation of ethyl 1-((4-(1-(1-methylpiperidine-4-yl)-1H-pyrazol-4-yl)phenyl)sulfonyl)-1,2,3,6-tetrahydropyridine-4-formate

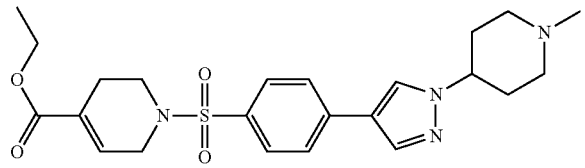 [SMILES: CCOC(=O)C1=CCN(S(=O)(=O)c2ccc(-c3cnn(C4CCN(C)CC4)c3)cc2)CC1]

Ethyl 1-((4-(1-(piperidine-4-yl)-1H-pyrazol-4-yl)phenyl)sulfonyl)-1,2,3,6-tetrahydropyridine-4-formate hydrochloride (400 mg, 900 μmol) was dissolved in 1,2-dichloroethane (12.0 mL). The mixture was added with formaldehyde aqueous solution (40%, 338 mg, 4.50 mmol) and sodium triacetylborohydride (936 mg, 4.50 mmol), and stirred and reacted for 3 h at the room temperature. The reaction solution was added with ethyl acetate (40.0 mL) and water (20.0 mL) to extract the organic layer, and then extracted with dichloromethane (20 mL×2). Subsequently, the organic phase was washed with saturated salt water, dried with anhydrous sodium sulfate, spin-dried and purified by column chromatography to obtain the resulting product ethyl 1-((4-(1-(1-methylpiperidine-4-yl)-1H-pyrazol-4-yl)phenyl)sulfonyl)-1,2,3,6-tetrahydropyridine-4-format e (345 mg, 87.0 μmol, 11.5% yield).

4. Preparation of 1-((4-(1-(1-methylpiperidine-4-yl)-1H-pyrazol-4-yl)phenyl)sulfonyl)-1,2,3,6-tetrahydropyridine-4-(N-hydroxyl)formamide

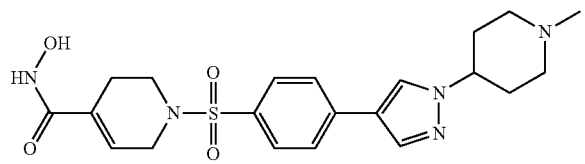 [SMILES: CN1CCC(n2cc(-c3ccc(S(=O)(=O)N4CC=C(C(=O)NO)CC4)cc3)cn2)CC1]

Ethyl 1-((4-(1-(1-methylpiperidine-4-yl)-1H-pyrazol-4-yl)phenyl)sulfonyl)-1,2,3,6-tetrahydropyridine-4-format e (345 mg, 750 μmol) was dissolved in dichloromethane (5.00 mL) and methanol (5.00 mL). The reaction system was cooled to 0° C., added with hydroxylamine aqueous solution (50%, 20.0 mL) and sodium hydroxide (150 mg, 3.76 mmol), heated to the room temperature and stirred for 3 h. The reaction solution was adjusted with hydrochloric acid (1N) until the pH is neutral, and the resulting product was spin-dried and dissolved in methanol. The solution was condensed to obtain high performance liquid phase, and the high performance liquid phase was purified to obtain the resulting product 1-((4-(1-(1-methylpiperidine-4-yl)-1H-pyrazol-4-yl)phenyl)sulfonyl)-1,2,3,6-tetrahydropyridine-4-(N-hydroxyl)formamide (44.5 mg, 200 μmol, 7.28% yield).

MS (ESI) m/z 446 (M+1)+.

$^1$HNMR (400 MHz, DMSO) δ=8.18 (s, 1H), 8.04 (s, 1H), 7.85-7.83 (d, J=8.4 Hz, 2H), 7.75-7.73 (d, J=8.8 Hz, 2H), 6.36 (s, 1H), 4.20-4.15 (m, 1H), 3.64-3.63 (d, J=2.8 Hz, 2H), 3.13-3.10 (t, J=6.0 Hz, 2H), 2.94-2.91 (d, J=11.6 Hz, 2H), 2.27-2.25 (m, 2H), 2.20 (s, 3H), 2.18-2.04 (m, 2H), 2.04-1.98 (m, 4H).

Embodiment 15: Preparation of N-hydroxyl-1-((4'-(4-methylpiperazine-1-yl)-[1,1'-biphenyl]-4-yl)sulfonyl)-1,2,3,4-tetrahydropyridine-4-formamide

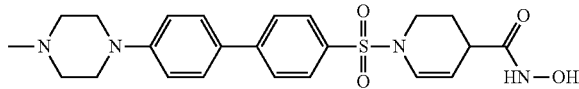

By using ethyl N-t-butyloxycarboryl-1,2,3,4-tetrahydropyridine-4-formate, 4-bromophenyl-1-sulfonylchloride and 4-(4-methylpiperazine-1-yl)phenyl)boronic acid pinacol ester (produced by Shanghai Accela ChemBio Co., Ltd.) as raw materials, white solid N-hydroxyl-1-((4'-(4-methylpiperazine-1-yl)-[1,1'-biphenyl]-4-yl)sulfonyl)-1,2,3,4-tetrahydropyridine-4-formamide (6.1% total yield) was prepared by steps similar to those in Embodiment 1.

MS (ESI) m/z 457 (M+1)+.

$^1$HNMR (400 MHz, DMSO) δ=7.87-7.85 (d, J=8.4 Hz, 2H), 7.84-7.82 (d, J=9.2 Hz, 2H), 7.79-7.77 (d, J=8.4 Hz, 2H), 7.06-7.04 (d, J=8.8 Hz, 2H), 6.73-6.71 (m, 1H), 4.93-4.90 (m, 1H), 3.46-3.37 (m, 2H), 3.26-3.23 (m, 4H), 2.75-2.73 (m, 1H), 2.52-2.50 (m, 4H), 2.26 (s, 3H), 1.83-1.79 (m, 1H), 1.64-1.61 (m, 1H).

Embodiment 16: Preparation of N-hydroxyl-1-((4-(1-acetylpiperidine-4-yl)-1H-pyrazol-4-yl)phenyl)sulfonyl)-1,2,3,6-tetrahydropyridine-4-formamide

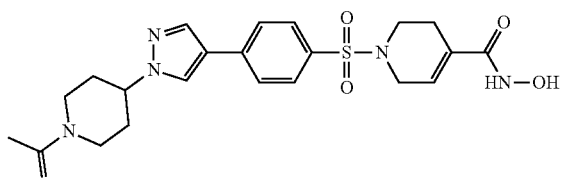

By using ethyl 1-((4-(1-(piperidine-4-yl)-1H-pyrazol-4-yl)phenyl)sulfonyl)-1,2,3,6-tetrahydropyridine-4-formate hydrochloride and acetic anhydride as raw materials, white solid N-hydroxyl-1-((4-(1-acetylpiperidine-4-yl)-1H-pyrazol-4-yl)phenyl)sulfonyl)-1,2,3,6-tetrahydropyridine-4-formamide (14.9% total yield) was prepared by steps similar to those in Embodiment 14.

MS (ESI) m/z 474 (M+1)+.

$^1$HNMR (400 MHz, DMSO) δ=8.45 (s, 1H), 8.05 (s, 1H), 7.84-7.83 (d, J=8.4, 1H), 7.75-7.73 (d, J=8.4 Hz, 2H), 6.36 (s, 1H), 4.26-4.20 (m, 1H), 3.64-3.63 (d, J=2.8 Hz, 2H), 3.12-3.10 (t, J=2.4 Hz, 2H), 3.02-2.99 (d, J=11.6 Hz, 2H), 2.43 (s, 3H), 2.36-2.23 (m, 4H), 2.28-2.05 (m, 4H).

Embodiment 17: Preparation of N-hydroxyl-1-((4-(6-(4-(2-methoxyethyl)piperazine-1-yl)pyridine-3-yl)phenyl)sulfonyl)-1,2,3,6-tetrahydropyridine-4-formamide 1. Preparation of 1-(5-bromopyridine-2-yl)-4-(2-methoxyethyl)piperazine

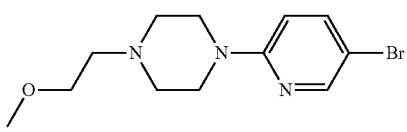 [SMILES: COCCN1CCN(c2ccc(Br)cn2)CC1]

5-bromo-2-chloropyridine (1.00 g, 5.19 mmol), 1-(2-methoxyethyl)piperazine (899 mg, 6.23 mmol) and potassium carbonate (1.08 g, 8.00 mmol) were dissolved in N,N-dimethylformamide. The reaction solution was heated to 70° C., stirred overnight, evaporated to remove the solvent and purified by column chromatography to obtain 1-(5-bromopyridine-2-yl)-4-(2-methoxyethyl) piperazine (500 mg, 1.66 mmol, 32% yield).

MS (ESI) m/z 300 (M+1)+.

2. Preparation of 1-((4-(6-(2-methoxyethyl)piperazine-1-yl)pyridine-3-yl)phenyl)sulfonyl)-N-((tetrahydro-2H-pyran-2-yl)oxo)-1,2,3,6-tetrahydropyridine-4-formamide

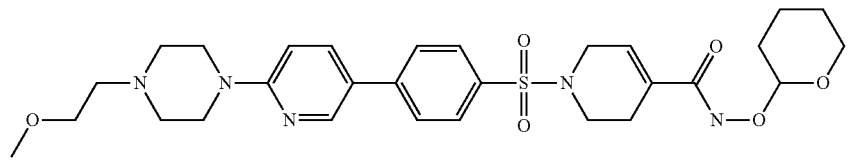 [SMILES: COCCN1CCN(c2ccc(-c3ccc(S(=O)(=O)N4CC=C(C(=O)NOC5CCCCO5)CC4)cc3)cn2)CC1]

1-(5-bromopyridine-2-yl)-4-(2-methoxyethyl)piperazine (450 mg, 1.50 mmol) was dissolved in 15.0 mL of ethanol, and added with chloro[4,5-bis(diphenylphosphino)-9,9-dimethylxanthene)-2-(2-aminobiphenyl)]palladium (II) (45.8 mg), potassium acetate (441 mg, 4.50 mmol) and 2-dicyclohexylphosphino-2',4',6'-triisopropylbiphenyl (28.6 mg, 60.0 μmol). The reaction system was heated to 80° C. and reacted for 2 h in the atmosphere of nitrogen. The reaction system was added with ethyl 1-((4-bromophetnyl)sulfonyl)-1,2,3,6-tetrahydropyridine-4-formate (655 mg, 1.47 mmol) and potassium carbonate (610 mg, 4.41 mmol), heated to 100° C. and reacted overnight. At the end of reaction, the reaction solution was evaporated to remove the solvent, and purified by column chromatography to obtain 1-((4-(6-(2-methoxyethyl)piperazine-1-yl)pyridine-3-yl)phenyl)sulfonyl)-N-((tetrahydro-2H-pyran-2-yl)oxo)-1,2,3,6-tetrahydropyridine-4-formamide (170 mg, 290 μmol, 20% yield).

MS (ESI) m/z 586 (M+1)+.

3. Preparation of N-hydroxyl-1-((4-(6-(4-(2-methoxyethyl)piperazine-1-yl)pyridine-3-yl)phenyl)sulfonyl)-1,2,3,6-tetrahydropyridine-4-formamide

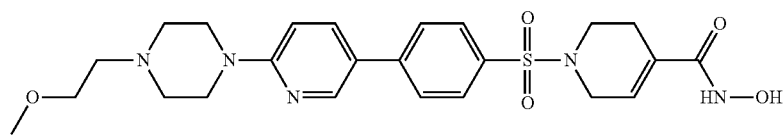 [SMILES: COCCN1CCN(c2ccc(-c3ccc(S(=O)(=O)N4CC=C(C(=O)NO)CC4)cc3)cn2)CC1]

1-((4-(6-(2-methoxyethyl)piperazine-1-yl)pyridine-3-yl)phenyl)sulfonyl)-N-((tetrahydro-2H-pyran-2-yl)oxo)-1,2,3,6-tetrahydropyridine-4-formamide (170 mg, 290 μmol) was added with hydrochloric acid (0.1N, 10.0 mL), and stirred overnight at the room temperature to obtain high performance liquid phase. The high performance liquid phase was purified to obtain white solid N-hydroxyl-1-((4-(6-(4-(2-methoxyethyl)piperazine-1-yl)pyridine-3-yl)phenyl)sulfonyl)-1,2,3,6-tetrahydropyridine-4-formamide (25.6 mg, 46.8 μmol, 16.1%).

MS (ESI) m/z 502 (M+1)+.

$^1$HNMR (400 MHz, DMSO) δ=8.52 (d, J=2.6 Hz, 1H), 7.95 (dd, J=2.6, 8.9 Hz, 1H), 7.86 (d, J=8.6, 2H), 7.78 (d, J=8.6, 2H), 6.96 (d, J=9.0, 1H), 6.32 (m, 1H), 3.65-3.61 (m, 6H), 3.54-3.52 (t, J=5.48, 2H), 3.25 (s, 3H), 3.11 (t, J=5.5, 2H), 2.79-2.77 (m, 6H), 2.28-2.25 (m, 2H).

Embodiment 18: Preparation of N-hydroxyl-1-((4'-((diethylamino)methyl)-[1,1'-biphenyl]-4-yl)sulfonyl)-1,2,3,6-tetrahydropyridine-4-formamide

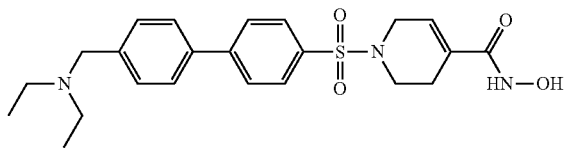

By using ethyl N-t-butyloxycarboryl-1,2,3,6-tetrahydropyridine-4-formate, 4-bromophenyl-1-sulfonylchloride and (4-((diethylamino)methyl)phenyl)boronic acid pinacol ester (produced by Shanghai Bide Pharmatech Ltd.) as raw materials, white solid N-hydroxyl-1-((4'-((diethylamino)methyl)-[1,1'-biphenyl]-4-yl)sulfonyl)-1,2,3,6-tetrahydropyridine-4-form amide (7.1% total yield) was prepared by steps similar to those in Embodiment 1.

MS (ESI) m/z 444 (M+1)+.

$^1$HNMR (400 MHz, DMSO) δ=8.25 (s, 0.4H), 7.95-7.93 (m, 2H), 7.87-7.85 (m, 2H), 7.81-7.79 (m, 2H), 7.61-7.59 (m, 2H), 6.33 (s, 1H), 4.14 (s, 2H), 3.66 (d, J=4.0 Hz, 2H), 3.14 (t, J=4.0 Hz, 2H), 2.95-2.90 (m, 4H), 2.27 (s, 2H), 1.16 (t, J=8.0 Hz, 6H).

Embodiment 19: Preparation of N-hydroxyl-1-((4'-(piperidine-1-yl-methyl)-[1,1'-biphenyl]-4-yl)sulfonyl)-1,2,3,6-tetrahydropyridine-4-formamide

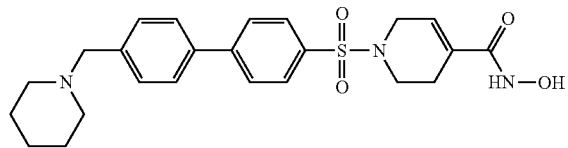 [SMILES: O=C(NO)C1=CCN(S(=O)(=O)c2ccc(-c3ccc(CN4CCCCC4)cc3)cc2)CC1]

By using ethyl N-t-butyloxycarboryl-1,2,3,6-tetrahydropyridine-4-formate, 4-bromophenyl-1-sulfonylchloride and 4-(piperidylmethyl)phenylboronic acid pinacol ester (produced by J&K Scientific LTD.) as raw materials, white solid N-hydroxyl-1-((4'-(piperidine-1-yl-methyl)-[1,1'-biphenyl]-4-yl)sulfonyl)-1,2,3,6-tetrahydropyridine-4-formamide (5.1% total yield) was prepared by steps similar to those in Embodiment 1.

MS (ESI) m/z 456 (M+1)+.

$^1$HNMR (400 MHz, DMSO) δ=8.4 (s, 1H), 7.93 (d, J=8.2 Hz, 2H), 7.84 (d, J=8.0 Hz, 2H), 7.71 (d, J=8.0 Hz, 2H), 7.43 (d, J=8.0 Hz, 1H), 6.36 (s, 1H), 3.66 (m, 4H), 3.14 (t, J=6.0 Hz, 2H), 2.32-2.35 (m, 6H), 1.49-1.52 (m, 4H), 1.39-1.41 (m, 2H).

Embodiment 20: Preparation of N-hydroxyl-1-((4'-((4-methylpiperazine-1-yl)methyl)-[1,1'-biphenyl]-4-yl)sulfonyl)-1,2,3,6-tetrahydropyridine-4-formamide

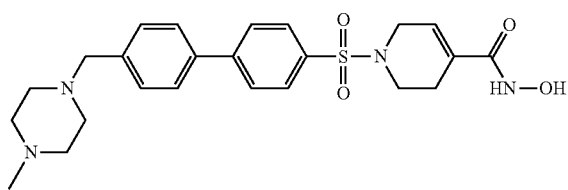 [SMILES: CN1CCN(Cc2ccc(-c3ccc(S(=O)(=O)N4CC=C(C(=O)NO)CC4)cc3)cc2)CC1]

By using ethyl N-t-butyloxycarboryl-1,2,3,6-tetrahydropyridine-4-formate, 4-bromophenyl-1-sulfonylchloride and 4-(4-methyl-1-piperazinylmethyl)phenylboronic acid pinacol ester (produced by Nanjing Ailikaide Chemical Co., Ltd.) as raw materials, white solid N-hydroxyl-1 ((4'-((4-methylpiperazine-1-yl)methyl)-[1,1'-biphenyl]-4-yl)sulfonyl)-1,2,3,6-tetrahydropyridine-4-formamide (5.5% total yield) was prepared by steps similar to those in Embodiment 1.

MS (ESI) m/z 471 (M+1)+.

$^1$HNMR (400 MHz, DMSO) δ=7.93 (d, J=8.0 Hz, 2H), 7.84 (d, J=8.0 Hz, 2H), 7.71 (d, J=8.0 Hz, 2H), 7.43 (d, J=8.0 Hz, 2H), 6.36 (s, 1H), 3.66-3.67 (d, J=4.0 Hz, 2H), 3.52 (s, 1H), 3.14-3.17 (m, 2H), 2.4-2.42 (m, 6H), 2.32-2.37 (m, 4H), 2.19 (s, 3H).

Embodiment 21: Preparation of N-hydroxyl-1-((4'-(morpholinylmethyl)-[1,1'-biphenyl]-4-yl)sulfonyl)-1,2,3,6-tetrahydropyridine-4-formamide

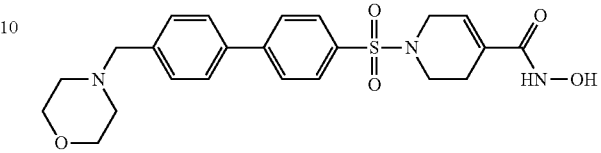

By using ethyl N-t-butyloxycarboryl-1,2,3,6-tetrahydropyridine-4-formate, 4-bromophenyl-1-sulfonylchloride and 4-(4-morpholinylmethyl)phenylboronic acid pinacol ester (produced by Nanjing Ailikaide Chemical Co., Ltd.) as raw materials, white solid N-hydroxyl-1-((4'-(morpholinylmethyl)-[1,1'-biphenyl]-4-yl)sulfonyl)-1,2,3,6-tetrahydropyridine-4-formamide (6.3% total yield) was prepared by steps similar to those in Embodiment 1.

MS (ESI) m/z 458 (M+1)+.

$^1$HNMR (400 MHz, DMSO) δ=7.93 (d, J=8.0 Hz, 2H), 7.84 (d, J=8.0 Hz, 2H), 7.72 (d, J=8.0 Hz, 2H), 7.45 (d, J=8.0 Hz, 2H), 6.36 (s, 1H), 3.66 (s, 1H), 3.57-3.60 (m, 4H), 3.52 (s, 4H), 3.13-3.16 (m, 2H), 2.38 (m, 4H), 2.31 (s, 2H).

Embodiment 22: Preparation of N-hydroxyl-1-((4'-((2-(dimethylamino)ethyl)aminoformyl)-[1,1'-biphenyl]-4-yl)sulfonyl)-1,2,3,6-tetrahydropyridine-4-formamide

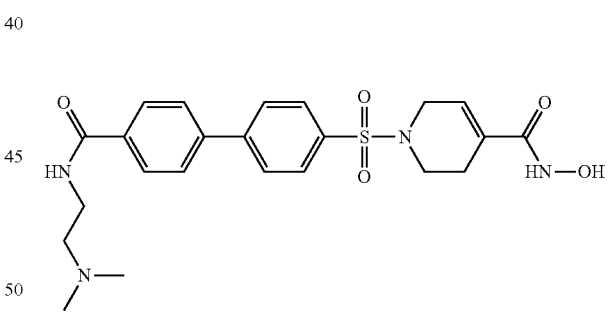

By using ethyl N-t-butyloxycarboryl-1,2,3,6-tetrahydropyridine-4-formate, 4-bromophenyl-1-sulfonylchloride and ((((dimethylamino)ethyl)aminoformyl)phenyl)boronic acid (produced by Nanjing Ailikaide Chemical Co., Ltd.) as raw materials, white solid N-hydroxyl-1-((4'-((2-(dimethylamino)ethyl)aminoformyl)-[1,1'-biphenyl]-4-yl)sulfonyl)-1,2,3,6-tetrahydropyridine-4-formamide (7.8% total yield) was prepared by steps similar to those in Embodiment 1.

MS (ESI) m/z 473 (M+1)+.

$^1$HNMR (400 MHz, DMSO) δ=8.6 (s, 1H), 7.98-8.01 (m, 4H), 7.86-7.89 (m, 4H), 6.37 (s, 1H), 3.67 (m, 2H), 3.40-3.43 (m, 2H), 3.14-3.17 (m, 2H), 2.56-2.58 (m, 2H), 2.29-2.31 (m, 8H).

Embodiment 23: Preparation of N-hydroxyl-1-((3'-(4-methylpiperazine-1-yl)-[1,1'-biphenyl]-4-yl)sulfonyl)-1,2,3,6-tetrahydropyridine-4-formamide

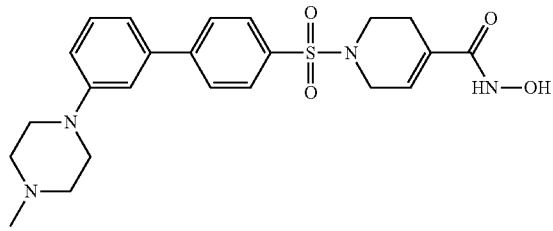 [SMILES: CN1CCN(c2cccc(-c3ccc(S(=O)(=O)N4CC=C(C(=O)NO)CC4)cc3)c2)CC1]

By using ethyl N-t-butyloxycarboryl-1,2,3,6-tetrahydropyridine-4-formate, 4-bromophenyl-1-sulfonylchloride and (3-(4-methylpiperazine-1-yl)phenyl)boronic acid (produced by Shanghai Accela ChemBio Co., Ltd.) as raw materials, white solid N-hydroxyl-1-((3'-(4-methylpiperazine-1-yl)-[1,1'-biphenyl]-4-yl)sulfonyl)-1,2,3,6-tetrahydropyridine-4-formamide (1.6% total yield) was prepared by steps similar to those in Embodiment 1.

MS (ESI) m/z 457 (M+1)+.

$^1$HNMR (400 MHz, DMSO) δ=8.16 (s, 1H), 7.92-7.89 (m, 2H), 7.34 (d, J=8.0 Hz, 1H), 7.19-7.23 (m, 1H), 6.99-7.05 (dd, J=8.0, 2.0 Hz, 1H), 6.36 (s, 1H), 3.65 (d, J=3.2, 2H), 3.26-3.24 (m, 5H), 3.13 (t, J=5.6 Hz, 2H), 2.48-2.44 (m, 3H), 2.36-2.28 (m, 2H), 2.23 (s, 3H).

Embodiment 24: Preparation of N-hydroxyl-1-((4-(6-(4-methyl-1,4-diazaheptane-1-yl)pyridine-3-yl)phenyl)sulfonyl)-1,2,3,6-tetrahydropyridine-4-formamide

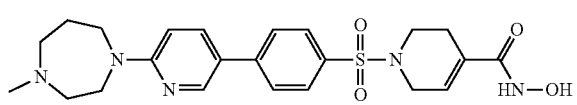

By using ethyl N-t-butyloxycarboryl-1,2,3,6-tetrahydropyridine-4-formate, 4-bromophenyl-1-sulfonylchloride, 1-methyl-1,4-diazaheptane and 2,5-dibromopyridine as raw materials, white solid N-hydroxyl-1-((4-(6-(4-methyl-1,4-diazaheptane-1-yl)pyridine-3-yl)phenyl)sulfonyl)-1,2,3,6-tetrahydropyridine-4-formamide (7.8% total yield) was prepared by steps similar to those in Embodiment 17.

MS (ESI) m/z 472 (M+1)+.

$^1$H NMR (400 MHz, DMSO) δ=8.53 (d, J=2.1 Hz, 1H), 8.24 (s, 1.4H), 7.92 (d, J=9.1 Hz, 1H), 7.88 (d, J=8.4 Hz, 2H), 7.77 (d, J=8.4 Hz, 2H), 6.76 (d, J=9.0 Hz, 1H), 6.36 (s, 1H), 3.83 (s, 2H), 3.65 (d, J=6.5 Hz, 4H), 3.12 (t, J=5.5 Hz, 2H), 2.73 (s, 2H), 2.61 (s, 2H), 2.33 (t, J=8.4 Hz, 5H), 1.96 (s, 2H).

Embodiment 25: Preparation of N-hydroxyl-1-((2'-((dimethylamino)methyl)-[1,1'-biphenyl]-4-yl)sulfonyl)-1,2,3,6-tetrahydropyridine-4-formamide

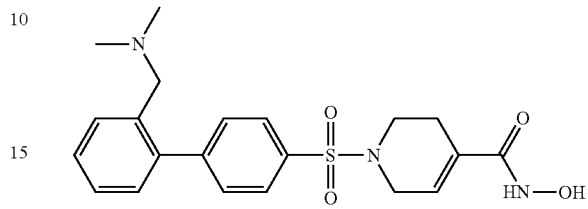

By using ethyl N-t-butyloxycarboryl-1,2,3,6-tetrahydropyridine-4-formate, 4-bromophenyl-1-sulfonylchloride and 2-(N,N-dimethylmethylene)phenylboronic acid (produced by Nanjing Ailikaide Chemical Co., Ltd.) as raw materials, white solid N-hydroxyl-1-((2'-((dimethylamino)methyl)-[1,1'-biphenyl]-4-yl)sulfonyl)-1,2,3,6-tetrahydropyridine-4-formamide (5.9% total yield) was prepared by steps similar to those in Embodiment 1.

MS (ESI) m/z 416 (M+1)+.

$^1$H NMR (400 MHz, DMSO) δ=10.70 (s, 1H), 8.14 (s, 0.8H), 7.84 (d, J=8.4 Hz, 2H), 7.74-7.52 (m, 3H), 7.44 (td, J=13.0, 7.3 Hz, 2H), 7.30 (d, J=7.1 Hz, 1H), 6.37 (s, 1H), 3.70 (d, J=2.5 Hz, 2H), 3.53 (s, 2H), 3.18 (t, J=5.7 Hz, 2H), 2.30 (s, 2H), 2.17 (s, 6H).

Embodiment 26: Preparation of N-hydroxyl-1-(((4'-(4-(1-methoxy-2-methylpropane-2-yl)piperazine-1-yl)-[1,1'-biphenyl]-4-yl)sulfonyl)-1,2,3,6-tetrahydropyridine-4-formamide

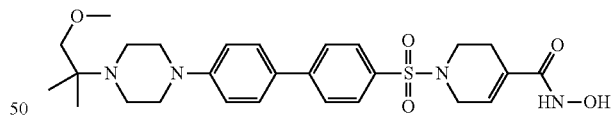

By using ethyl N-t-butyloxycarboryl-1,2,3,6-tetrahydropyridine-4-formate, 4-bromobiphenyl and 1-(1-methoxy-2-methylpropane-2-yl)piperazine as raw materials, white solid N-hydroxyl-1-(((4'-(4-(1-methoxy-2-methylpropane-2-yl)piperazine-1-yl)-[1,1'-biphenyl]-4-yl)sulfonyl)-1,2,3,6-tetrahydropyridine-4-formamide (8.4% total yield) was prepared by steps similar to those in Embodiment 4.

MS (ESI) m/z 529 (M+1)+.

$^1$H NMR (400 MHz, DMSO) δ=10.73-10.62 (m, 1H), 8.88-8.78 (m, 1H), 8.14 (s, 0.7H), 7.87 (d, J=8.6 Hz, 2H), 7.78 (d, J=8.5 Hz, 2H), 7.66 (d, J=8.9 Hz, 2H), 7.06 (d, J=8.2 Hz, 2H), 6.36 (s, 1H), 3.64 (s, 2H), 3.32 (d, J=13.7 Hz, 12H), 3.12 (t, J=5.6 Hz, 3H), 2.31 (s, 2H), 1.15 (s, 6H).

Embodiment 27: Preparation of N-hydroxyl-1-((4'-((methylpiperidine-4-yl)amino)-[1,1'-biphenyl]-4-yl)sulfonyl)-1,2,3,6-tetrahydropyridine-4-formamide

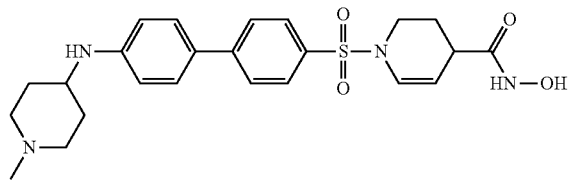 [SMILES: CN1CCC(Nc2ccc(-c3ccc(S(=O)(=O)N4C=CC(C(=O)NO)CC4)cc3)cc2)CC1]

By using ethyl N-t-butyloxycarboryl-1,2,3,6-tetrahydropyridine-4-formate, 4-bromobiphenyl and 1-methylpiperidine-4-amine as raw materials, white solid N-hydroxyl-1-((4'-((methylpiperidine-4-yl)amino)-[1,1'-biphenyl]-4-yl)sulfonyl)-1,2,3,6-tetrahydropyridine-4-formamide (0.5% total yield) was prepared by steps similar to those in Embodiment 4.

MS (ESI) m/z 471 (M+1)+.

$^1$H NMR (400 MHz, DMSO) δ=10.68 (s, 1H), 10.47 (s, 1H), 8.83 (s, 0.8H), 7.81 (d, J=8.5 Hz, 2H), 7.74 (d, J=8.6 Hz, 2H), 7.54 (d, J=8.5 Hz, 2H), 6.73 (d, J=7.6 Hz, 2H), 6.36 (s, 1H), 6.18 (s, 1H), 3.62 (s, 2H), 3.47 (d, J=50.1 Hz, 2H), 3.11 (t, J=5.6 Hz, 4H), 2.72 (s, 3H), 2.30 (s, 2H), 2.09 (d, J=13.0 Hz, 2H), 1.74 (d, J=9.7 Hz, 2H).

Embodiment 28: Preparation of N-hydroxyl-1 ((4'-((methylpiperidine-4-yl)amino)-[1,1'-biphenyl]-4-yl)sulfonyl)-1,2,3,4-tetrahydropyridine-4-formamide

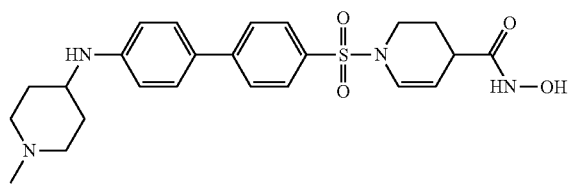 [SMILES: CN1CCC(Nc2ccc(-c3ccc(S(=O)(=O)N4C=CC(C(=O)NO)CC4)cc3)cc2)CC1]

By using ethyl N-t-butyloxycarboryl-1,2,3,4-tetrahydropyridine-4-formate, 4-bromobiphenyl and 1-methylpiperidine-4-amine as raw materials, white solid N-hydroxyl-1-((4'-((methylpiperidine-4-yl)amino)-[1,1'-biphenyl]-4-yl)sulfonyl)-1,2,3,4-tetrahydropyridine-4-formamide (2.7% total yield) was prepared by steps similar to those in Embodiment 4.

MS (ESI) m/z 471 (M+1)+.

$^1$H NMR (400 MHz, DMSO) δ=10.47 (s, 1H), 8.25 (s, 1H), 7.79 (d, J=8.7 Hz, 2H), 7.73 (d, J=8.7 Hz, 2H), 7.52 (d, J=8.7 Hz, 2H), 6.70 (dd, J=13.8, 5.3 Hz, 3H), 5.96 (d, J=8.0 Hz, 1H), 4.90 (dd, J=8.4, 3.9 Hz, 1H), 3.51-3.21 (m, 4H), 2.85 (d, J=11.9 Hz, 2H), 2.73 (d, J=5.5 Hz, 1H), 2.27 (s, 3H), 2.21 (t, J=10.7 Hz, 2H), 1.92 (d, J=10.9 Hz, 2H), 1.79 (s, 1H), 1.66-1.56 (m, 1H), 1.46 (dd, J=20.8, 10.0 Hz, 2H).

Embodiment 29: Preparation of N-hydroxyl-1-((4'-(4-methylpiperazinyl)-[1,1'-biphenyl]-4-yl)sulfonyl)-1,2,3,6-tetrahydropyridine-4-formamide

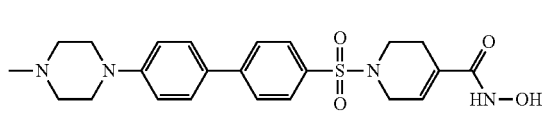

By using ethyl N-t-butyloxycarboryl-1,2,3,6-tetrahydropyridine-4-formate, 4-bromophenyl-1-sulfonylchloride and 4-(4-methylpiperazinyl)phenylboronic acid pinacol ester (produced by Shanghai Accela ChemBio Co., Ltd.) as raw materials, white solid N-hydroxyl-1-((4'-(4-methylpiperazinyl)-[1,1'-biphenyl]-4-yl)sulfonyl)-1,2,3,6-tetrahydropyridine-4-formamide (9.3% total yield) was prepared by steps similar to those in Embodiment 1.

MS (ESI) m/z 457 (M+1)+.

$^1$HNMR (400 MHz, DMSO) δ=8.22 (s, 1H), 7.84 (d, J=8.0 Hz, 2H), 7.77 (d, J=8.0 Hz, 2H), 7.63 (d, J=8.0 Hz, 2H), 7.09 (d, J=8.0 Hz, 2H), 6.32 (s, 1H), 3.63 (s, 2H), 3.33-3.32 (m, 4H), 3.12-3.10 (t, 2H), 2.88-2.87 (m, 2H), 2.51 (s, 3H), 2.27 (s, 2H).

Embodiment 30: Preparation of N-hydroxyl-1-((4'-(4-(1-methoxyisopropyl)piperazinyl)-[1,1'-biphenyl]-4-yl)sulfonyl)-1,2,3,6-tetrahydropyridine-4-formamide

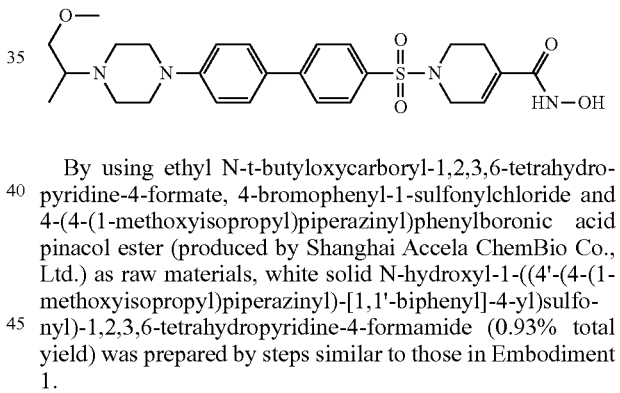

By using ethyl N-t-butyloxycarboryl-1,2,3,6-tetrahydropyridine-4-formate, 4-bromophenyl-1-sulfonylchloride and 4-(4-(1-methoxyisopropyl)piperazinyl)phenylboronic acid pinacol ester (produced by Shanghai Accela ChemBio Co., Ltd.) as raw materials, white solid N-hydroxyl-1-((4'-(4-(1-methoxyisopropyl)piperazinyl)-[1,1'-biphenyl]-4-yl)sulfonyl)-1,2,3,6-tetrahydropyridine-4-formamide (0.93% total yield) was prepared by steps similar to those in Embodiment 1.

MS (ESI) m/z 515 (M+1)+.

$^1$HNMR (400 MHz, DMSO) δ=10.6 (br, 1H), 8.8 (br, 1H), 7.84 (d, J=8.0 Hz, 2H), 7.77 (d, J=8.0 Hz, 2H), 7.63 (d, J=8.0 Hz, 2H), 7.03 (d, J=7.0 Hz, 2H), 6.35 (s, 1H), 3.63 (s, 2H), 3.60-3.31 (m, 2H), 3.29-3.25 (m, 3H), 3.22-3.21 (m, 4H), 3.12 (t, J=6.0 Hz, 2H), 2.84-2.82 (m, 1H), 2.71-2.70 (m, 4H), 2.30 (s, 2H), 1.01 (d, J=5.0 Hz, 3H).

Embodiment 31: Preparation of N-hydroxyl-1-((4'-(2-(diethylamino)ethyl)-[1,1'-biphenyl]-4-yl)sulfonyl)-1,2,3,6-tetrahydropyridine-4-formamide

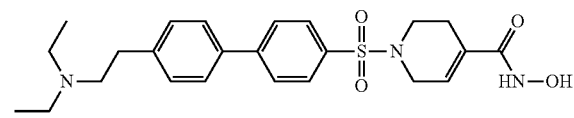

By using ethyl N-t-butyloxycarboryl-1,2,3,6-tetrahydropyridine-4-formate, 4-bromophenyl-1-sulfonylchloride, 4-bromophenylacetic acid and diethylamine hydrochloride as raw materials, white solid N-hydroxyl-1-((4'-(2-(diethylamino)ethyl)-[1,1'-biphenyl]-4-yl)sulfonyl)-1,2,3,6-tetrahydropyridine-4-formamide (0.16% total yield) was prepared by steps similar to those in Embodiment 12.

MS (ESI) m/z 458 (M+1)+.

¹HNMR (400 MHz, DMSO) δ=7.92 (d, J=8.0 Hz, 2H), 7.82 (d, J=8.0 Hz, 2H), 7.70 (d, J=8.0 Hz, 2H), 7.41 (d, J=8.0 Hz, 2H), 6.36 (s, 1H), 3.65 (s, 2H), 3.14 (t, J=8.0 Hz, 2H), 2.99-2.86 (m, 8H), 2.31 (s, 2H), 1.12 (t, J=5.0 Hz, 6H).

Embodiment 32: Preparation of N-hydroxyl-1-((4-(2-(2-methoxyethyl)isoindoline-5-yl)phenyl)sulfonyl)-1,2,3,6-tetrahydropyridine-4-formamide

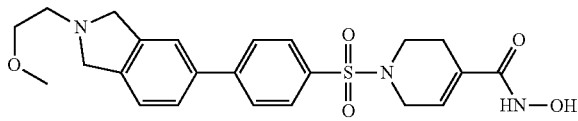

By using ethyl N-t-butyloxycarboryl-1,2,3,6-tetrahydropyridine-4-formate, 4-bromophenyl-1-sulfonylchloride and 5-bromo-2-(2-methoxyethyl)isoindoline as raw materials, white solid N-hydroxyl-1-((4-(2-(2-methoxyethyl)isoindoline-5-yl)phenyl)sulfonyl)-1,2,3,6-tetrahydropyridine-4-formamide (4.9% total yield) was prepared by steps similar to those in Embodiment 3.

MS (ESI) m/z 458 (M+1)+.

¹HNMR (400 MHz, DMSO) δ=7.91 (d, J=8.0 Hz, 2H), 7.85 (d, J=8.0 Hz, 2H), 7.74-7.70 (m, 2H), 7.50 (d, J=8.0 Hz, 2H), 6.33 (s, 1H), 4.59 (d, J=4.0 Hz, 4H), 3.70-3.66 (m, 4H), 3.51-3.49 (m, 2H), 3.33 (s, 3H), 3.13 (t, J=6.0 Hz, 2H), 2.28 (s, 2H).

Embodiment 33: Preparation of 1-((4'-(1-(dimethylamino)ethyl)-[1,1'-biphenyl]-4-yl)sulfonyl)-N-hydroxyl-1,2,3,6-tetrahydropyridine-4-formamide

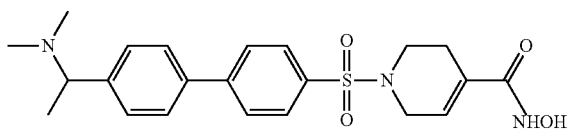

By using ethyl N-t-butyloxycarboryl-1,2,3,6-tetrahydropyridine-4-formate, 4-bromophenyl-1-sulfonylchloride and 4'-(1-(dimethylamino)ethylphenylboronic acid (produced by Nanjing Ailikaide Chemical Co., Ltd.) as raw materials, white solid 1-((4'-(1-(dimethylamino)ethyl)-[1,1'-biphenyl]-4-yl)sulfonyl)-N-hydroxyl-1,2,3,6-tetrahydropyridine-4-formamide (6.0% total yield) was prepared by steps similar to those in Embodiment 1.

MS (ESI) m/z 430 (M+1)+.

¹HNMR (400 MHz, DMSO) δ=7.95 (d, J=8.0 Hz, 2H), 7.86 (d, J=8.0 Hz, 2H), 7.78 (d, J=8.0 Hz, 2H), 7.55 (d, J=8.0 Hz, 2H), 6.33 (s, 1H), 3.99 (s, 1H) 3.66 (s, 2H), 3.53 (s, 2H), 3.14 (s, 2H), 2.27-2.42 (m, 8H), 1.48 (d, J=6.4 Hz, 3H).

Embodiment 34: Preparation of 1-((4'-((4-ethyl(2-methoxyethyl)amino)methyl)-[1,1'-biphenyl]-4-yl)sulfonyl)-N-hydroxyl-1,2,3,6-tetrahydropyridine-4-formamide

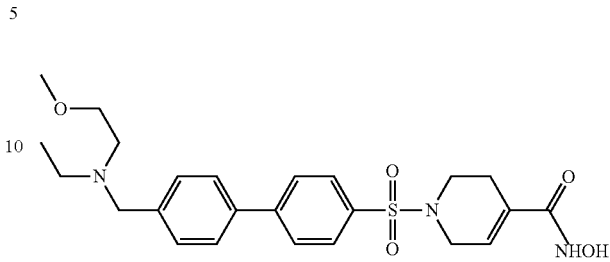

By using ethyl N-t-butyloxycarboryl-1,2,3,6-tetrahydropyridine-4-formate, 4-bromophenyl-1-sulfonylchloride and 4-(ethyl(2-methoxyethyl)amino)methylphenylboronic acid (produced by Nanjing Ailikaide Chemical Co., Ltd.) as raw materials, white solid 1-((4'-((4-ethyl(2-methoxyethyl)amino)methyl)-[1,1'-biphenyl]-4-yl)sulfonyl)-N-hydroxyl-1,2,3,6-tetrahydropyridine-4-formamide (1.5% total yield) was prepared by steps similar to those in Embodiment 1.

MS (ESI) m/z 474 (M+1)+.

¹HNMR (400 MHz, DMSO) δ=7.94 (d, J=8.0 Hz, 2H), 7.86 (d, J=8.0 Hz, 2H), 7.73 (d, J=8.0 Hz, 2H), 7.45 (d, J=8.0 Hz, 2H), 6.36 (s, 1H), 3.66 (s, 2H), 3.64 (s, 2H), 3.43 (d, J=6.0 Hz, 2H), 3.32 (s, 3H), 3.14 (d, J=4.8 Hz 2H), 2.51-2.64 (m, 4H), 2.32 (s, 2H), 1.00 (t, J=6.8 Hz, 3H).

Embodiment 35: Preparation of 1-((4'-(1-(diethylamino)ethyl)-[1,1'-biphenyl]-4-yl)sulfonyl)-N-hydroxyl-1,2,3,6-tetrahydropyridine-4-formamide

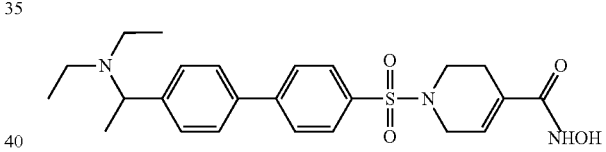

By using ethyl N-t-butyloxycarboryl-1,2,3,6-tetrahydropyridine-4-formate, 4-bromophenyl-1-sulfonylchloride and 4'-(1-(diethylamino)ethylphenylboronic acid (produced by Nanjing Ailikaide Chemical Co., Ltd.) as raw materials, white solid 1-((4'-(1-(diethylamino)ethyl)-[1,1'-biphenyl]-4-yl)sulfonyl)-N-hydroxyl-1,2,3,6-tetrahydropyridine-4-formamide (3.97% total yield) was prepared by steps similar to those in Embodiment 1.

MS (ESI) m/z 458 (M+1)+.

¹HNMR (400 MHz, DMSO) δ=7.94 (d, J=8.0 Hz, 2H), 7.84 (d, J=8.0 Hz, 2H), 7.73 (d, J=8.0 Hz, 2H), 7.57 (d, J=8.4 Hz, 2H), 6.33 (s, 1H), 4.03 (d, J=6.68 Hz, 1H), 3.66 (s, 2H), 3.16 (t, J=5.36 Hz, 2H), 2.68-2.55 (m, 4H), 2.31 (s, 2H), 1.38 (d, J=6.64 Hz, 3H)), 1.01 (t, J=7.0 Hz, 6H).

Embodiment 36: Preparation of 1-((4'-(4-acetylpiperazine)-1-yl)-[1,1'-biphenyl]-4-yl)sulfonyl)-N-hydroxyl-1,2,3,6-tetrahydropyridine-4-formamide

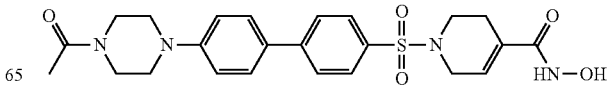

By using ethyl N-t-butyloxycarboryl-1,2,3,6-tetrahydropyridine-4-formate, 4-bromobiphenyl and 4-acetylpiperazine as raw materials, white solid 1-((4'-(4-acetylpiperazine)-1-yl)-[1,1'-biphenyl]-4-yl)sulfonyl)-N-hydroxyl-1,2,3,6-tetrahydropyridine-4-formamide (5.6% total yield) was prepared by steps similar to those in Embodiment 4.

MS (ESI) m/z 485 (M+1)+.

¹HNMR (400 MHz, DMSO) δ=7.84 (d, J=8.0 Hz, 2H), 7.77 (d, J=8.0 Hz, 2H), 7.64 (d, J=8.4 Hz, 2H), 7.06 (d, J=8.0 Hz, 2H), 6.33 (s, 1H), 4.03 (d, J=6.68 Hz, 1H), 3.66 (s, 2H), 3.64 (s, 2H), 3.57 (d, J=4 Hz, 4H), 3.24 (s, 2H), 3.18 (s, 2H), 3.10-3.12 (m, 2H), 2.27 (s, 2H), 2.04 (s, 3H).

Embodiment 37: Preparation of N-hydroxyl-1-((4-(2-(2-methoxyethyl)-1,2,3,4-tetrahydroisoquinoline-7-yl)phenyl)sulfonyl)-1,2,3,6-tetrahydropyridine-4-formamide

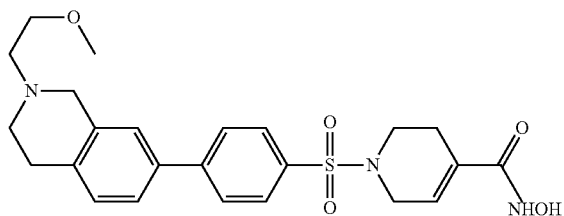

By using ethyl N-t-butyloxycarboryl-1,2,3,6-tetrahydropyridine-4-formate, 4-bromophenyl-1-sulfonylchloride and 7-bromo-2-(2-methoxyethyl)-1,2,3,4-tetrahydroisoquinoline as raw materials, white solid N-hydroxyl-1-((4-(2-(2-methoxyethyl)-1,2,3,4-tetrahydroisoquinoline-7-yl)phenyl)sulfonyl)-1,2,3,6-tetrahydropyridine-4-formamide (8.8% total yield) was prepared by steps similar to those in Embodiment 3.

MS (ESI) m/z 472 (M+1)+.

¹HNMR (400 MHz, DMSO) δ=7.91 (d, J=8.0 Hz, 2H), 7.84 (d, J=8.0 Hz, 2H), 7.58 (d, J=8.0 Hz, 2H), 7.28 (d, J=8.4 Hz, 1H), 6.33 (s, 1H), 4.16 (s, 2H), 3.66-3.68 (m, 4H), 3.31 (s, 3H), 3.26 (s, 2H), 3.07-3.14 (m, 6H), 2.28 (s, 2H).

Embodiment 38: Preparation of N-hydroxyl-1-((4'-((4-(1-methoxy-2-methylpropane-2-yl)piperazine-1-yl)methyl)-[1,1'-biphenyl]-4-yl)sulfonyl)-1,2,3,6-tetrahydropyridine-4-formamide 1. Preparation of 4-((4-(1-methoxy-2-methylpropane-2-yl)piperazinyl)methyl)phenylboronic acid pinacol ester

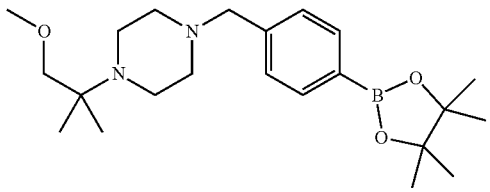

4-bromomethyl phenylboronic acid pinacol ester (1.14 g, 3.85 mmol) and 1-(1-methoxy-2-methylpropane-2-yl)piperazine (474 mg, 2.75 mmol) were dissolved in acetonitrile (20.0 mL), then added with sodium carbonate (874 mg, 8.25 mmol) and stirred overnight at the room temperature. The reaction solution was added with water (50.0 mL) and extracted with ethyl acetate. The organic phases were combined, washed with saturated sodium chloride solution, dried with anhydrous sodium sulfate, evaporated at the reduced pressure to remove the solvent, and purified by column chromatography to obtain 4-((4-(1-methoxy-2-methylpropane-2-yl)piperazinyl)methyl)phenylboronic acid pinacol ester (800 mg, 2.06 mmol, 75% yield).

2. Preparation of N-hydroxyl-1-((4'-((4-(1-methoxy-2-methylpropane-2-yl)piperazine-1-yl)methyl)-[1,1'-biphenyl]-4-yl)sulfonyl)-1,2,3,6-tetrahydropyridine-4-formamide

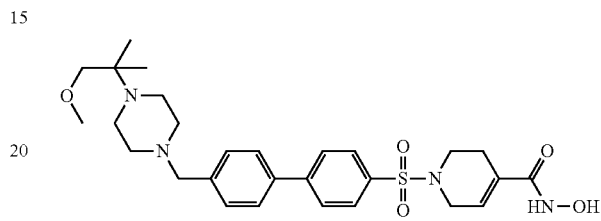

By using ethyl N-t-butyloxycarboryl-1,2,3,6-tetrahydropyridine-4-formate, 4-bromophenyl-1-sulfonylchloride and 4-((4-(1-methoxy-2-methylpropane-2-yl)piperazinyl)methyl)phenylboronic acid pinacol ester as raw materials, N-hydroxyl-1-((4'-((4-(1-methoxy-2-methylpropane-2-yl)piperazine-1-yl)methyl)-[1,1'-biphenyl]-4-yl)sulfonyl)-1,2,3,6-tetrahydropyridine-4-formamide (1.6% total yield) was prepared by steps similar to those in Embodiment 3.

MS (ESI) m/z 543 (M+1)+.

¹HNMR (400 MHz, DMSO) δ=10.67 (s, 1H), 8.15 (s, 0.6H), 7.92 (d, J=8.5 Hz, 2H), 7.84 (d, J=8.5 Hz, 2H), 7.72 (d, J=8.2 Hz, 2H), 7.44 (d, J=8.2 Hz, 2H), 6.36 (s, 1H), 3.66 (s, 2H), 3.57 (s, 3H), 3.27 (d, J=7.8 Hz, 7H), 3.15 (t, J=5.5 Hz, 3H), 2.78 (s, 4H), 2.31 (s, 2H), 1.23-0.98 (m, 6H).

Embodiment 39: Preparation of N-hydroxyl-1-((4'-((4-(1-methoxy-2-methylpropane-2-yl)piperazine-1-yl)methyl)-[1,1'-biphenyl]-4-yl)sulfonyl)-1,2,3,4-tetrahydropyridine-4-formamide

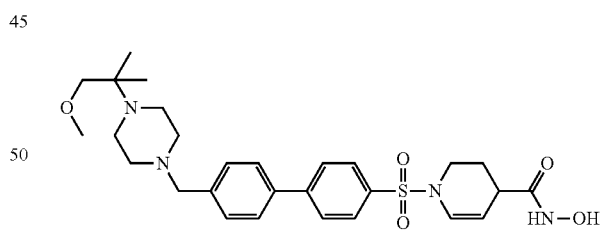

By using ethyl N-t-butyloxycarboryl-1,2,3,4-tetrahydropyridine-4-formate, 4-bromophenyl-1-sulfonylchloride, 4-bromomethyl phenylboronic acid pinacol ester and 1-(1-methoxy-2-methylpropane-2-yl)piperazine as raw materials, N-hydroxyl-1-((4'-((4-(1-methoxy-2-methylpropane-2-yl)piperazine-1-yl)methyl)-[1,1'-biphenyl]-4-yl)sulfonyl)-1,2,3,4-tetrahydropyridine-4-formamide (11% total yield) was prepared by steps similar to those in Embodiment 38.

MS (ESI) m/z 543 (M+1)+.

¹HNMR (400 MHz, DMSO) δ=10.47 (s, 1H), 8.20 (s, 1.4H), 7.92 (d, J=8.6 Hz, 2H), 7.85 (d, J=8.6 Hz, 2H), 7.71 (d, J=8.3 Hz, 2H), 7.42 (d, J=8.2 Hz, 2H), 6.73 (dd, J=8.3, 2.0 Hz, 1H), 4.92 (dd, J=8.4, 4.0 Hz, 1H), 3.50 (s, 2H), 3.43

(dd, J=10.6, 7.0 Hz, 2H), 3.23 (s, 3H), 3.20 (s, 2H), 2.74 (d, J=5.7 Hz, 1H), 2.57 (d, J=21.2 Hz, 4H), 2.38 (s, 4H), 1.79 (s, 1H), 1.62 (d, J=4.6 Hz, 1H), 0.97 (s, 6H).

Embodiment 40: Preparation of N-hydroxyl-1-((4'-(((2-(dimethylamino)ethyl)amino)methyl)-[1,1'-biphenyl]-4-yl)sulfonyl)-1,2,3,6-tetrahydropyridine-4-formamide

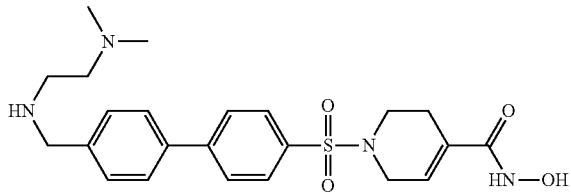 [SMILES: CN(C)CCNCc1ccc(-c2ccc(S(=O)(=O)N3CC=C(C(=O)NO)CC3)cc2)cc1]

By using ethyl N-t-butyloxycarboryl-1,2,3,6-tetrahydropyridine-4-formate, 4-bromophenyl-1-sulfonylchloride, 4-bromomethyl phenylboronic acid pinacol ester and N,N-dimethyl ethylenediamine as raw materials, N-hydroxyl-1-((4'-(((2-(dimethylamino)ethyl)amino)methyl)-[1,1'-biphenyl]-4-yl)sulfonyl)-1,2,3,6-tetrahydropyridine-4-formamide (11% total yield) was prepared by steps similar to those in Embodiment 38.

MS (ESI) m/z 459 (M+1)+.

¹HNMR (400 MHz, DMSO) δ=10.68 (s, 1H), 8.14 (s, 0.4H), 7.96 (d, J=8.4 Hz, 2H), 7.86 (d, J=8.4 Hz, 2H), 7.81 (d, J=8.1 Hz, 2H), 7.65 (d, J=8.0 Hz, 2H), 6.37 (s, 1H), 4.12 (s, 2H), 3.66 (s, 2H), 3.19-3.12 (m, 4H), 3.10 (s, 2H), 2.56 (s, 6H), 2.31 (s, 2H).

Embodiment 41: Preparation of N-hydroxyl-1-((4'-((methyl(1-methylpiperidine-4-yl)amino)methylene)-[1,1'-biphenyl]-4-yl)sulfonyl)-1,2,3,6-tetrahydropyridine-4-formamide

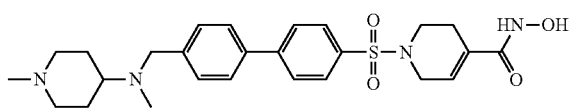

By using ethyl N-t-butyloxycarboryl-1,2,3,6-tetrahydropyridine-4-formate, 4-bromophenyl-1-sulfonylchloride, 4-bromomethyl phenylboronic acid pinacol ester and N,1-dimethylpiperidyl-4-amine as raw materials, N-hydroxyl-1-((4'-((methyl(1-methylpiperidine-4-yl)amino)methylene)-[1,1'-biphenyl]-4-yl)sulfonyl)-1,2,3,6-tetrahydropyridine-4-formamide (0.45% total yield) was prepared by steps similar to those in Embodiment 38.

MS (ESI) m/z 499 (M+1)+.

¹HNMR (400 MHz, DMSO) δ=10.68 (s, 1H), 8.83 (s, 1H), 7.95 (d, J=8.0 Hz, 2H), 7.86 (d, J=8.0 Hz, 2H), 7.78 (s, 2H), 7.65 (br, 2H), 6.36 (s, 1H), 4.23 (m, 2H), 3.67 (s, 2H), 3.46 (m, 2H), 3.15 (t, J=6.0 Hz, 2H), 2.95 (m, 2H), 2.70 (s, 3H), 2.30-2.08 (m, 8H).

Embodiment 42: Preparation of N-hydroxyl-1-((4'-((4-(2-methoxyethyl)-1-piperazinyl)methyl)-[1,1'-biphenyl]-4-yl)sulfonyl)-1,2,3,6-tetrahydropyridine-4-formamide

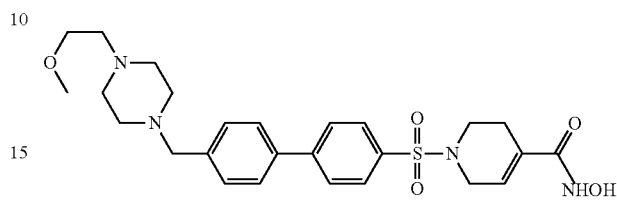

By using ethyl N-t-butyloxycarboryl-1,2,3,6-tetrahydropyridine-4-formate, 4-bromophenyl-1-sulfonylchloride and 4-bromomethyl phenylboronic acid pinacol ester and 4'-(4-(2-methoxyethyl)-1-piperazine (produced by Nanjing Ailikaide Chemical Co., Ltd.) as raw materials, white solid N-hydroxyl-1-((4'-((4-(2-methoxyethyl)-1-piperazinyl)methyl)-[1,1'-biphenyl]-4-yl)sulfonyl)-1,2,3,6-tetrahydropyridine-4-formamide (1.9% total yield) was prepared by steps similar to those in Embodiment 38.

MS (ESI) m/z 515 (M+1)+.

¹HNMR (400 MHz, DMSO) δ=7.93 (d, J=8.0 Hz, 2H), 7.84 (d, J=8.0 Hz, 2H), 7.71 (d, J=8.0 Hz, 2H), 7.44 (d, J=8.0 Hz, 2H), 6.33 (s, 1H), 3.66 (s, 2H), 3.53 (s, 2H), 3.42-3.45 (m, 2H), 3.20 (s, 3H) 3.13 (s, 2H), 2.46-2.60 (m, 8H), 2.27 (s, 2H).

Embodiment 43: Preparation of 1-((4'-((4-ethylpiperazine-1-yl)methyl)-[1,1'-biphenyl]-4-yl)sulfonyl)-N-hydroxyl-1,2,3,6-tetrahydropyridine-4-formamide

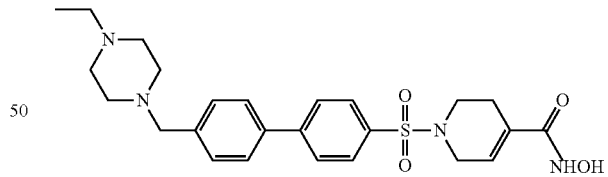

By using ethyl N-t-butyloxycarboryl-1,2,3,6-tetrahydropyridine-4-formate, 4-bromophenyl-1-sulfonylchloride, 4-bromomethyl phenylboronic acid pinacol ester and N-ethylpiperazine as raw materials, 1-((4'-((4-ethylpiperazine-1-yl)methyl)-[1,1'-biphenyl]-4-yl)sulfonyl)-N-hydroxyl-1,2,3,6-tetrahydropyridine-4-formamide (2.2% total yield) was prepared by steps similar to those in Embodiment 38.

MS (ESI) m/z 485 (M+1)+.

¹HNMR (400 MHz, DMSO) δ=7.93 (d, J=8.0 Hz, 2H), 7.86 (d, J=8.0 Hz, 2H), 7.73 (d, J=8.0 Hz, 2H), 7.45 (d, J=8.0 Hz, 2H), 6.36 (s, 1H), 3.66 (s, 2H), 3.54 (s, 2H), 3.14 (d, J=4.8 Hz 2H), 2.31-2.51 (m, 8H), 1.48 (t, J=6.8 Hz, 3H).

Embodiment 44: Preparation of N-hydroxyl-1-((4'-(4-methylpiperazine-1-yl)-[1,1'-biphenyl]-4-yl)sulfonyl)-2,3,6,7-tetrahydro-1H-aza-4-formamide

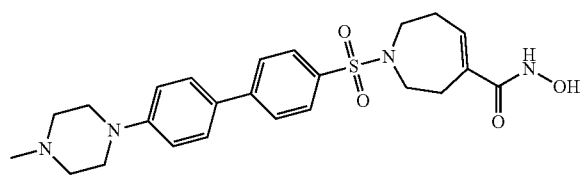 [SMILES: CN1CCN(c2ccc(-c3ccc(S(=O)(=O)N4CCC=C(C(=O)NO)CC4)cc3)cc2)CC1]

By using ethyl N-t-butyloxycarboryl-2,3,6,7-tetrahydro-1H-azepine-4-formate, 4-bromophenyl-1-sulfonylchloride and 4-(4-methylpiperazinyl)phenylboronic acid pinacol ester (produced by Shanghai Accela ChemBio Co., Ltd.) as raw materials, white solid N-hydroxyl-1-((4'-(4-methylpiperazine-1-yl)-[1,1'-biphenyl]-4-yl)sulfonyl)-2,3,6,7-tetrahydro-1H-aza-4-formamide (4.2% total yield) was prepared by steps similar to those in Embodiment 1.

MS (ESI) m/z 471 (M+1)+.

$^1$HNMR (400 MHz, DMSO) δ=8.24 (s, 1H), 7.82 (d, J=8.0 Hz, 2H), 7.69 (d, J=8.0 Hz, 2H), 7.58 (d, J=8.0 Hz, 2H), 7.04 (d, J=8.0 Hz, 2H), 6.29 (s, 1H), 3.58 (s, 2H), 3.33-3.32 (m, 4H), 3.12-3.10 (t, 2H), 2.86-2.85 (m, 4H), 2.48 (s, 3H), 2.26 (s, 2H).

In order to describe the beneficial effects of the present invention, the present invention provides the following test examples.

Test Example 1: Biological Activity Detection

During the deacetylation detection of a substrate, the HDAC inhibition activity of the compound of the present invention was detected.

A: Enzyme Activity Detection of Histone Deacetylase 6 (#50076, BPS Bioscience)

Acetyl on the substrate was removed by the HDAC 6, so that the substrate was activated, and the developing liquid added subsequently could act on the substrate to release the fluorescent group. The size of the fluorescence signal reflected the activity of the HDAC 6. The IC50 detection method for this enzyme was disclosed in Chuping Xu, Elisabetta Soragni Improved Histone Deacetylase Inhibitors as Therapeutics for the Neurdegenerative Disease Friedreich's Ataxia: A New Synthetic Route. The total reaction system (100 μL/well) contained 0.35 ng/μL of HDAC 6, 20 μM of the substrate and the compound in different concentrations. The reaction system was incubated for 30 min at 37° C., and the fluorescence signal was then measured. The inhibition effect of the compound was determined from the obtained data, a concentration response curve was obtained by using the inhibition effect and the concentration of the compound, and the value of IC50 was fitted according to a four-parameter model.

B: Enzyme Activity Detection of Histone Deacetylase 3 (#50003, BPS Bioscience)

Acetyl on the substrate was removed by the HDAC 3, so that the substrate was activated, and the developing liquid added subsequently could act on the substrate to release the fluorescent group. The size of the fluorescence signal reflected the activity of the HDAC 3. The IC50 detection method for this enzyme was disclosed in Chuping Xu, Elisabetta Soragni Improved Histone Deacetylase Inhibitors as Therapeutics for the Neurdegenerative Disease Friedreich's Ataxia: A New Synthetic Route. The total reaction system (100 μL/well) contained 0.16 ng/μL of HDAC 3, 10 μM of the substrate and the compound in different concentrations. The fluorescence signal was detected online at Ex/Em=360/460. The inhibition effect of the compound was determined from the obtained data, a concentration response curve was obtained by using the inhibition effect and the concentration of the compound, and the value of IC$_{50}$ was fitted according to a four-parameter model.

C: Enzyme Activity Detection of Histone Deacetylase 1

Acetyl on the substrate was removed by the HDAC 1, so that the substrate was activated, and the developing liquid added subsequently could act on the substrate to release the fluorescent group. The size of the fluorescence signal reflected the activity of the HDAC 1. The IC50 detection method for this enzyme was disclosed in Chuping Xu, Elisabetta Soragni Improved Histone Deacetylase Inhibitors as Therapeutics for the Neurdegenerative Disease Friedreich's Ataxia: A New Synthetic Route. The total reaction system (100 μL/well) contained 0.28 ng/μL of HDAC 1, 10 μM of the substrate and the compound in different concentrations. The fluorescence signal was detected online at Ex/Em=360/460. The inhibition effect of the compound was determined from the obtained data, a concentration response curve was obtained by using the inhibition effect and the concentration of the compound, and the value of IC$_{50}$ was fitted according to a four-parameter model.

The activities of the compounds prepared in the embodiments against the histone deacetylases 1, 3 and 6 (i.e., HDAC 1, HDAC 3 and HDAC 6) were detected by the above methods, and the test results were shown in Table 2, where the measurements of IC50 of the compounds were classified according to the following description:

"+" represents that the IC$_{50}$ is measured to be greater than 500 nM;

"++" represents that the IC$_{50}$ is measured to be less than 500 nM but greater than 100 nM; and "+++" represents that the IC$_{50}$ is measured to be less than 100 nM.

TABLE 2

| Inhibition activities of the compounds against HDAC 1, HDAC 3 and HDAC 6 | | | |
|---|---|---|---|
| Compound | Activity (HDAC 1) | Activity (HDAC 3) | Activity (HDAC 6) |
| 1 | ND | ++ | +++ |
| 2 | ND | ++ | +++ |
| 6 | +++ | ND | ND |
| 8 | +++ | ND | ND |
| 12 | +++ | ND | ND |
| 13 | +++ | ND | ND |
| 15 | +++ | ND | ND |
| 18 | +++ | ND | ND |
| 19 | +++ | ND | +++ |
| 29 | +++ | +++ | +++ |
| 44 | ++ | ++ | +++ | where ND represents that the data is being detected and analyzed.

The test results show that the compounds of the present invention have excellent inhibition activity against histone deacetylases and can be used for preventing and/or treating diseases caused by the abnormal activity of histone deacetylases, such as cell proliferation disorder diseases, autoimmune diseases, inflammations, neurodegenerative diseases or viral diseases.

Test Example 2: Cell Measurement-Cell Growth Inhibition Measurement

Materials and Reagents

A HepG2 cell strain and an HCT-116 cell strain were purchased from Shanghai Institutes for Biological Sciences; a DMEM high-sugar culture medium and an MEM culture medium were purchased from Hyclone; fetal calf serum was purchased from Gibco; trypsin was purchased from Invitrogen Shanghai; a CCK-8 kit was purchased from Beyotime Institute of Biotechnology; and, the remaining cell culture mediums and other consumables were purchased from Corning China.

Cell Preparation Before Compound Action

HepG2 cells and HCT-116 cells in the logarithmic growth phase were digested by trypsin. After the counting of uniform cell suspension, the cell density was adjusted as 1500 cells/well by a culture medium containing 10% serum. The cells were re-inoculated to a 96-well cell culture plate, and cultured to a volume of 200 μL at 37° C. in an incubator containing 5% $CO_2$. The cells could be tested after being cultured for 24 h.

Compound Action

The cells cultured for 24 h were taken out from the incubator. The culture liquid in the well plate was sucked out, and 200 μL of compound solution prepared in the culture medium containing 10% fetal calf serum was added in each well. Five parallel mediums were provided for each concentration, and a DMSO culture medium was used as negative control. The culture mediums were cultured for 72 h at 37° C. in an incubator containing 5% $CO_2$, and CCK-8 detection was performed.

CCK-8 Detection

A serum-free culture medium and CCK-8 solution were prepared, and CCK-8 working solution was prepared at a ratio of 10:1 (this process should be performed in dark place).

The cells cultured for 72 h were taken out from the incubator. The culture liquid in the well plate was sucked out, and 120 μL of the CCK-8 working solution was added in each well. A well plate without cells was also added with 120 μL of the CCK-8 working solution to serve as blank control. The well plates were cultured for 1 h at 37° C. in an incubator containing 5% $CO_2$ (this process should be performed in dark place).

The well plates were taken out from the incubator, 100 μL of solution in each well was sucked out and added in a new 96-well plate, and the absorbance was measured at 450 nm (this process should be performed in dark place).

Data Processing:

$$\% \text{ Cell Viability} = \frac{100 \times (Tx - B)}{C - B}$$

where Tx is the absorbance of the CCK-8 after the compound acts for 72 h;

C is the absorbance of the CCK-8 after the negative control wells are cultured for 72 h; and B is the absorbance of the CCK-8 in the blank control wells.

The test results of the compounds prepared according to the embodiments during the measurement are shown in Table 3, wherein the measured highest $EC_{50}$ of the compounds during one operation or multiple operations is classified according to the following description:

"+" represents that $EC_{50}$ of the compound is measured to be greater than 100 nM; and "++" represents that $EC_{50}$ of the compound is measured to be less than 100 nM.

TABLE 3

Inhibition activities of the compounds against cancer cells

| Compound | HepG2 | HCT-116 | Compound | HepG2 | HCT-116 |
|---|---|---|---|---|---|
| 1 | + | ND | 2 | ++ | ND |
| 3 | ++ | ND | 4 | ++ | ND |
| 5 | ++ | ND | 6 | ++ | ++ |
| 7 | ++ | ++ | 8 | ++ | ++ |
| 9 | ++ | ND | 10 | ++ | ND |
| 11 | ++ | ND | 12 | ++ | ++ |
| 13 | ++ | ++ | 14 | + | ND |
| 15 | ++ | ++ | 17 | + | ND |
| 18 | ++ | ++ | 19 | ++ | ++ |
| 20 | ++ | ++ | 21 | ++ | ++ |
| 22 | + | ND | 24 | ++ | ND |
| 29 | ++ | ++ | 44 | + | ND | where ND represents that no test analysis has been conducted.

The tests show that the compounds of the present invention have remarkable inhibition effects on cancer cells.

In conclusion, the compound having a novel structure provided by the present invention shows excellent inhibition activity against histone deacetylases, has remarkable inhibition effects on cancer cells, and provides a new choice of drugs used for the clinic treatment and diseases related to the abnormal activity of histone deacetylases.

The invention claimed is:

1. A compound of formula I, or a stereoisomer, pharmaceutically acceptable salt, crystal form, solvate or isotopologue thereof:

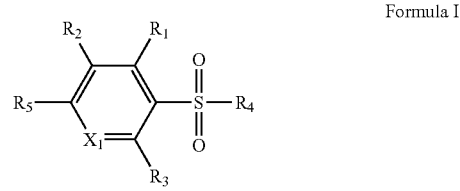

Formula I wherein $X_1$ is $CR_6$ or N;

$R_1$, $R_2$, $R_3$ and $R_6$ are each independently selected from H, halogen, hydroxyl, sulfydryl, amino, phenyl, $C_1$-$C_6$ alkyl, halogen-substituted $C_1$-$C_6$ alkyl, $C_1$-$C_6$ alkoxy or halogen-substituted $C_1$-$C_6$ alkoxy;

$R_4$ is

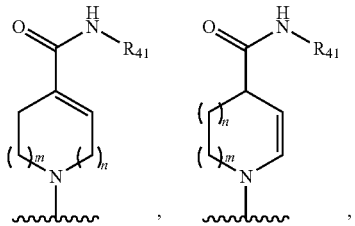

-continued

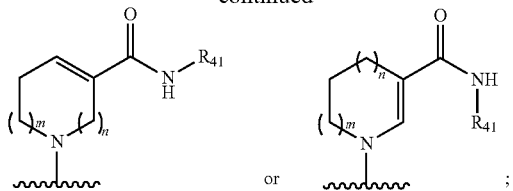

or wherein m and n are each independently an integer selected from 1 or 2; $R_{41}$ is hydroxyl, sulfydryl, amino, epoxyketone, phenyl or substituted phenyl; and
$R_5$ is

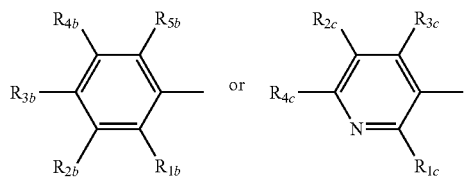

or wherein $R_{1b}$ to $R_{5b}$ are each independently selected from H, halogen, hydroxyl, —C(=O)N($R_{21b}$)($R_{22b}$), $C_1$-$C_6$ alkyl, substituted $C_1$-$C_6$ alkyl, piperazinyl, substituted piperazinyl, amino or substituted amino; wherein $R_{21b}$ and $R_{22b}$ are independently H, $C_1$-$C_6$ alkyl, dimethyl-amino-substituted $C_1$-$C_6$ alkyl or diethylamino-substituted $C_1$-$C_6$ alkyl;

wherein $R_{1c}$, $R_{2c}$ and $R_{3c}$ are each independently H, halogen, $C_1$-$C_6$ alkyl, halogen-substituted $C_1$-$C_6$ alkyl, $C_1$-$C_6$ alkoxy or halogen-substituted $C_1$-$C_6$ alkoxy; and $R_{4c}$ is 5- to 7-membered optionally substituted heterocyclyl having a heteroatom selected from N, O or S.

2. The compound according to claim 1, wherein only one of Rib to $R_{5b}$ is selected from hydroxyl, —C(=O)N($R_{21b}$)($R_{22b}$), $C_1$-$C_6$ alkyl, substituted $C_1$-$C_6$ alkyl, piperazinyl, substituted piperazinyl, amino or substituted amino.

3. The compound according to claim 2, wherein, when $R_{3b}$ is hydroxyl, the compound is represented by formula IIb1:

Formula IIb1

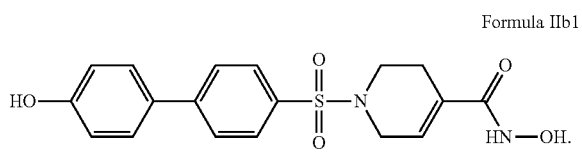 [SMILES: O=C(NO)C1=CCN(S(=O)(=O)c2ccc(-c3ccc(O)cc3)cc2)CC1]

4. The compound according to claim 2, wherein, when $R_{3b}$ is —C(=O)N($R_{21b}$)($R_{22b}$), the compound is represented by formula IIb2:

Formula IIb2

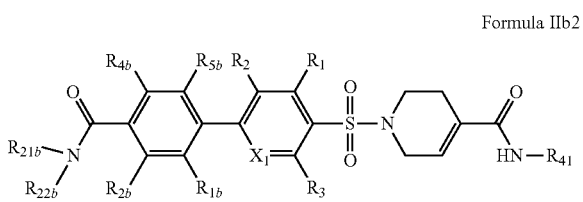

5. The compound according to claim 4, wherein $R_{21b}$ is H, and $R_{22b}$ is $C_1$-$C_3$ alkyl, dimethylamino-substituted $C_1$-$C_3$ alkyl or diethylamino-substituted $C_1$-$C_3$ alkyl.

6. The compound according to claim 5, wherein the compound of formula IIb2 is:

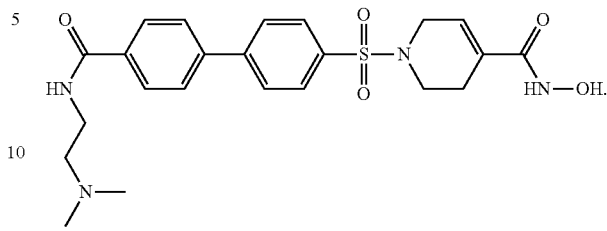

7. The compound according to claim 1, wherein the compound is represented by formula IIb31, IIb32 or IIb33:

Formula IIb31

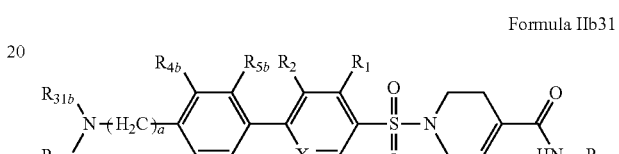

Formula IIb32

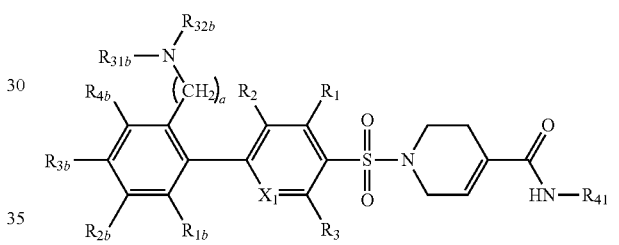

Formula IIb33

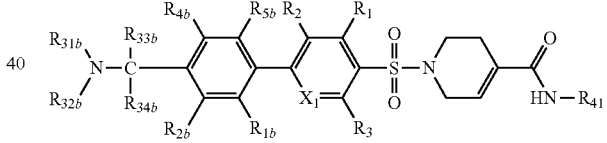

wherein a is an integer from 0 to 6;
$R_{31b}$ and $R_{32b}$ are independently H, $C_1$-$C_6$ alkyl, substituted $C_1$-$C_6$ alkyl having a substituent group of $C_1$-$C_6$ alkoxy or $C_1$-$C_6$ alkyl-substituted amino, or 5- to 7-membered optionally substituted heterocyclyl having a heteroatom selected from N, O or S; or, $R_{31b}$ and $R_{32b}$ are linked to form 5- to 7-membered optionally substituted heterocyclyl; and
$R_{33b}$ is H, and $R_{34b}$ is $C_1$-$C_6$ alkyl.

8. The compound according to claim 7, wherein $R_{31b}$ and $R_{32b}$ are independently 6-membered heterocyclyl; or, $R_{31b}$ and $R_{32b}$ are linked to form 6-membered heterocyclyl.

9. The compound according to claim 7, wherein a is an integer from 0 to 3; $R_{31b}$ and $R_{32b}$ are independently H, methyl, ethyl, methoxyethyl, dimethylaminoethyl or

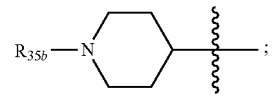

or, $R_{31b}$ and $R_{32b}$ are linked to form

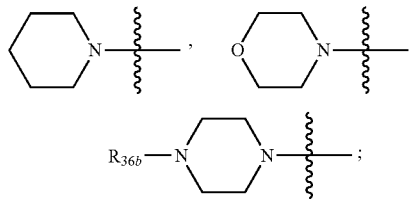

and, $R_{34b}$ is $C_1$-$C_3$ alkyl;

wherein $R_{35b}$ and $R_{36b}$ are independently $C_1$-$C_6$ alkyl or $C_1$-$C_6$ alkoxy-substituted $C_1$-$C_6$ alkyl.

10. The compound according to claim 9, wherein $R_{35b}$ and $R_{36b}$ are independently $C_1$-$C_4$ alkyl, methoxy-substituted $C_1$-$C_4$ alkyl or ethoxy-substituted $C_1$-$C_4$ alkyl.

11. The compound according to claim 7, wherein the compound of formula IIb31, IIb32 or IIb33 is:

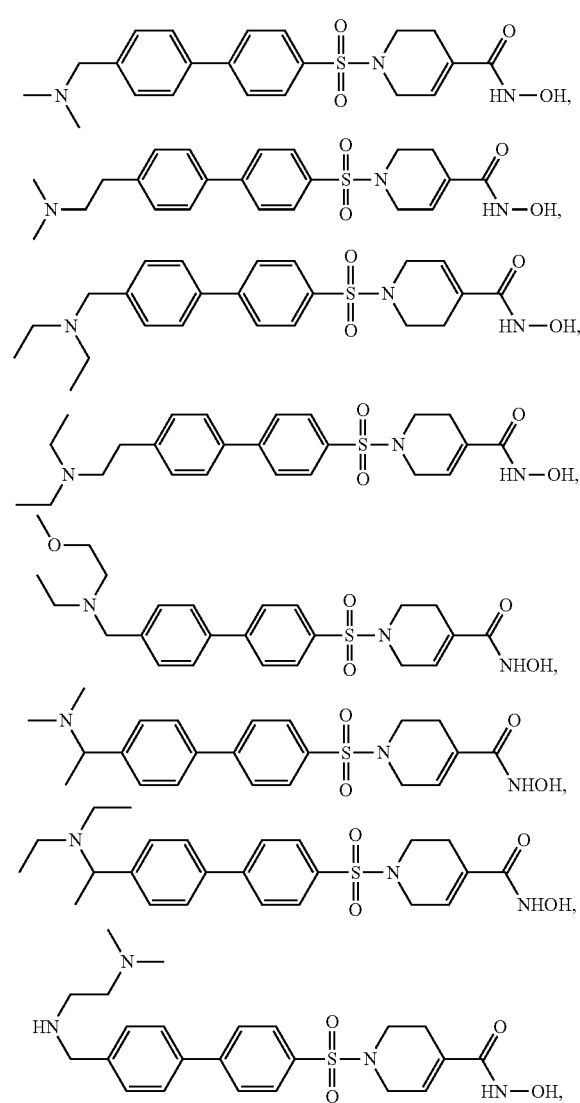

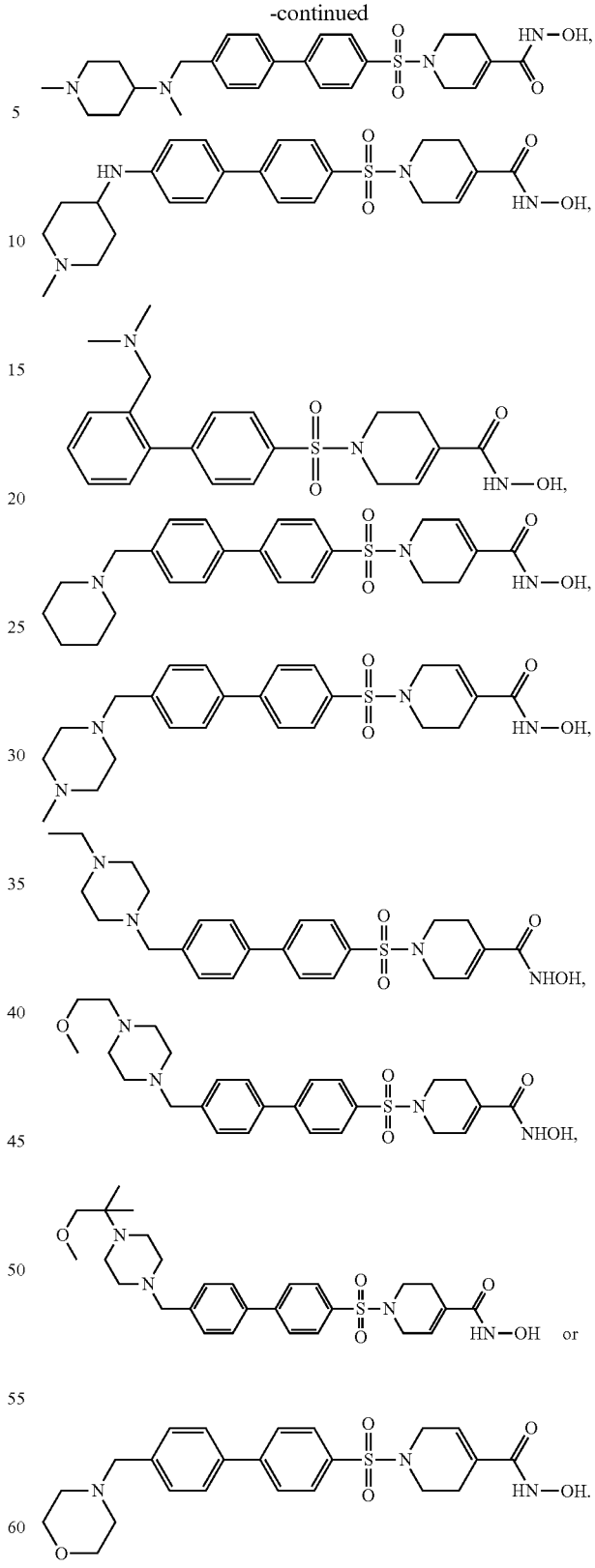

12. The compound according to claim 2, wherein, when one of $R_{2b}$ and $R_{3b}$ is selected from piperazinyl or substituted piperazinyl, the compound is represented by formula IIb4 or IIb5:

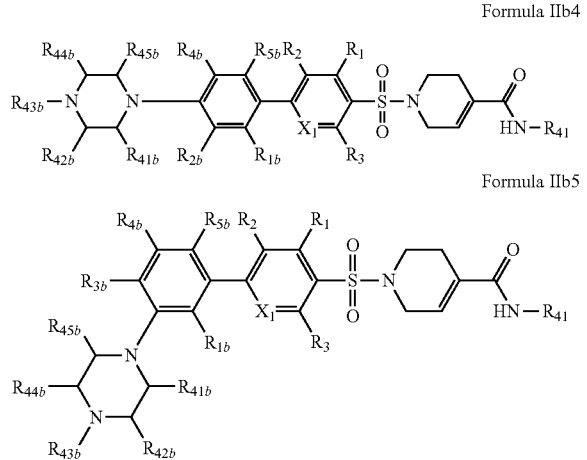

Formula IIb4

Formula IIb5 wherein $R_{41b}$, $R_{42b}$, $R_{44b}$ and $R_{45b}$ are independently H or $C_1$-$C_6$ alkyl; and $R_{43b}$ is H, $C_1$-$C_6$ alkyl, methoxy-substituted $C_1$-$C_6$ alkyl, ethoxy-substituted $C_1$-$C_6$ alkyl, $C_1$-$C_6$ acyl or $C_3$-$C_6$ cycloalkyl.

13. The compound according to claim 12, wherein $R_{41b}$, $R_{42b}$, $R_{44b}$ and $R_{45b}$ are independently H, methyl or ethyl; and, $R_{43b}$ is H, methyl, ethyl, methoxy-substituted $C_2$-$C_4$ alkyl, ethoxy-substituted $C_2$-$C_4$ alkyl, acetyl or cyclopropyl.

14. The compound according to claim 13, wherein the compound of formula IIb4 or IIb5 is:

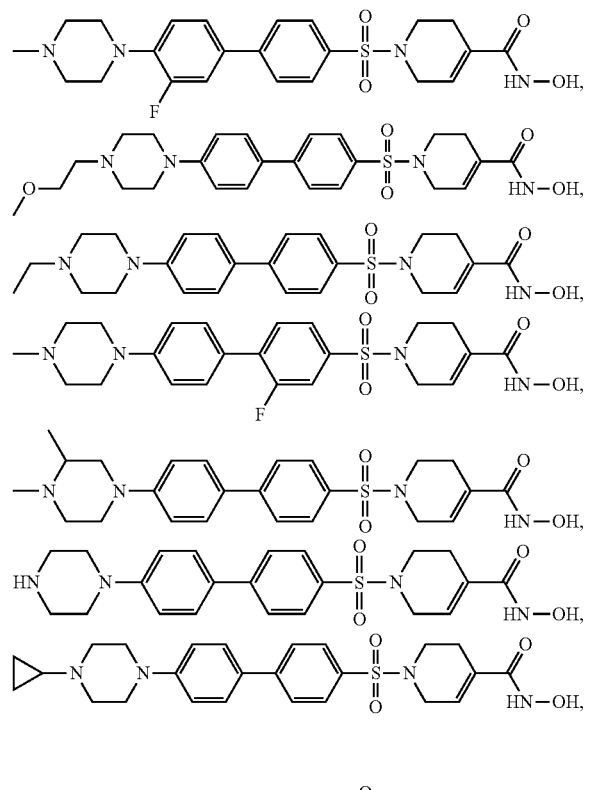

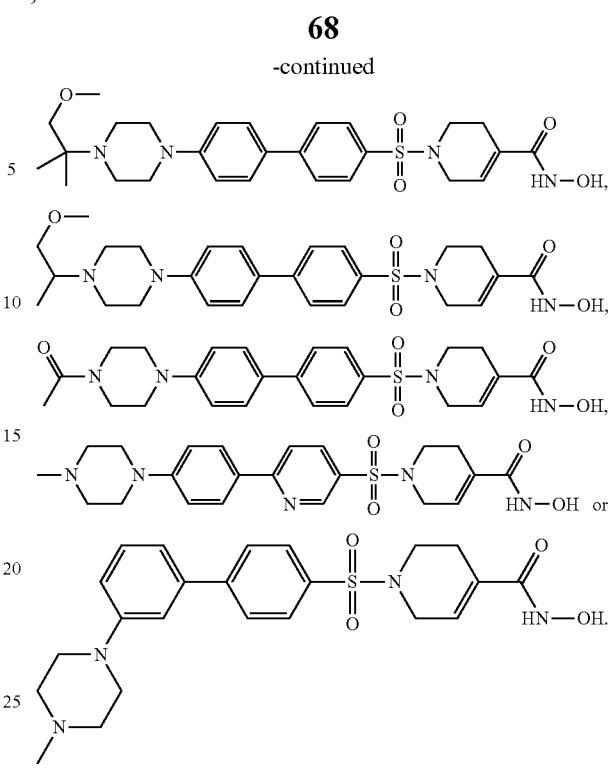

15. The compound according to claim 1, wherein the compound is represented by formula IIc:

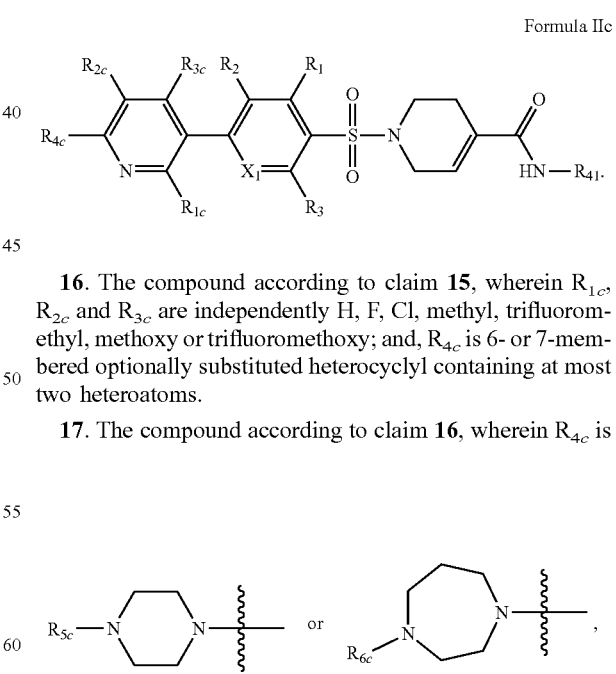

Formula IIc

16. The compound according to claim 15, wherein $R_{1c}$, $R_{2c}$ and $R_{3c}$ are independently H, F, Cl, methyl, trifluoromethyl, methoxy or trifluoromethoxy; and, $R_{4c}$ is 6- or 7-membered optionally substituted heterocyclyl containing at most two heteroatoms.

17. The compound according to claim 16, wherein $R_{4c}$ is wherein $R_{5c}$ and $R_{6c}$ are independently selected from $C_1$-$C_6$ alkyl or $C_1$-$C_6$ alkoxy-substituted $C_1$-$C_6$ alkyl.

18. The compound according to claim 17, wherein the compound of formula IIc is:

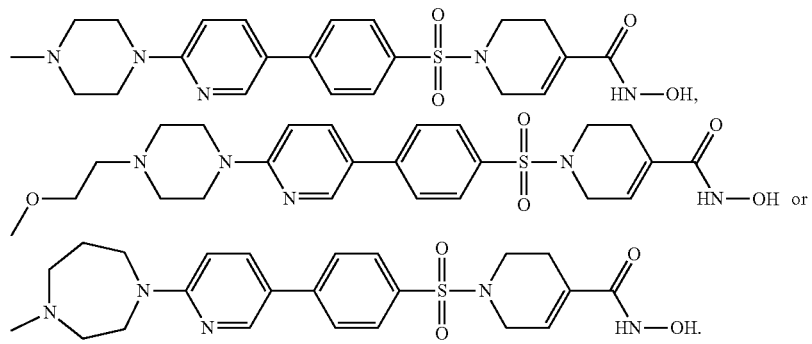

19. The compound according to claim 1, wherein the compound is represented by formula IV:

Formula IV

[structure]

wherein $X_3$ is $CR_{39}$ or N;

$R_{31}$ is hydroxyl or sulfydryl;

$R_{32}$ to $R_{34}$ are independently H, halogen, $C_1$-$C_6$ alkyl, halogen-substituted $C_1$-$C_6$ alkyl, $C_1$-$C_6$ alkoxy or halogen-substituted $C_1$-$C_6$ alkoxy;

$R_{35}$ to $R_{39}$ are independently H, halogen, $C_1$-$C_6$ alkyl, or halogen-substituted $C_1$-$C_6$ alkyl; and $R_{311}$ is H, $C_1$-$C_6$ alkyl, or $C_1$-$C_6$ alkoxy-substituted $C_1$-$C_6$ alkyl.

20. The compound according to claim 19, wherein $R_{32}$ to $R_{34}$ are independently H, F, Cl, methyl, trifluoromethyl, methoxy or trifluoromethoxy; $R_{35}$ to $R_{39}$ are independently H, F, Cl, methyl, or trifluoromethyl; and $R_{311}$ is methyl or ethyl.

21. The compound according to claim 20, wherein the compound of the formula IV is:

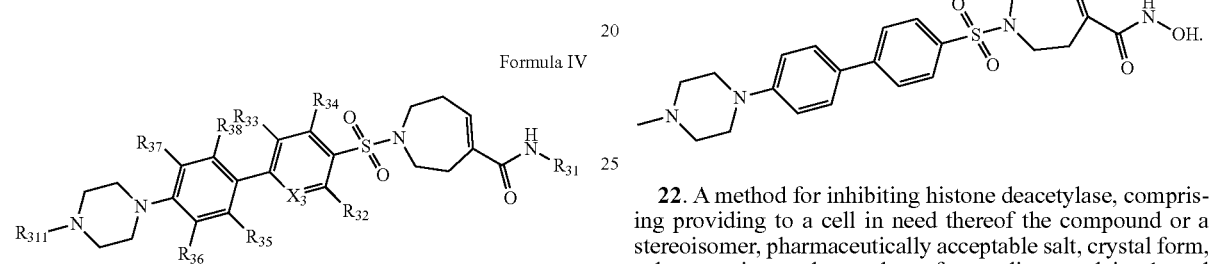

22. A method for inhibiting histone deacetylase, comprising providing to a cell in need thereof the compound or a stereoisomer, pharmaceutically acceptable salt, crystal form, solvate or isotopologue thereof according to claim 1, and inhibiting one or more of HDAC1, HDAC3 and HDAC6.

23. A method for treating liver cancer, comprising administering to a patient in need thereof the compound or stereoisomers, pharmaceutically acceptable salts, crystal forms, solvates or isotopologues thereof according to claim 1.

24. A pharmaceutical composition comprising the compound or stereoisomer, pharmaceutically acceptable salt, crystal form, solvate or isotopologue thereof according to claim 1, and pharmaceutically acceptable adjuvants or auxiliary ingredients.

25. The pharmaceutical composition according to claim 24, wherein the composition is an oral preparation, a sublingual preparation, a buccal preparation, a transdermal absorption preparation or an injectable preparation.

26. The compound of claim 17, wherein $R_{5c}$ and $R_{6c}$ are independently selected from $C_1$-$C_3$ alkyl, methoxy-substituted $C_1$-$C_3$ alkyl or ethoxy-substituted $C_1$-$C_3$ alkyl.

* * * * *